US009000144B2

(12) United States Patent
Tuschl et al.

(10) Patent No.: US 9,000,144 B2
(45) Date of Patent: Apr. 7, 2015

(54) IDENTIFICATION OF NOVEL GENES CODING FOR SMALL TEMPORAL RNAS

(75) Inventors: Thomas Tuschl, New York, NY (US); Mariana Lagos-Quintana, Berlin (DE); Winfried Lendeckel, Hohengandern (DE); Jutta Dammann, Vienna (AT); Reinhard Rauhut, Goettingen (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 13/472,826

(22) Filed: May 16, 2012

(65) Prior Publication Data

US 2013/0245090 A1 Sep. 19, 2013

Related U.S. Application Data

(62) Division of application No. 12/775,947, filed on May 7, 2010, now Pat. No. 8,207,326, which is a division of application No. 11/747,409, filed on May 11, 2007, now Pat. No. 7,723,510, which is a division of application No. 10/490,955, filed as application No. PCT/EP02/10881 on Sep. 27, 2002, now Pat. No. 7,232,806.

(30) Foreign Application Priority Data

Sep. 28, 2001 (EP) ..................................... 01123453
Mar. 22, 2002 (EP) ..................................... 02006712
Jul. 26, 2002 (EP) ..................................... 02016772

(51) Int. Cl.
*C07H 21/02* (2006.01)
*C07H 21/04* (2006.01)
*C12N 15/63* (2006.01)
*C12N 15/113* (2010.01)
*A61K 38/00* (2006.01)

(52) U.S. Cl.
CPC .............. *C12N 15/113* (2013.01); *A61K 38/00* (2013.01); *C12N 2310/14* (2013.01); *C12N 2310/53* (2013.01); *C12N 2330/10* (2013.01)

(58) Field of Classification Search
CPC ....... C12Q 1/6837; C12N 15/63; C07H 21/02
See application file for complete search history.

(56) References Cited

U.S. PATENT DOCUMENTS

| | | | |
|---|---|---|---|
| 5,436,141 A | 7/1995 | Miyata | |
| 5,780,269 A | 7/1998 | Inouye | |
| 5,801,154 A | 9/1998 | Baracchini et al. | |
| 5,849,563 A | 12/1998 | Miyata | |
| 5,861,310 A | 1/1999 | Freeman et al. | |
| 6,207,373 B1 | 3/2001 | Sosnowski | |
| 6,506,559 B1 | 1/2003 | Fire et al. | |
| 6,821,724 B1 | 11/2004 | Mittman et al. | |
| 6,905,827 B2 | 6/2005 | Wohlgemuth | |
| 7,919,245 B2 | 4/2011 | Brown et al. | |
| 8,173,611 B2 | 5/2012 | Brown et al. | |

FOREIGN PATENT DOCUMENTS

| | | |
|---|---|---|
| WO | 9938972 | 8/1999 |
| WO | 9938972 A2 | 8/1999 |
| WO | 02/10449 A2 | 2/2002 |
| WO | 2005/118806 | 12/2005 |

OTHER PUBLICATIONS

Yi et al.: "A skin microRNA promotes differentiation repressing 'stemness'", Nature, vol. 452, No. 7184, pp. 225-230 with supplementary information pp. 1-11, 2008.
Bueno et al.: "Genetic and Epigenetic Silencing of MicroRNA- 203 Enhances ABL1 and BCR- ABL1 Oncogene Expression", Cancer Cell, vol. 13, No. 6, pp. 496-506 with supplemental data pp. 1-10, 2008.
Najafi-Shoushtari et al.: "MicroRNA-33 and the SREBP host genes cooperate to control cholesterol homeostasis", Science, vol. 328, No. 5985, pp. 1566-1569, 2010.
Rayner et al.: "rniR-33 contributes to the regulation of cholesterol homeostasis", Science, vol. 328, No. 5985, pp. 1570-1573, 2010.
Schetter et al.: "MicroRNA expression profiles associated with prognosis and therapeutic outcome in colon adenocarcinoma", JAMA, vol. 299, pp. 425-436, 2008.
Slaby et al.: "Altered expression of miR-21, miR-31, miR-143 and miR-145 is related to clinicopathologic features of colorectal cancer", Oncology, vol. 72, pp. 397-402, 2007.
Qian et al.: "High miR-21 expression in breast cancer associated with poor disease-free survival in early stage disease and high TGF-beta1", Breast Cancer Res Treat, vol. 117, pp. 131-140, 2009.
Yan et al.: "MicroRNA miR-21 overexpression in human breast cancer is associated with advanced clinical stage, lymph node metastasis and patient poor prognosis", RNA, vol. 14, pp. 2348-2360, 2008.
Markou et al.: "Prognostic value of mature microRNA-21 and microRNA-205 overexpression in non-small cell lung cancer by quantitative real-time RT-PCR", Clin Chem, vol. 54, pp. 1696-1704, 2008.
Chan et al.: "miR-21 microRNA expression in human gastric carcinomas and its clinical association", Anticancer Res, vol. 28, pp. 907-911, 2008.

(Continued)

*Primary Examiner* — Amy Bowman
(74) *Attorney, Agent, or Firm* — Rothwell, Figg, Ernst & Manbeck, P.C.

(57) ABSTRACT

In *Caenorhabditis elegans*, lin-4 and let-7 encode 22- and 21-nucleotide RNAs, respectively, that function as key regulators of developmental timing. Because the appearance of these short RNAs is regulated during development, they are also referred to as "small temporal RNAs" (stRNAs). We show that many more 21- and 22-nt expressed RNAs, termed microRNAs, (miRNAs), exist in invertebrates and vertebrates, and that some of these novel RNAs, similar to let-7 stRAN, are also highly conserved. This suggests that sequence-specific post-transcriptional regulatory mechanisms mediated by small RNAs are more general than previously appreciated.

24 Claims, 59 Drawing Sheets

(56) References Cited

OTHER PUBLICATIONS

Figure 1B:
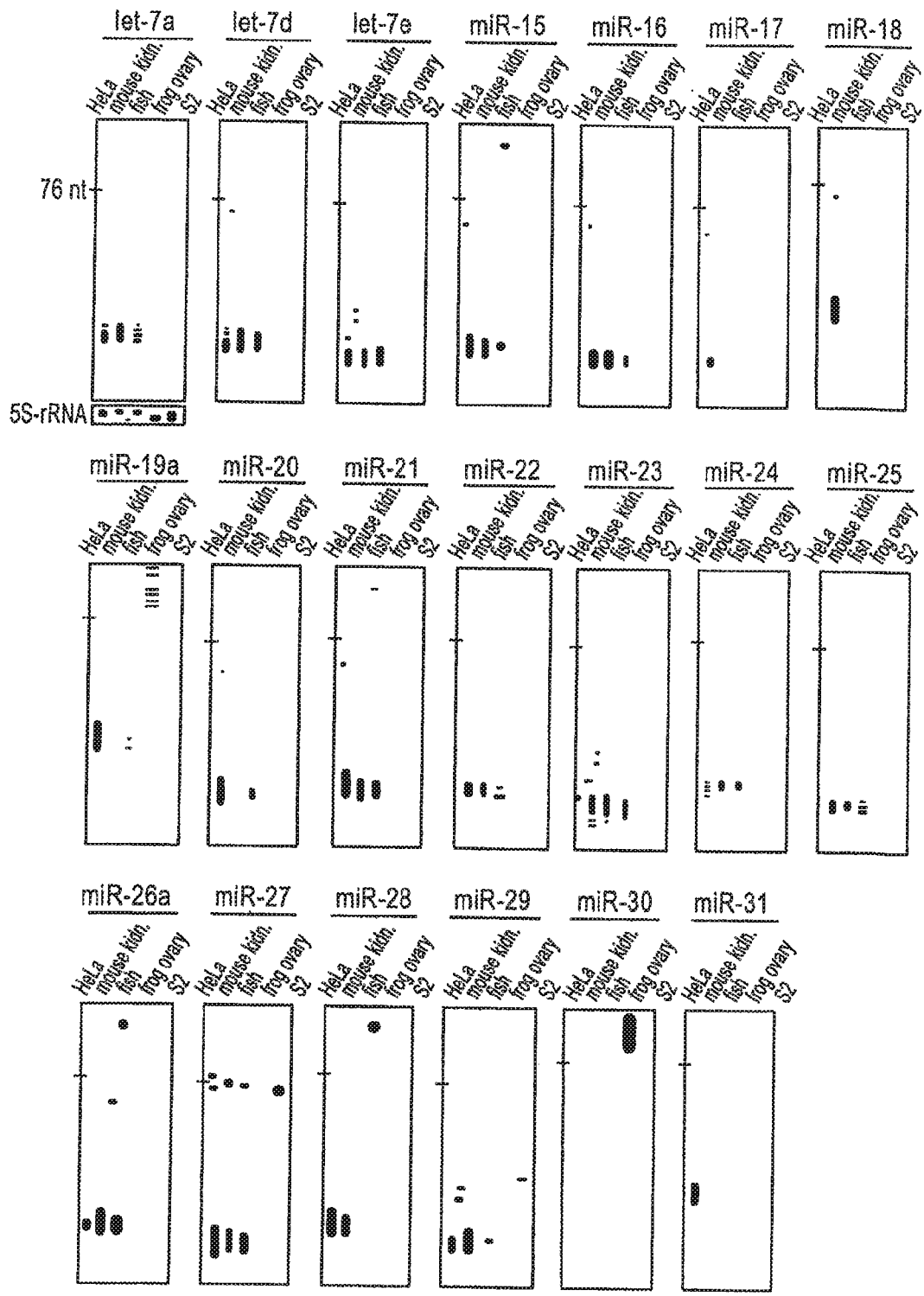

Gabriely et al.: "MicroRNA 21 promotes glioma invasion by targeting matrix metalloproteinase regulators", Mol Cell Biol, vol. 28, pp. 5369-5380, 2008.
Cordes et al.: "miR-145 and miR- 143 regulate smooth muscle cell fate decisions", Nature, vol. 460, No. 7256, pp. 705-710, 2009.
O'Connell et al.: "microRNA-155 promotes autoimmune inflammation by enhancing inflammatory T cell development", Immunity, vol. 33, No. 4, pp. 607-619, 2010.
O'Connell et al.: "Sustained expression of microRNA-155 in hematopoietic stem cells causes a myelo proliferative disorder", The Journal of Experimental Medicine, vol. 205, No. 3, pp. 585-594, 2008.
Bhaumik et al.: "Expression of microRNA-146 suppresses NF-KB activity with reduction of metastatic potential in breast cancer cells", Oncogene, vol. 27, No. 42, pp. 5643-5647, 2008.
Labbaye et al.: "The emerging role of MIR-146A in the control of hematopoiesis, immune function and cancer", Journal of Hematology & Oncology, vol. 5, No. 13, 2012.
Jopling et al.: "Modulation of Hepatitis C Virus RNA Abundance by a Liver-Specific MicroRNA", Science, vol. 309, No. 5740, pp. 1577-1581, 2005.
Krutzfeldt et al.: "Silencing of microRNA in vivo with 'antagomirs'", Nature, vol. 438, No. 7068, pp. 685-689, 2005.
Fabian et al.: "Regulation of MRNA Translation and Stability by microRNAs", Annu. Rev. Biochem., vol. 79, pp. 351-379, 2010.
Croce: "Causes and consequences of microRNA dysregulation in cancer", Nature Reviews Genetics, vol. 10, pp. 704-714, 2009.
Kwon et al.: "MicroRNA1 influences cardiac differentiation in *Drosophila* and regulates Notch signaling", Proc. Natl. Acad. Sci., vol. 102, No. 52, pp. 18986-18991, 2005.
Zhao et al.: "Serum response factor regulates a muscle-specific microRNA that targets Hand2 during cardiogenesis", Nature, 03817, doi:10.1038, pp. 1-7, 2005.
Zhao et al.: "Dysregulation of Cardiogenesis, Cardiac Conduction, and Cell Cycle in Mice Lacking miRNA-1-2", Cell, vol. 129, pp. 303-317, 2007.
Liu et al.: "miR-21 targets the tumor suppressor RhoB and regulates proliferation, invasion and apoptosis in colorectal cancer cells", FEBS Letters, vol. 585, pp. 2998-3005, 2011.
Bonci.: "MicroRNA-21 as therapeutic target in cancer and cardiovascular disease.", Recent Pat Cardiovasc Drug Discov, vol. 5, No. 3, pp. 156-161, 2010, (Abstract).
van Rooij et al.: "Searching for MiR-acles in Cardiac Fibrosis", Circ. Res., vol. 104, pp. 138-140, 2009.
Bracken et al.: "A Double-Negative Feedback Loop between ZEB1-SIP1 and the microRNA-200 Family Regulates Epithelial-Mesenchymal Transition", Cancer Research, vol. 68, No. 19, pp. 7846-7854, 2008.
Kong et al.: "miR-200 Regulates PDGF-D-Mediated Epithelial-Mesenchymal Transition, Adhesion, and Invasion of Prostate Cancer Cells", Stem Cells, vol. 27, pp. 1712-1721, 2009.
Hurteau et al.: "Stable expression of miR-200c alone is sufficient to regulate TCF8 (ZEB1) and restore E-cadherin expression", Cell Cycle, vol. 8, No. 13, pp. 2064-2069, 2009.
Adam et al.: "miR-200 Expression Regulates Epithelial-to-Mesenchymal Transition in Bladder Cancer Cells and Reverses Resistance to Epidermal Growth Factor Receptor Therapy", Clin. Cancer Res., vol. 15, No. 16, pp. 5060-5072, 2009.
Garzon et al.: "MicroRNA 29b functions in acute myeloid leukemia", Blood, vol. 114, No. 26, pp. 5331-5341, 2009.
Mott et al.: "mir-29 Regulates Mcl- 1 Protein Expression and Apoptosis", Oncogene, vol. 26, No. 42, pp. 6133-6140, 2007.
Fabbri et al.: "MicroRNA-29 family reverts aberrant methylation in lung cancer by targeting DNA methyltransferases 3A and 3B", PNAS, vol. 104, No. 40, pp. 15805-15810, 2007.
Webster et al: "Regulation of Epidermal Growth Factor Receptor Signaling in Human Cancer Cells by MicroRNA-7", Journal of Biological Chemistry, vol. 284, No. 9, pp. 5731-5741, 2009.

Kefas et al.: "microRNA-7 Inhibits the Epidermal Growth Factor Receptor and the Akt Pathway and is Down-regulated in Glioblastoma", Cancer Res, vol. 68, No. 10, pp. 3566-3572, 2008.
Elia et al.: "The knockout of miR- 143 and -145 alters smooth muscle cell maintenance and vascular homeostasis in mice: correlates with human disease", Cell Death Differ., vol. 16, No. 12, pp. 1590-1598, 2009.
Cheng et al.: "MicroRNA-145, a Novel Smooth Muscle Cell Phenotypic Marker and Modulator, Controls Vascular Neointimal Lesion Formation", Circulation Research, No. 105, pp. 158-166 with supplemental material pp. 1-12, 2009.
Rangrez et al.: "miR-143 and miR- 145: Molecular Keys to Switch the Phenotype of Vascular Smooth Muscle Cells", Circ Cardiovasc Genet, vol. 4, pp. 197-205, 2011.
Printout from www.medjournalarticles.com/ dissertation/3172, MiR-188-5p Suppresseses Tumor Cell Proliferation and Metastasis by Directly Targeting AAC11 in Hepatocellular Carcinoma, 2012, 8 pgs.
Bernstein et al., Role for a bidentate ribonuclease in the initiation step of RNA interference, Jan. 18, 2001, Nature, vol. 409, pp. 363-366. (Abstract).
Elbashir et al., Duplexes of 21-nucleotide RNAs mediate RNA interference in cultured mammalian cells, May 2001, Nature vol. 411, pp. 494-498.
Grishok, A., et al., "Genes and Mechanisms Related to RNA Interference Regulate Expression of the Small Temporal RNAs that Control elegans Developmental Timing," Cell 106:23-34 (Jul. 13, 2001). (Abstract).
Hammond, et al., "An RNA-directed nuclease mediates post-transcriptional gene silencing in *Drosophila* cells," Nature 404:293-296 (Mar. 16, 2000).
Hammond, et al., "Argonaute2, a Link Between Genetic and Biochemical Analyses of RNAi," Science, 293:1146-1150 (Aug. 10, 2001). (Abstract).
Hamilton et al., A species of small antisense RNA in post-transcriptional gene silencing in plants, Oct. 29, 1999, Science, vol. 286, pp. 950-952. (Abstract).
Hutvagner, et al., "A Cellular Function for the RNA-Interference Enzyme Dicer in the Maturation of the let-7 Small Temporal RNA," Science, 293:834-838 (Aug. 3, 2001). (Abstract).
Tabara, H., et al., "The rde-1 Gene, RNA Interference, and Transposon Silencing in *C. elegans*," Cell 99:123-132 (Oct. 15, 1999).
Zamore, P.D., et al., "RNAi Double-Stranded RNA Directs the ATP-Dependent Cleavage of mRNA at 21 to 23 Nucleotide Intervals," Cell, 101(1):25-33, Cell Press, Cambridge, Massachusetts, US (Mar. 31, 2000), XP-002208683.
Ambros et al., "Heterochronic mutants of the nematode *Caenorhabditis elegans*", Science, vol. 226, No. 409-416, 1984.
Ambros, "Control of developmental timing in *Caenorhabditis elegans*", Current Opinion in Genetics & Development, vol. 10, 2000, p. 428-433.
Aravin et al., "Double-stranded RNA-mediated silencing of genomic tandem repeats and transposable elements in the *D. melanogaster* germline", Current Biology, 2001, 11, pp. 1017-1027.
Argaman et al., "Novel small RNA-encoding genes in the intergenic regions of *Escherichia coli*", Current Biology, 2001, 11: pp. 941-950.
Calin et al., "Human microRNA genes are frequently located at fragile sites and genomic regions involved in cancers", PNAS, Mar. 2, 2004, vol. 101, No. 9, pp. 2999-3004.
Chomczynski et al., "Single-Step Method of RNA Isolation by Acid Guanidinium Thiocyanate-Phenol-Chloroform Extraction", Analytical Biochemistry, 162, 1987, pp. 156-159.
Chu et al., "Electroporation for the efficient tranfection of mammalian cells with DNA", Nucleic Acids Research, 1987, 15 (3), Abstract.
Ebby, "Noncoding RNA genes", Current Opinion in Genetics & Development, vol. 9, 1999, (Abstract).
Fagard et al., "AG01, QDE-2, and RDE-1 are related proteins required for post-transcriptional gene silencing in plants, quelling in fungi, and RNA interference in animals", PNAS, Oct. 10, 2000, vol. 97, No. 21, pp. 11650-11654.

(56) References Cited

OTHER PUBLICATIONS

Feinbaum et al., "The Timing of lin-4 RNA Accumulation Controls the Timing of Postembryonic Developmental Events in *Caenorhabditis elegans*", Developmental Biology, 210, (1999), pp. 87-95.
Felgner et al., "Lipofection: A highly efficient, lipid-mediated DNA-transfection procedure", Proc. Natl. Acad. Sci., vol. 84, Nov. 1987, pp. 7413-7417.
Fraley et al., "Introduction of Liposome-encapsulated SV40 DNA into Cells", The Journal of Biological Chemistry, vol. 255, No. 21, Nov. 10, 1980, pp. 10431-10435.
Gauwerky et al., "Activation of MYC in a masked t (8;17) translocation results in an aggressive B-cell Leukemia", Proc. Natl. Acad. Sci., vol. 86, Nov. 1989, pp. 8867-8871.
Graham et al., "A new technique for the assay of infectivity of human adenovirus 5 DNA", vol. 52, Virology, Apr. 1973, p. 456 (Abstract).
Hallam et al., "lin-14 regulates the time of synaptic remodelling in *Caenorhabditis elegans*", Nature, Sep. 3, 1998, 395, pp. 78-82 (Abstract).
Huettenhofer et al., "RNomics: an experimental approach that identifies 201 candidates for novel, small, non-messenger RNAs in mouse", The EMBO Journal, vol. 20, No. 11, 2001, pp. 2943-2953.
Kallioniemi et al., "Detection and mapping of amplified DNA sequences in breast cancer by comparative genomic hybridization", Proc. Natl. Acad. Sci., vol. 91, Mar. 1994, pp. 2156-2160.
Ketting et al., "Dicer functions in RNA interfernce and in synthesis of small RNA involved in developmental timing in *C. elegans*", Genes Dev., 2001, 15; pp. 2654-2659.
Lau et al., "An Abudant Class of Tiny RNAs with Probable Regulatory Roles in *Caenorhabditis elegans*", Science, Oct. 26, 2001, vol. 294, No. 5543, pp. 858-862.
Lee et al., "Fluorobenzamidrazone thrombin inhibitors: Influence of Fluorine on Enhancing Oral Absorption", Bioorganic & Medicinal Chemistry Letters, 9 (1999), pp. 2483-2486.
Matthews et al., "Expanded sequence dependence of thermodynamic parameters improves prediction of RNA secondary structure", 288, 1999, p. 911.
McCutchan et al, Enhancement of the Infectivity of Simian Virus 40 Deoxyribonucleic Acid with Diethylaminoethyl-Dextran2, JNCI J Natl Cancer Inst (1968) 41, (2), pp. 351-357.
Meng et al., "miR-194 is a Marker of Hepatic Epithelial Cells and Suppresses Metastasis of Liver Cancer Cells in Mice", Haptology, vol. 52, No. 6, 2010, pp. 2148-2157.
Monni et al., "Comprehensive copy number and gene expression profiling of the 17q23 amplicon in human breast cancer", PNAS, May 8, 2001, vol. 98, No. 10, pp. 5711-5716.
Moss, "Non-coding RNAs: Lightning strikes twice", Current Biology, 2000, 10, pp. R436-R439.
Mourelatos et al., "miRNPs: a novel class of ribonucleoproteins containing numerous microRNAs", Genes Dev., 2002, 16: pp. 720-728.
Rougvie, "Control of developmental timing in animals", Nature Reviews Genetics, Sep. 2001, 2, pp. 690-701.
Schneider et al., "Cell lines derived from late embryonic stages of *Drosophila melanogaster*", J. Embryol. Exp. Morph., 1972, vol. 27, 2, pp. 353-365.
Slack et al., "Temporal Pattern Formation by Heterochromic Genes", Genetics, vol. 1, 1997, Abstract.
Tam, "Identification and characterization of human BIC, a gene on chromosome 21, that encodes a noncoding RNA", Gene, 274, 2001, Abstract.
Wassarman et al., "Identification of novel small RNAs using comparative genomics and microarrays", Genes & Development, 15, 2001, pp. 1637-1651.
Wightman et al., "Posttranscriptional Regulation of the Heterochronic Gene lin-14 by lin-4 Mediates Temporal Pattern Formation in *C. elegans*", Cell, vol. 75, Dec. 3, 1993, pp. 855-862.
Wu et al., "17q23 Amplifications in Breast Cancer Involve the PAT1, RAD51C, PS6K, and SIGMA1B Genes", Cancer Res., 2000, 60: pp. 5371-5375.
Capecchi et al., "High Efficiency Transformation by Direct Microinjection of DNA into Cultured Mammalian Cells", Cell, vol. 22, Nov. 1980, pp. 479-488.
Catalanotto et al, "Gene Silencing in worms and fungi", Nature, vol. 404, Mar. 16, 2000, p. 245.
Cavaille et al., "Identificaton of brain-specific and imprinted small nucleolar RNA genes exhibiting an unusual genomic organization", PNAS, vol. 97, No. 26, Dec. 19, 2000, pp. 14311-14316.
Wu et al.: „Suppression of cell growth and invasion by rniR-205 in breast cancer, Cell Research, vol. 19, 2009, pp. 439-448.
Iorio et al.: „MicroRNA Signatures in Human Ovarian Cancer,Cancer Research, vol. 67, No. 18, 2007, pp. 8699-8707.
Calin et al.: "Frequent deletions and down-regulation of microRNA genes miR15 and miR16 at 13q14 in chronic lymphocytic leukemia", PNAS, vol. 99, No. 24, Nov. 26, 2002, pp. 15524-15529.
Chan et al.: "MicroRNA-21 is an antiapoptotic factor in human glioblastoma cells", Cancer Research, No. 65, vol. 14, Jul. 15, 2005, pp. 6029-6033.
Kulshreshtha et al.: "A MicroRNA Signature of Hypoxia", Molecular and Cellular Biology, No. 27, 2007, pp. 1859-1867.
Van Rooij et al.: "Dysregulation of rnicroRNAs after myocardial infarction reveals a role of rniR-29 in cardiac fibrosis", PNAS, vol. 105, No. 35, Sep. 2, 2008, pp. 13027-13032.
Database Geneseq [Online] Aug. 8, 1996 S. Mutants antigen I/II (aa1024-1044) DNA., retrieved from EBI accession No. GSN:AAT36119, Database accession No. AAT36119.
Database Geneseq [Online] Aug. 2, 2001 Human cardiovascular system antigen genomic DNA SEQ ID No. 1605., retrieved from EBI accession No. GSN:AAS36105, Database accession No. AAS36105.
Database Geneseq [Online] Apr. 19, 2001 "Tobacco rpL34 promoter region.", retrieved from EBI accession No. GSN:AAH19667, Database accession No. AAH19667.
Database Geneseq [Online] Aug. 9, 2001 "Human immune/haernatopoietic antigen genomic sequence SEQ ID No. 34996.", retrieved from EBI accession No. GSN:AAK80184, Database accession No. AAK80184.
Kusenda et al.: „MicroRNA Biogenesis, Functionality and Cancer Relevance, Biorned Pap Med Fac Univ Palacky Olomouc Czech Repub., vol. 150, No. 2, 2006, pp. 205-215.
Cheng et al.: „Antisense inhibition of human rniRNAs and indications for an involvement of rniRNA in cell growth and apoptosis, Nucleic Acids 2005 Researc1290-1297h, vol. 33, No. 4 pp. 1290-1297.
Wang et al.: „Prostate apoptosis response protein 4 sensitizes human colon cancer cel,s to chemotherapeutic 5-FU through mediation of an NFKB and microRNA network, Molecular Cancer, vol. 9, No. 98, 2010, pp. 1-19.
Wahlestedt et al., "Potent and nontoxic antisense oligonucleotides containing locked nucleic acids", PNAS, 2000, vol. 97, No. 10, pp. 5633-5638.
DATABASE Geneseq [Online] Jul. 15, 2002, "Human spliced transcript detection oligonucleotide SEQ ID No. 7641.", XP002671443, retrieved from EBI accession No. GSN:ABN34893 Database accession No. ABN34893.
DATABASE Geneseq [Online] Jun. 24, 2002, "Human ORFX polynucleotide sequence SEQ ID No. 19021.", XP002671444, retrieved from EBI accession No. GSN:ABN25272 Database accession No. ABN25272.
DATABASE Geneseq [Online] Feb. 13, 2002, "DNA encoding novel human diagnostic protein #421.", XP002671445, retrieved from EBI accession No. GSN:AAS64617 Database accession No. AAS64617.
Ambros V: "microRNAs: Tiny Regulators with Great Potential" Cell, Cell Press, Cambridge, NA, US LNKD DOI:10.1016/S0092-8674(01)00616-X, vol. 107, Dec. 28, 2001, pp. 823-826, XP002978397 ISSN: 0092-8674.
DATABASE EMBL [Online] Oct. 20, 2000, "CM1-HT0877-190900-426-b01 HT0877 *Homo sapiens* cDNA, mRNA sequence." XP002591547 retrieved from EBI accession No. EMBL:BF088470 Database accession No. BF088470.
DATABASE Geneseq [Online] Jun. 26, 2001, "Human cDNA sequence SEQ ID No. 13278." XP002591548 retrieved from EBI accession No. GSN:AAH15188, Database accession No. AAH15188.

(56) References Cited

OTHER PUBLICATIONS

DATABASE Geneseq [Online] Aug. 8, 1996 "*S. mutans* antigen I/II (aa1024-1044) DNA.", XP002659848, retrieved from EBI accession No. GSN:AAT36119 Database accession No. AAT36119.
DATABASE Geneseq [Online] D, Aug. 2, 2001, "Human cardiovascular system antigen genomic DNA SEQ ID No. 1605.", XP002659849, retrieved from EBI accession No. GSN:AAS36105 Database accession No. AA536105.
DATABASE Geneseq [Online] Aug. 2, 2001,Human reproductive system related antigen DNA SEQ ID No. 5635. 11,XP002668053,retrieved from EBI accession No. GSN:AAL02947 Database accession No. AAL02947.
DATABASE Geneseq [Online] Feb. 7, 2002, "Human spliced transcript detection oligonucleotide SEQ ID No. 5959.", XP002668054,retrieved from EBI accession No. GSN:ABN33211 Database accession No. ABN33211.
DATABASE Geneseq [Online] Sep. 13, 2001, "Novel human)diagnostic and therapeutic gene #2158.", XP002668055, retrieved from EBI accession No. GSN:AAS39100 Database accession No. AAS39100.
DATABASE Geneseq [Online] Aug. 9, 2001, "Probe #3307 used to measure gene expression in human breast sample.", XP002668109, retrieved from EBI accession No. GSN:AAI03316 Database accession No. AAI03316.
DATABASE Geneseq [Online] Aug. 9, 2001, "Human brain expressed single exon probe SEQ ID No. 3386.", XP002668176, retrieved from EBI accession No. GSN:AAK03395 Database accession No. AAK03395.
DATABASE Geneseq [Online] Aug. 9, 2001, "Probe #14654 for gene expression analysis in human heart cell sample.", XP002668111, retrieved from EBI accession No. GSN:ABA36188 Database accession No. ABA36188.
DATABASE Geneseq [Online] Aug. 5, 1999, "Human gene expression product cDNA sequence SEQ ID No. 1651.", XP002668167, retrieved from EBI accession No. GSN:AAZ14182 Database accession No. AAZ14182.
DATABASE Geneseq [Online] Aug. 5, 1999, "Human gene expression product cDNA sequence SEQ ID No. 5028.", XP002668168, retrieved from EBI accession No. GSN:AAZ17555 Database accession No. AAZ17555.
DATABASE Geneseq [Online] May 10, 2001, "Gene expression profile sequence #181.", XP002668169, retrieved from EBI accession No. GSN:AASO4681 Database accession No. AASO4681.
DATABASE Geneseq [Online] Aug. 2, 2001, "Human EST-derived coding sequence SEQ ID No. 908.", XP002668164, retrieved from EBI accession No. GSN:AAH99051 Database accession No. AAH99051.
DATABASE Geneseq [Online] Oct. 11, 2001, "DNA encoding novel human diagnostic protein #4753.", XP002668165, retrieved from EBI accession No. GSN:AAS68949 Database accession No. AAS68949.
DATABASE Geneseq [Online] Jul. 28, 1993, "HIV-1 gag gene branched probe strand 2 forms structure 1.", XP002668166, retrieved from EBI accession No. GSN:AAQ54102 Database accession No. AAQ54102.
DATABASE Geneseq [Online] R 4 Sep. 27, 2001, "*Drosophila melanogaster* genomic polynucleotide SEQ ID No. 10495.", XP002668047, retrieved from EBI accession No. GSN:ABL19674 Database accession No. ABL19674.
DATABASE Geneseq [Online] 2 Sep. 21, 2000, "Human cancer associated gene sequence SEQ ID No. 356.", XP002668268, retrieved from EBI accession No. GSN:AAC77962 Database accession No. AAC77962.
DATABASE Geneseq [Online] R6 Aug. 6, 1998, "LM609 antibody light chain variable region DNA fragment.", XP002668049, retrieved from EBI accession No. GSN:AAV49823 Database accession No. AAV49823.
DATABASE Geneseq [Online] Sep. 27, 2001, "*Drosophila melanogaster* genomic polynucleotide SEQ ID No. 10495.", XP002668047, retrieved from EBI accession No. GSN:ABL19674 Database accession No. ABL19674.
DATABASE Geneseq [Online] Sep. 21, 2000, "Human cancer associated gene sequence SEQ ID No. 356.", XP002668268, retrieved from EBI accession No. GSN:AAC77962 Database accession No. AAC77962.
DATABASE Geneseq [Online] Aug. 6, 1998, "LM609 antibody light chain variable region DNA fragment.", XP002668049, retrieved from EBI accession No. GSN:AAV49823 Database accession No. AAV49823.
DATABASE.Geneseq [Online] Dec. 15, 1982, "Partial RNA sequence corresponding to cattle pre-somatotropin.", XP002659796, retrieved from EBI accession No. GSN:AAN20038 Database accession No. AAN20038.
DATABASE GENESEQ [Online] Jan. 25, 2001, "Mouse glycosyl sulfotransferase-6 (GST-6) genomic DNA.", XP002659797, retrieved from EBI accession No. GSN:AAD02705 Database accession No. AAD02705.
DATABASE Geneseq [Online] Aug. 2, 2001, "Human cardiovascular system antigen genomic DNA SEQ ID No. 2411.", XP002659798, retrieved from EBI accession No. GSN:AAS36911 Database accession No. AAS36911.
DATABASE Geneseq [Online] Feb. 7, 2002, "Mouse spliced transcript detection oligonucleotide SEQ ID No. 24151.", XP002659630, retrieved from EBI accession No. GSN:ABN51403 Database accession No. ABN51403.
DATABASE Geneseq [Online] Aug. 9, 2001, "Human immune/ haematopoietic antigen encoding cDNA SEQ ID No. 9362.", XP002659777, retrieved from EBI accession No. GSN:AAK64302 Database accession No. AAK64302.
DATABASE Geneseq [Online] Oct. 23, 1997, "*Streptococcus pneumoniae* leucyl tRNA synthetase gene.", ../ XP002659778, retrieved from EBI accession No. GSN:AAT88991 Database accession No. AAT88991.
DATABASE Geneseq [Online] Jul. 5, 2001, "Human SNP oligonucleotide #288.", XP002659790, retrieved from EBI accession No. GSN:AAL27080 Database accession No. AAL27080.
DATABASE Geneseq [Online] Aug. 9, 2001, "Human immune/ haematopoietic antigen genomic sequence SEQ ID No. 22901.", XP002659791, retrieved from EBI accession No. GSN:AAK68089 Database accession No. AAK68089.
DATABASE Geneseq [Online] Oct. 28, 1999, "*D. pteronyssius* 98 kD mite allergen gene nDerp98-1470 complement.", XP002659792, retrieved from EBI accession No. GSN:AAZ38590 Database accession No. AAZ38590.
DATABASE Geneseq [Online] Aug. 16, 2001, "Human 6-finger VEGF3a/1 DNA constructing oligonucleotide.", XP002659780, retrieved from EBI accession No. GSN:AAD15343 Database accession No. AAD15343.
DATABASE Geneseq [Online] Sep. 27, 2001, "*Drosophila melanogaster* expressed polynucleotide SEQ ID No. 4649.", XP002659781, retrieved from EBI accession No. GSN:ABL03389 Database accession No. ABL03389.
DATABASE Geneseq [Online] Oct. 19, 1995, "Amplification primer BK83.", XP002659793, retrieved from EBI accession No. GSN:AAT08183 Database accession No. AAT08183.
DATABASE Geneseq [Online] Sep. 30, 1999, "Tobacco plant resistance-associated cDNA fragment 81.", XP002659794, retrieved from EBI accession No. GSN:AAZ33756 Database accession No. AAZ33756.
Quintana et al., "Identification of Novel Genes Coding for Small Expressed RNAs", Science, vol. 294, Oct. 26, 2001, pp. 853-858.
Lee et al., "An Extensive Class of Small RNAs in *Caenorhabditis elegans*", Science, vol. 294, Oct. 26, 2001, pp. 862-864.
Elbashir et al., "Functional anatomy of siRNAs for mediating efficient RNAi in *Drosophila melanogaster* embryo lystae", The EMBO Journal, vol. 20, No. 23, pp. 6877-6888, 2001.
*Drosophila melanogaster* sequence (P1 DS08416(D52)), complete sequence; retrieved from Database EMBL Accession No. AC 002442 (Mar. 3, 2000).
Krutzfeldt et al, Strategies to determine the biological function of microRNAs, 2006, Nature Genetics, vol. 37, No. 11, pp. 1163-1165.

(56) References Cited

OTHER PUBLICATIONS

Cullen, RNAi the natural wayy, 2005, Nature Genetics, vol. 37, No. 11, pp. 1163-1165.
Lee et al., The *C. elegans* Heterochronic Gene lin-4 Encodes Small RNAs with Antisense Complementarity to lin-14, 1993, Cell, vol. 75, pp. 843-854.
Marra et al., AA209594, EST Feb. 18, 1997, see search results labeled "20090122_121332_US-11-747-409-88.rst", result #3 in SCPOPE (enclosed in office action).
Pasquinelli et al., "Conservation of the sequence and temporal expression of let-7 heterochronic regulatory RNA", Nature, vol. 408, No. 6808, 2000, pp. 86-89.
Reinhart et al., "The 21-nucleotide let-7 RNA regulates developmental timing in *Caenorhabditis elegans*", Nature, vol. 403, No. 6772, Feb. 24, 2000, pp. 901-906.
Moss et al., "The cold shock domain protien LIN-28 controls developmental timing in *C. elegans* is rgulated by the lin-4 RNA", Cell, vol. 88, No. 5, 1997, pp. 637-646.
GenBank accession No. AE014298, Mar. 15, 2004.
GenBank accession No. AC101777, Nov. 23, 2001.
GenBank accession No. AL392165, Sep. 11, 2001.
GenBank accession No. AL35585, Jul. 25, 2001.
Ambros et al.: "A uniform system for microRNA annotation", RNA, vol. 9, 2003, pp. 277-279.
Farazi et al.: "miRNAs in human cancer", Journal of Pathology, vol. 223, 2011, pp. 102-115.
Teng et al.: "Shhh! Silencing by microRNA-155", Phil. Trans. R. Soc. B, vol. 364, 2009, pp. 631-637.
GenBank accession No. AL355858, Jul. 25, 2001.
Elbashir et al., "RNA interference is mediated by 21-and 22-nucleotide RNAs", Genes & Development, 2001, 15: pp. 188-200.
GenBank accession No. AA208709.1, mu64c06.r1 Soares mouse lymph node NbMLN Mus musculus cDNA clone IMAGE:64417, 1 page, Jan. 29, 1997.
GenBank accession No. BF018533.1, uy62c07.y1 McCarrey Eddy round spermatid Mus musculus cDNA clone IMAGE:3664140, 1 page, Dec. 29, 2000.
GenBank accession No. BE420487.1, SWOvL2CASO9G08SK Onchocerca volvulus L2 larvae cDNA Onchoc SWOvL2CASO9G08 5-, mRNA sequence, 1 page, Jul. 24, 2000.

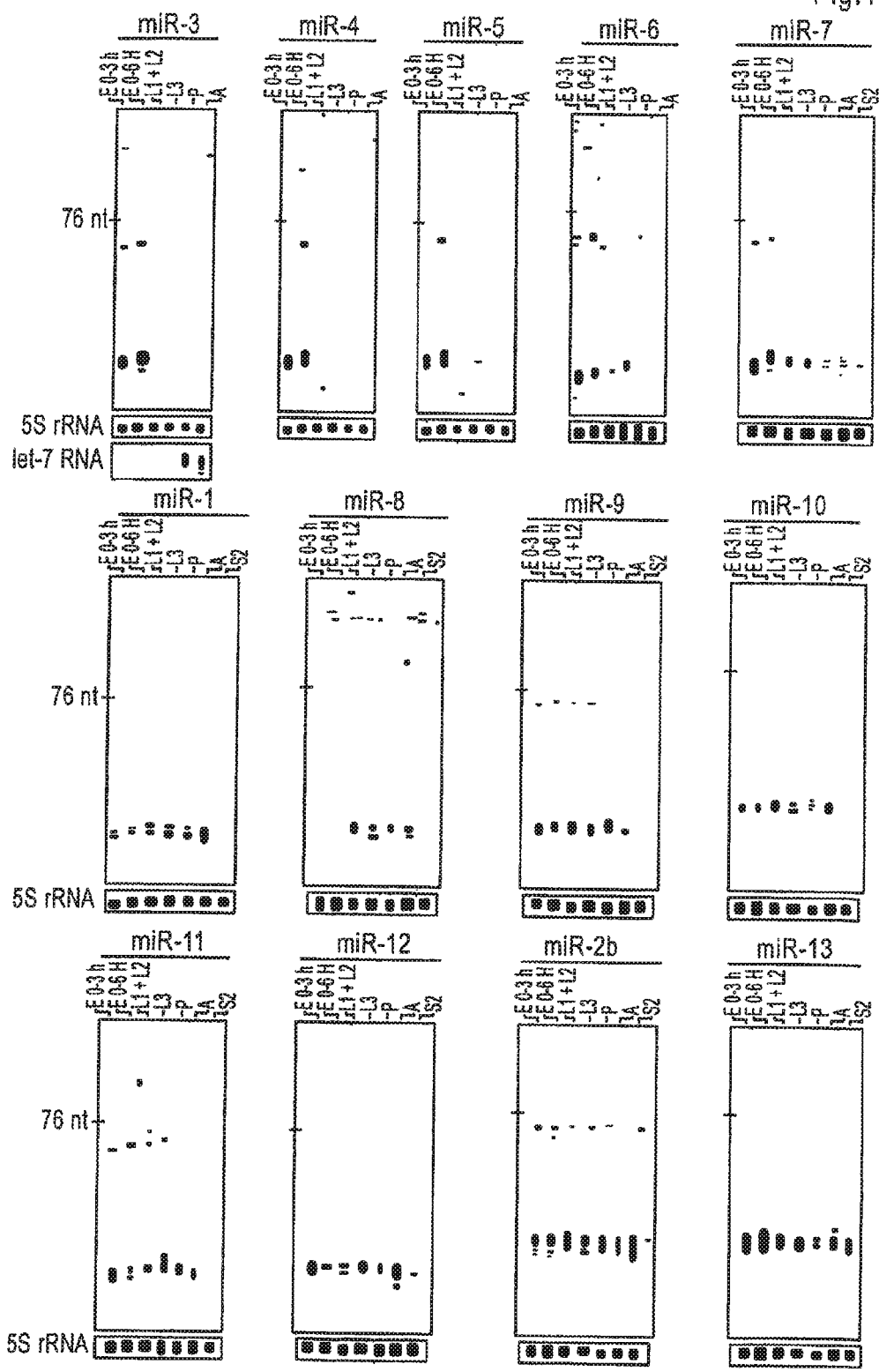

| SEQ ID NO: 414 | *C. elegans* lin-4 | UCCCUGAGACCUC--AAG-UGUGA |
| SEQ ID NO: 415 | *D. melanogaster* miR-125 | UCCCUGAGACCCU--AACUUGUGA |
| SEQ ID NO: 416 | *M. musculus/H. sapiens* miR-125b | UCCCUGAGACCCU--AACUUGUGA |
| SEQ ID NO: 417 | *M. musculus/H. sapiens* miR-125a | UCCCUGAGACCCUUUAACCUGUGA |

B

Fig.7

| name | sequence | structure |
|---|---|---|
| let-7a-1 | UGAGGUAGUAGGUUGUAUAGUU<br>SEQ ID NO: 106 | SEQ ID NO: 271<br>`      UG    U                UUAGG  ACA    C`<br>`CAC  UGGGA GAGGUAGUAGGUUGUAUAGUU   GUC   CCCA C`<br>`GUG  AUCCU UUCUGUCAUCUAACAUAUCAA   UAG   GGGU A`<br>`CA   -                             -----  A--    C` |
| let-7a-2 | UGAGGUAGUAGGUUGUAUAGUU<br>SEQ ID NO: 106 | SEQ ID NO: 272<br>`     UU  G   U              UAGAAUUAC    AA`<br>`AGG  GAG UAG AGGUUGUAUAGUU         AUC  G`<br>`UCC  UUC AUC UCCGACAUGUCAA         UAG  G`<br>`U-       G   C                         AG` |
| let-7a-3 | UGAGGUAGUAGGUUGUAUAGUU<br>SEQ ID NO: 106 | SEQ ID NO: 273<br>`        U                 -----    U`<br>`GGG  GAGGUAGUAGGUUGUAUAGUU   UGGGGC \`<br>`UCC  UUCUGUCAUCUAACAUAUCAA   GUCCCG  C`<br>`   U                       UAGGGUAUC  U` |
| let-7b | UGAGGUAGUAGGUUGUGUGGUU<br>SEQ ID NO: 107 | `GG   U                         - A------  UG`<br>`CGGGG GAGGUAGUAGGUUGUGUGGUU UC         GGGCAG \`<br>`GUCCC UUCCGUCAUCCAACAUAUCAA AG         CCCGUU  A`<br>`--    -                     U  AAGGCUC    GU`<br>SEQ ID NO: 274 |
| let-7c | UGAGGUAGUAGGUUGUAUGGUU<br>SEQ ID NO: 108 | `   A   UU  G   U              UA  G UA AC`<br>`GC UCCGGG GAG UAG AGGUUGUAUGGUU GA U  C  \`<br>`CG AGGUUC UUC AUC UCCAACAUGUCAA UU A  G  C`<br>`         CU   G   U            -- G GG UC`<br>SEQ ID NO: 275 |
| let-7d | AGAGGUAGUAGGUUGCAUAGU<br>SEQ ID NO: 109 | `         A       C    UUA------     GG`<br>`CCUAGGA GAGGUAGUAGGUUG AUAGUU       GGCAG \`<br>`GGAUUCU UUCCGUCGUCCAGC UAUCAA       CCCGUU  A`<br>`       -              A     UGGAGGAACA  UU`<br>SEQ ID NO: 276 |
| let-7e | UGAGGUAGGAGGUUGCAUAGU<br>SEQ ID NO: 110 | `   C  CU  G           U GGA----   A`<br>`CC GGG GAG UAGGAGGUUGUAUAGU GA      GG C`<br>`GG CCC UUC AUCCUCCGGCAUAUCA CU      CC A`<br>`A  CU  G              - AGAGGAA   C`<br>SEQ ID NO: 277 |

Fig.7 (cont)

| | | | |
|---|---|---|---|
| let-7f-1 | UGAGGUAGUAGAUUGUAUAGUU<br>SEQ ID NO: 111 | ```
         AGU                              UG
UCAG      GAGGUAGUAGAUUGUAUAGUUGU     GGGGUAG \
AGUC      UUCCGUUAUCUAACAUAUCAAUA     UCCCAUU  A
  CC-                            GAGGACUUG    UU
``` | SEQ ID NO: 278 |
| let-7f-2 | UGAGGUAGUAGAUUGUAUAGUU<br>SEQ ID NO: 111 | ```
          U                       UCAU
CUGUGGGA GAGGUAGUAGAUUGUAUAGUU   UUAGGG    A \
GGCACCCU UUCUGUCAUCUGACAUAUCAA   GGUUCU    C
                              UAGA    ACCC
``` | SEQ ID NO: 279 |
| let-7g | UGAGGUAGUAGUUUGUACAGUA<br>SEQ ID NO: 112 | ```
      A U     A         UGAGG   A- A     A
CC GGC GAGGUAGU GUUUGUACAGUU     GUCU UG UACC C \
GG CCG UUCCGUCA CGGACAUGUCAA     UAGA AC AUGG C
   A -   C               -----  GG -     C
``` | SEQ ID NO: 280 |
| let-7h | UGAGGUAGUAGUGUGUACAGUU<br>SEQ ID NO: 113 | | |
| let-7i | UGAGGUAGUAGUUUGUGCU<br>SEQ ID NO: 114 | ```
     U GAGGUAGUAGUUUGUGC     U --------- U UGUG
CUGGC GAGGUAGUAGUUUGUGC GUU      GG CGGGU \
GAUCG UUCCGUCAUCGAACGCG CAA      UC GCCCG  A
  -                     U  UAGAGGUG -  UUAC
``` | SEQ ID NO: 281 |
| miR-1 | UGGAAUGUAAAGAAGUAUGGAG<br>SEQ ID NO: 58 | ```
       A  UUUGAGA       C    A  -  AUA
UUC GCC    GUUCCAUGCUUC UUGCAUUC AUA GUU \
GAG CGG    CGAGGUAUGAAG AAUGUAAG UAU CGA  U
  -  UCUAAAG            A    G   A  ACU
``` | SEQ ID NO: 282 |
| miR-1b | UGGAAUGUAAAGAAGUAUGUAA<br>SEQ ID NO: 115 | ```
     A        GC   ---   AC
UGGGA ACAUACUUCUUUAUAU CCAUA UGG \
ACUCU UGUAUGAAGAAAAUGUA GGUAU AUC C
     A-              A-   CGA GU
AL449263.5
``` | SEQ ID NO: 283 |

Fig.7 (cont)

| | | | |
|---|---|---|---|
| miR-1c | UGGAAUGUAAAGAAGUAUGUAC<br>SEQ ID NO: 116 | | |
| miR-1d | UGGAAUGUAAAGAAGUAUGUAUU<br>SEQ ID NO: 117 | ```
           C              GC   UGAACC
GCUUGGGA ACAUACUUCUUUAUAU  CCAUA      U
CGGACUUU UGUAUGAAGAAAUGUA  GGUAU      G
           A              A-   CGAAUC
``` | SEQ ID<br>NO: 284 |
| miR-2a-1 | UAUCACAGCCAGCUUUGAUGAGC<br>SEQ ID NO: 59 | ```
                     A   AUUUC   UU
GCUGGGCUC UCAAAG UGGUUGUGA AUGC    CGC  \
CGAUUCGAG AGUUUC ACCGACACU UACG    GCG  U
          U    G          A       CG
``` | SEQ ID<br>NO: 285 |
| miR-2a-2 | UAUCACAGCCAGCUUUGAUGAGC<br>SEQ ID NO: 59 | ```
     A  C   --            GAUAC
AUCU AGC UCAUCAAG UGGUUGUGAUAUG   \
UAGG UCG AGUAGUUU ACCGACACUAUAC   C
     A  -   CG            GCAAC
``` | SEQ ID<br>NO: 286 |
| miR-2b-1 | UAUCACAGCCAGCUUUGAGGAGC<br>SEQ ID NO: 60 | ```
   U  UG       -  A  C----     U
CU CAAC  UCUUCAAAG UGGC GUGA    AUGUUG C
GG GUUG  AGGAGUUUC ACCG CACU    UAUAAC A
   C  CG      G  A  AUACU     A
``` | SEQ ID<br>NO: 287 |
| miR-2b-2 | UAUCACAGCCAGCUUUGAGGAGC<br>SEQ ID NO: 60 | ```
       A          -      A  UUU-- CUU
UUGUGUC UUCUUCAAAG UGGUUGUGA AUG     GC  U
AGCGCAG GAGGAGUUUC ACCGACACU UAC     CG  U
       C          G      A  UUAUC UAU
``` | SEQ ID<br>NO: 288 |
| miR-3 | UCACUGGGCAAAGUGUGUCUCA<br>SEQ ID NO: 61 | ```
     C       C  G  U  UUCA
GAUC UGGGAUGCAU UUGU CAGU AUGU  \
CUAG ACUCUGUGUG AACG GUCA UACA  A
     A       A  G  C  CUCU
``` | SEQ ID<br>NO: 289 |

Fig.7 (cont)

| | | | |
|---|---|---|---|
| miR-4 | AUAAAGCUAGACAACCAUUGA<br>SEQ ID NO: 62 | ` U   UU  C   C   C  GG    UU`<br>`UUGCAAU AGUUUC UGGU GUC AGC UUA UGAUU  \`<br>`GGUGUUG UUGAAG ACCA CAG UCG AAU ACUGG  U`<br>` C    UU  A   A   A  --    CC` | SEQ ID<br>NO: 280 |
| miR-5 | AAAGGAACGAUCGUUGUGAUAUG<br>SEQ ID NO: 63 | `       UA---     C              AGUUGU`<br>`    GC      AAAGGAA GAUCGUUGUGAUAUG     \`<br>`    CG      UUUCCUU UUAGUGACACUAUAC      U`<br>`      CAAUA        -              AAUCCU` | SEQ ID<br>NO: 281 |
| miR-6-1 | UAUCACAGUGGCUGUUCUUUUU<br>SEQ ID NO: 64 | `      A-            C   AG UAAUA`<br>`   UUUA UGUAGAGGGAAUAGUUGCUGUG UGUA  U    \`<br>`   AAAU AUGUUUUCUUGUCGGUGACAC AUAU  A    U`<br>`      CC            U   CU UACCA` | SEQ ID<br>NO: 282 |
| miR-6-2 | UAUCACAGUGGCUGUUCUUUUU<br>SEQ ID NO: 64 | SEQ ID NO: 283 | `     C     UU UG  C      U - G`<br>`UAACC AAGGGAAC C  CUG UGAUAUA UA UU A`<br>`GUUGG UUUUCUUG G  GAC ACAUAUAU AU AA A`<br>`     U     UC GU  -      C C  A` | |
| miR-6-3 | UAUCACAGUGGCUGUUCUUUUU<br>SEQ ID NO: 64 | SEQ ID NO: 284 | `       A         A    U AAAC`<br>`CAAA AGAAGGGAACGGUUGCUG UGAUGUAG UUG    \`<br>`GUUU UUUUUUCUUGUCGGUGAC ACUAUAUU AAC    /`<br>`   G              -     U ACUC` | |
| miR-7 | UGGAAGACUAGUGAUUUUGUUGU<br>SEQ ID NO: 65 | `         U    U    UU  --         UGGUC`<br>`GAGUGCAU CCGUA GGAAGAC AG GAUUU UGUUGUU  \`<br>`UUUACGUG GGCAU UCUUCUG UC CUAAA ACAAUAA  U`<br>`         C    -    U   C    UA   UGGUU` | SEQ ID<br>NO: 285 |
| miR-8 | UAAUACUGUCAGGUAAAGAUGUC<br>SEQ ID NO: 66 | `       CUGUUC    -    G   C     UCCUUU`<br>`AAGGACAU    ACAUCUU ACC GGCAG AUUAGA     \`<br>`UUCCUGUG    UGUAGAA UGG CUGUC UAAUCU     U`<br>`      CCUGC-     A    A   A     CAAUAU` | SEQ ID<br>NO: 286 |

Fig.7 (cont)

| | | | |
|---|---|---|---|
| miR-9 | UCUUUGUUAUCUAGCUGUAUGA<br>SEQ ID NO: 67 | ``` -    U   UAU    G   - GAU<br>GCUA UGUUG CUUUGGU CUAGCU UAUGA GU   A<br>CGAU AUAAU GAAGCCA GAUCGA AUACU CA   A<br> U    U   UUC    A   G AUA ``` | SEQ ID NO: 297 |
| miR-10 | ACCCUGUAGAUCCGAAUUUGU<br>SEQ ID NO: 68 | ``` CU  - G    U              AUACU<br>CCACGU ACC CU UAGA CCGAAUUGUUUU      A<br>GGUGUG UGG GA AUCU GGCUUAAACAGGA      G<br> UU  A G    U              AUUUC ``` | SEQ ID NO: 298 |
| miR-11 | CAUCACAGUCUGAGUUCUUGC<br>SEQ ID NO: 69 | ``` U    UCU    CCC   U ACU<br>GCACUUG CAAGAACUU  CUGUGA  GCG GU U<br>CGUGAGU GUUCUUGAG  GACACU  CGC CG A<br> C          UCU    A-- -  AAA ``` | SEQ ID NO: 299 |
| miR-12 | UGAGUAUUACAUCAGGUACUGGU<br>SEQ ID NO: 70 | ``` UG  U   C         - GCCUU<br>UACGGU AGUAU ACAU AGGUACUGGU GU   A<br>GUGCCG UCAUA UGUA UUCAUGACCA CA   A<br> CA  C   -         A ACCUA ``` | SEQ ID NO: 300 |
| miR-13a | UAUCACAGCCAUUUGAUGAGU<br>SEQ ID NO: 71 | SEQ ID NO: 301<br>``` U   C   -      A  UC-- CU<br>UACG AACUC UCAAAG GGUUGUGA AUG   GA  A<br>GUGC UUGAG AGUUUU CCGACACU UAC   CU  U<br> U   U   A      A  UCAU AU ``` | |
| miR-13b-1 | UAUCACAGCCAUUUGACGAGU<br>SEQ ID NO: 72 | ``` UG-     U    ACU   UAUU<br>CCA  UCGUUAAAAUG UUGUGA  UAUG   C<br>GGU  AGCAGUUUUAC GACACU  AUAC   A<br> UUG     C    ---   UAAC ``` | SEQ ID NO: 302 |
| miR-13b-2 | UAUCACAGCCAUUUGACGAGU<br>SEQ ID NO: 72 | ``` UAUU  G     A   GCUA    UU<br>AAC CGUCAAAAUG CUGUGA   UGUGGA U<br>UUG GCAGUUUUAC GACACU   AUACUU G<br>GU--  A     C   ----    CA ``` | SEQ ID NO: 303 |

Fig.7 (cont)

| miR-14 | UCAGUCUUUUUCUCUCUCCUA<br>SEQ ID NO: 73 | ```
         C   C       C    GCUU
UGUGGGAG GAGA GGGGACU ACUGU      \
AUAUCCUC CUCU UUUCUGA UGAUA   A
         U   U       C    AAUU
``` | SEQ ID<br>NO: 304 |
|---|---|---|---|
| miR-15a | UAGCAGCACAUAAUGGUUUGUG<br>SEQ ID NO: 119 | ```
     GAGUAAAGUA        UA           GA U
CCUUG          GCAGCACA  AUGGUUUGUG    UUU \
GGAAC          CGUCGUGU  UACCGGACGU    AAA G
     AUAAAACUC        UA           GG  A
``` | SEQ ID<br>NO: 305 |
| miR-15b | UAGCAGCACAUCAUGGUUUACA<br>SEQ ID NO: 120 | ```
    U   C  C      A    A  ACA
CUG AGCAGCA AU AUGGUUU CAU CU    \
GAU UCGUCGU UA UACUAAG GUA GA  G
    C   U  U      C    -  ACU
``` | SEQ ID<br>NO: 306 |
| miR-16 | UAGCAGCACGUAAAUAUUGGCG<br>SEQ ID NO: 121 | ```
SEQ ID  AG  C      UGC UUAGCAGCAC  GU AAUAUUGG      AGAU \
NO:307 CAGUUG  AUG AGUCGUCGUG  CA UUAUGACC     UCUA   A
         GA  A       U  A       -----     UUAA
``` | |
| miR-16 | only different precursor | ```
   UC  CU      UA     C  AG  AAU
GU CACU AGCAGCACG AAUAUUGG GU UGA  A
CA GUGA UCGUCGUGU UUAUAACC CA AUU  U
   GU  UU      CA     A  A-  AUA
``` | SEQ ID<br>NO: 308 |
| miR-17 | ACUGCAGUGAAGGCACUUGU<br>SEQ ID NO: 83 | ```
     GA    CA-     A  G    - AUA
GUCA AUAAUGU AAGUGCUU CA UGCAG UAG UG \
CAGU UAUUACG UUCACGGA GU ACGUC AUC AC  U
     GG    AUG     A  G-    - U GUG
``` | SEQ ID<br>NO: 309 |
| miR-18 | UAAGGUGCAUCUAGUGCAGAUA<br>SEQ ID NO: 84 | ```
     CU  U  C  U   A    UGAA AG
UGUU AAGG GCAU UAG GCAG UAG    GU A
ACGG UUCC CGUG AUC CGUC AUC    CG U
     UC  U  A  C   -    UA-- AU
``` | SEQ ID<br>NO: 310 |

Fig.7 (cont.)

| miRNA | Sequence | Hairpin | SEQ ID |
|---|---|---|---|
| miR-19a | UGUGCAAAUCUAUGCAAAACUGA<br>SEQ ID NO: 85 | ```
        U   U                              AGA
  GCAG CC  CUGUUAGUUUUGCAUAG UUGCAC  UACA \
  CGUC GG  GGUAGUCAAAACGUAUC AACGUG  AUGU  A
        C   U                  UA      UUG   AAG
``` | SEQ ID NO: 311 |
| miR-19b-1 | UGUGCAAAUCCAUGCAAAACUGA<br>SEQ ID NO: 86 | ```
          UU                    --    UC   UGUGU
  CACUG  CUAUGGUUAGUUUUGCA GG UUUGCA  CAGC      \
  GUGAU  GGUGUCAGUCAAAACGU CC AAACGU  GUCG      A
          --                    A  U   --   UCUUAU
``` | SEQ ID NO: 312 |
| miR-19b-2 | UGUGCAAAUCCAUGCAAAACUGA<br>SEQ ID NO: 86 | ```
         CUAC                    --    UUCA     U
  ACAUUG     UUACAAUUAGUUUUGCA GG UUUGCAU  GCGUAUA A
  UGUAAU     AGUGUUAGUCAAAACGU CC AAACGUG  UGUAUAU U
         ----                    A  U   UCGG     G
``` | SEQ ID NO: 313 |
| miR-20 | UAAAGUGCUUAUAGUGCAGGUAG<br>SEQ ID NO: 87 | ```
         C  A-               G    -UU
  GUAG ACU  AAGUGCUUAUAGUGCAG UAG UG  U
  CGUC UGA  UUCACGAGAUAUCGUC  AUC AU  A
         A  AA               -    -U  UG
``` | SEQ ID NO: 314 |
| miR-21 | UAGCUUAUCAGACUGAUGUUGA<br>SEQ ID NO: 88 | ```
                  A   A   A  U AA
  UGUCGGUAGCUUAUC GACUG UGUUG CUGU G \
  ACAGUCUGUCGGGUAG CUGAC ACAAC GGUA C  U
                  C   -    -   UC
``` | SEQ ID NO: 315 |
| miR-22 | AAGCUGCCAGUUGAAGAACUGU<br>SEQ ID NO: 89 | ```
        U  CC              -   A    U  CCUG
  GGC GAG  GCAGUAGUUCUUCAG UGGCA GCUUUA GU    \
  CCG CUC  CGUUGUCAAGAAGUU ACCGU CGAAAU CG    A
        U   C-              G     -  - ACCC
``` | SEQ ID NO: 316 |
| miR-23a | AUCACAUUGCCAGGGAUUUCC<br>SEQ ID NO: 127 | ```
       C   C   -    G   G    CUUC
  GG CGG  UGGGG UUCCUGG GAUG GAUUUG    C
  CC GCC  ACCUU AGGGACC UUAC CUAAAC    U
       A   A   U    G   A    ACUG
``` | SEQ ID NO: 317 |

Fig.7 (cont.)

| miR-23b | AUCACAUUGCCAGGGAUUACCAC SEQ ID NO:128 | ``` 
         C  U  --          -  C   GUGACU
      GG UGC UGG  GUUCCUGGCA UG UGAUUU      U
      CC ACG ACC  UAGGGACCGU AC ACUAAA      G
         A  C  AU          U  -   AUUAGA
``` | SEQ ID NO:318 |
|---|---|---|---|
| miR-24-1 | UGGCUCAGUUCAGCAGGAACAG SEQ ID NO:129 | ```
         G  G  A         UA  UCUCAU
      CUCC GU CCU CUGAGCUGA UCAGU     \
      GAGG CA GGA GACUUGACU GGUCA     U
         A  A  C         C-  CACAUU
``` | SEQ ID NO:319 |
| miR-24-2 | UGGCUCAGUUCAGCAGGAACAG SEQ ID NO:129 | ```
         CC  CG  CU-         AA--   UU
      CUCUG UCC UGC  ACUGAGCUG  ACACAG  \
      GGGAC AGG ACG  UGACUCGGU  UGUGUU  G
         A-  --  ACU          CACA   UG
``` | SEQ ID NO:320 |
| miR-25 | CAUUGCACUUGUCUCGGUCUGA SEQ ID NO:92 | ```
         A   AG  G    UU G   UG  ACG
      GGCC GUGUUG AGGC GAGAC G GCAAU CUGG    C
      CCGG CGUGAC UCUG CUCUG C CGUUA GGUC    U
         C   AG  G    UU A   CG  CCG
``` | SEQ ID NO:321 |
| miR-26a | UUCAAGUAAUCCAGGAUAGGCU SEQ ID NO:93 | ```
         -   G    U      U         GCAG
      AGGCC GUG CCUCGU CAAGUAA CCAGGAUAGGCUGU    G
      UCCGG CGC GGGGCA GUUCAUU GGUUCUAUCCGGUA    U
         G   A    C      -         ACCC
``` | SEQ ID NO:322 |
| miR-26b | UUCAAGUAAUUCAGGAUAGGUU SEQ ID NO:94 | ```
         GA   -   U    UC       UGUG
      CCGG CCC AGU CAAGUAAU AGGAUAGGUUG    \
      GGCC GGG UCG GUUCAUUA UCUUGUCCGAC    C
         AG   C   -    CC       CUGU
``` | SEQ ID NO:323 |
| miR-27a | UUCACAGUGGCUAAGUUCCGCU SEQ ID NO:132 | ```
         A A A          U    G  UCCAC
      CUG GG GC GGGCUUAGCUGCU GUGAGCA GG    \
      GAC CC CG CUUGAAUCGGUGA CACUUGU CU    A
         C C C          -    G  GAACC
``` | SEQ ID NO:324 |

Fig.7 (cont.)

| miR-27b | UUCACAGUGGCUAAGUUCUG<br>SEQ ID NO: 133 | AGGUGCAGAGCUUAGCUG AUUG GUGAACAG UGAU UGG U<br>UCCACGUCUUUGAAUCGGU CACUUGUU GCC U<br>GA-- UC-- U | SEQ ID<br>NO: 325 |
|---|---|---|---|
| miR-28 | AAGGAGCUCACAGUCUAUUGAG<br>SEQ ID NO: 96 | GGU CUUGCCCUC C AGGAGCUCACAGUCUA A UG AGUUA CC U<br>UCA GGACGGGAG UCCUCGAGUGUAGAU AC UCAGU U<br>C G C CCUU CU | SEQ ID<br>NO: 326 |
| miR-29a | CUAGCACCAUCUGAAAUCGGUU<br>SEQ ID NO: 134 | AUGACUGAUUUC UUU UGGUGUU C AGAG UCAAU \<br>UAUUGGCUAAAG ACCACGA UCUU A<br>UCU - UUAAU | SEQ ID<br>NO: 327 |
| miR-29b | UAGCACCAUUUGAAAUCAGUGUU<br>SEQ ID NO: 135 | AGGA A GCUGGUUUCA U AUGGUG GU UUAGAU UUAAAU \<br>UCUU UGACUAAAGU UACCAC GAUCUG A<br>G U -- UUAGUG | SEQ ID<br>NO: 328 |
| miR-29c | UAGCACCAUUUGAAAUCGGuua<br>SEQ ID NO: 136 | | |
| miR-30a-s | UGUAAACAUCCUCGACUGGAAGC<br>SEQ ID NO: 137 | GCG A CUGUAAACAUCC UC GACUGGAAGCU ----- GUG A A \<br>CGU GACGUUUGUAGG CUGACUUUCGG CAC G<br>C -- GUAAA C | SEQ ID<br>NO: 329 |
| miR-30a-as | CUUUCAGUCGGAUGUUUGCAGC<br>SEQ ID NO: 138 | GCG A CUGUAAACAUCC UC GACUGGAAGCU ----- GUG A A \<br>CGU GACGUUUGUAGG CUGACUUUCGG CAC G<br>C -- GUAGA C | SEQ ID<br>NO: 330 |

Fig.7 (cont.)

| miR-30b | UGUAAACAUCCUACACUCAGC<br>SEQ ID NO: 139 | ```
            U -      UCAUA
AUGUAAACAUCC ACA CUCAGCUG    C
UGCAUUUGUAGG UGU GGGUCGGU    A
            - A      UGCGU
``` | SEQ ID NO: 331 |
|---|---|---|---|
| miR-30c | UGUAAACAUCCUACACUCUCAGC<br>SEQ ID NO: 140 | ```
      UACU    U   ACA          GUGGAA
AGA   GUAAACA CCU   CUCUCAGCU       A
UCU   CAUUUGU GGA   GAGGGUCGA       G
      UUCU    C   A--          AAGAAU   human
``` | SEQ ID NO: 332 |
| miR-30d | UGUAAACAUCCCCGACUGGAAG<br>SEQ ID NO: 141 | ```
     U U    CCC          GUAAGA
GU GU GUAAACAUC GACUGGAAGCU      C
CA CG CGUUUGUAG CUGACUUUCGA      A
     U U    A--          AUCGAC   chr8 human
``` | SEQ ID NO: 333 |
| miR-31 | GGCAAGAUGCUGGCAUAGCUG<br>SEQ ID NO: 99 | ```
       GA   G   C      U- GAA
GGAGAG   GGCAA AUG UGGCAUAGC GUU  G
CCUUUC   CCGUU UAC ACCGUAUCG CAA  A
       UA   A   A      UC GGG
``` | SEQ ID NO: 334 |
| miR-32 | UAUUGCACAUUACUAAGUUGC<br>SEQ ID NO: 100 | ```
                 U          - UU C
GGAGAUAUUGCACAU ACUAAGUUGCAU G GU A
CUUUUAUAGUGUGUG UGAUUUAACGUA C CG C
                -          A UC G
``` | SEQ ID NO: 335 |
| miR-33 | GUGCAUUGUAGUUGCAUUG<br>SEQ ID NO: 101 | ```
              A UU         UUCU  UG
CUGUGGUGCAUUGU G GCAUUGCAUG   GG   \
GACACUACGUGACA C UGUAACGUAC   CC   G
              C UU         ----  AU
``` | SEQ ID NO: 336 |
| miR-99a | ACCCGUAGAUCCGAUCUUGU<br>SEQ ID NO: 142 | ```
      A      UC  U    G  AAG
CAUA ACCCGUAGA CGA CUUGUG UG  U
GUGU UGGGUAUCU GCU GAACGC GC  G
      C      UU  C    -  CAG
``` | SEQ ID NO: 337 |

Fig.7 (cont.)

| miR-99b | CACCCGUAGAACCGACCUUGCG<br>SEQ ID NO: 143 | ```
        CC        AC  C  ----    -   C
  GGCAC   ACCCGUAGA   CGA  CU    UGCGG GG \
  CUGUG   UGGGUGUCU   GCU  GA    ACGCC CU  C
        CC        GU  C  ACAC        G  U
``` | SEQ ID NO: 338 |
|---|---|---|---|
| miR-101 | UACAGUACUGUGAUAACUGA<br>SEQ ID NO: 144 | ```
                      A    GUCCA
      UCAGUUAUCACAGUGCUG UGCU     U
      AGUCAAUAGUGUCAUGAC AUGG     U
                      -    AAAUC
``` | SEQ ID NO: 339 |
| miR-122a | UGGAGUGUGACAAUGGUGUUUGU<br>SEQ ID NO: 145 | ```
         GG    C       UGUCC
  AGCUGU   AGUGUGA AAUGGUGUUUG     A
  UCGAUA   UCACACU UUACCGCAAAC     A
         AA    A         UAUCA
``` | SEQ ID NO: 340<br>woodchuck |
| miR-122b | UGGAGUGUGACAAUGGUGUUUGA<br>SEQ ID NO: 146 | | |
| miR-122a,b | UGGAGUGUGACAAUGGUGUUUG<br>SEQ ID NO: 147 | | |
| miR-123 | CAUUAUUACUUUUGGUACGCG<br>SEQ ID NO: 148 | ```
        A  A          U       CGCUG   C
  UGAC GC  CAUUAUUACUU UGGUACG     UGA A
  ACUG CG  GUAAUAAUGAG GCCAUGC     ACU C
        G  C          U       UCAA-   U
``` | SEQ ID NO: 341 |
| miR-124a* | UUAAGGCACGCGGUGAAUGCCA<br>SEQ ID NO: 149 | ```
        -  C     A  GA       UAAUG
  CUCU G  GUGUUCAC GCG  CCUUGAUU     U
  GAGA C  CGUAAGUG CGC  GGAAUUAA     C
        A  -     G  AC       CAUAU
``` | SEQ ID NO: 342 |

Fig.7 (cont.)

| | | | |
|---|---|---|---|
| miR-124b | UUAAGGCACGCGGGUGAAUGC<br>SEQ ID NO: 150 | ```
         CC    A  GA      UAAUG
    CUCU  GUGUUCAC GCG CCUUGAUU    \
    GAGA  CGUAAGUG CGC GGAAUUAA    U
     AC     G   AC      CAUAC   AC021518
``` | SEQ ID NO: 343 |
| miR-125a<br>potential lin-4 ortholog | UCCCUGAGACCCUUUAACCUGUG<br>SEQ ID NO: 151 | ```
          C    C   UA          A
    CUGGGU CCUGAGA CCUU ACCUGUGA  GG C
    GGUCCG GGGUUCU GGAG UGGACACU  CC G
          A    U   --         GGGA U
``` | SEQ ID NO: 344 |
| miR-125b<br>potential lin-4 ortholog | UCCCUGAGACCCUAACUUGUGA<br>SEQ ID NO: 152 | ```
          UC    C   A        GG- U
    GCCUAG CCUGAGA CCU ACUUGUGA UAU U
    CGGAUC GGGUUCU GGA UGAACACU AUG U
          CA    U   C        ACA  A
``` | SEQ ID NO: 345 |
| miR-126 | UCGUACCGUGAGUAAUAAUGC<br>SEQ ID NO: 153 | ```
      A      U      CGCUG  C
    GC CAUUAUUACUU UGGUACG  UGA A
    CG GUAAUAAUGAG GCCAUGC  ACU C
      C      U      UCAA-  U
``` | SEQ ID NO: 346 |
| miR-127 | UCGGAUCCGUCUGAGCUUGGCU<br>SEQ ID NO: 154 | ```
       A U G        G C    -- AG
    CC GCC GCU AAGCUCAGA GG UCUGAU UC \
    GG UGG CGG UUCGAGUCU CC AGGCUA AG A
       C U -        G U    CU AA
``` | SEQ ID NO: 347 |
| miR-128 | UCACAGUGAACCGGUCUCUUUU<br>SEQ ID NO: 155 | ```
         UUC    UAG    CU       U
    GUUGGA GGGGCCG CACUGU GAGAGGU U
    CGACUU CUCUGGC GUGACA CUCUUUA A
         UUU    CAA    --       C
``` | SEQ ID NO: 348 |
| miR-129 | CUUUUUUCGGUCUGGGCUUGC<br>SEQ ID NO: 156 | ```
         -  C CU   G    UUCCU  C
    GGAU CUUUUUG GGU GGGCUU CUG   CU A
    UCUA GAAAAAC CCA CCCGAA GAC   GA A
         U  C UU   G    UGAU-  C  human
``` | SEQ ID NO: 349 |

Fig.7 (cont)

| miR-130 | CAGUGCAAUGUUAAAAGGGC SEQ ID NO: 157 | ```
         -     C           A  GUCUAAC
     GA GCUCUUUU  ACAUUGUGCU CU       \
     CU CGGGAAAA  UGUAACGUGA GA        G
      A        U           C  GCCAUGU
``` | SEQ ID NO: 350 |
|---|---|---|---|
| miR-131 | UAAAGCUAGAUAACCGAAAGU SEQ ID NO: 158 | ```
        G   C              G    U  A
     GUU UUAU UUUGGUUAUCUAGCU UAUGAG GU U
     CAA AAUG AAGCCAAUAGAUCGA AUACUU UG U
        A   A              A    C  G
``` | SEQ ID NO: 351 |
| miR-132 | UAACAGUCUACAGCCAUGGUCGU SEQ ID NO: 159 | ```
         A          UUC      G-  G
     GGGC ACCGUGGCU  GAUUGUUACU UGG \
     CCCG UGGUACCGA  CUGACAAUGG GCC A
         C          CAU      AG  A
``` | SEQ ID NO: 352 |
| miR-133 | UUGGUCCCCUUCAACCAGCUGU SEQ ID NO: 160 | ```
         A   AA U  A      GCCUC
     GCUA AGCUGGU  AA GG ACCAAAUC    U
     CGAU UCGACCA  UU CC UGGUUUAG    U
         G   AC C  C      GUAAC
``` | SEQ ID NO: 353 |
| miR-134 | UGUACUGGUUGACCAGAGGGA SEQ ID NO: 161 | ```
         GU      U A-  G    GCGU  AC
     AGGGU GUGACUGG UG CCA AGGG   GC \
     UCCCA CACUGAUC AC GGU UCCC   UG U
         AC      C CG  G    ACU- UC
``` | SEQ ID NO: 354 |
| miR-135 | UAUGGCUUUUUAUUCCUAUGUGAA SEQ ID NO: 162 | ```
             UU          UUCUAU
     CUAUGGCUUU AUUCCUAUGUGA      \
     GGUGCCGAGG UAGGGAUAUACU       U
             U-          CGCUCG
``` | SEQ ID NO: 355 |
| miR-136 | ACUCCAUUUGUUUUGAUGAUGGA SEQ ID NO: 163 | ```
         C   UUU       UUCU
     GAGGACUC AUUUG  UGAUGAUGGA   \
     CUUCUGAG UAAAC  GCUACUACCU    U
         -    UCU       CGAA
``` | SEQ ID NO: 356 |

Fig.7 (cont)

| miRNA | Sequence | Structure | SEQ ID |
|---|---|---|---|
| miR-137 | UAUUGCUUAAGAAUACGCGUAG<br>SEQ ID NO: 164 | ```
         G  G         A    - GA
CUUCGGU ACG GUAUUCUUGGGUGG UAAUA CG \
GGAGCUG UGC CAUAAGAAUUCGUU AUUGU GC  U
         A  G         -    U AU
``` | SEQ ID NO: 357 |
| miR-138 | AGCUGGUGUUGUGAAUC<br>SEQ ID NO: 165 | ```
        --      UCA     AC-  C  CG
CAGCU GGUGUUGUGAA  GGCCG   GAG AG C
GUUGG CCACAGCACUU  UCGGC   UUC UC A
        GA      UA-     CCA  -  CU
``` | SEQ ID NO: 358 |
| miR-139 | UCUACAGUGCACGUGUCU<br>SEQ ID NO: 166 | ```
     G   -  U A           GUGGC
GU UAUUCUA CAG GC CGUGUCUCCAGU \
CA AUGAGGU GUC CG GCGCAGAGGUCG  U
     -   U  C -           GAGGC
                                human
``` | SEQ ID NO: 359 |
| miR-140 | AGUGGUUUUACCCUAUGGUAG<br>SEQ ID NO: 167 | ```
     -  A            A       UU  UC
CCUG CC GUGGUUUUACCCU UGGUAGG ACG A
GGAC GG CACCAAGAUGGGA ACCAUCU UGU U
     A  -            C       --  CG
``` | SEQ ID NO: 360 |
| miR-141 | AACACUGUCUGGUAAAGAUGG<br>SEQ ID NO: 168 | ```
    U   --  U           AU  GAAG
GGG CCAUCUU CCAG GCAGUGUUGG GGUU \
CCC GGUAGAA GGUC UGUCACAAUC UCGA  U
    -   AU  -           C-  AGUA
``` | SEQ ID NO: 361 |
| miR-142s | CAUAAAGUAGAAAGCACUAC<br>SEQ ID NO: 169 | ```
AC-       A        UAA--- G
   CCAUAAAGUAG AAGCACUAC     CA C
   GGUAUUUCAUC UUUGUGAUG     GU A
GUA       C        UGGGAG C
``` | SEQ ID NO: 362 |
| miR-142as* | UGUAGUGUUUCCUACUUUAUGG<br>SEQ ID NO: 170 | ```
AC-       A        UAA--- G
   CCAUAAAGUAG AAGCACUAC     CA C
   GGUAUUUCAUC UUUGUGAUG     GU A
GUA       C        UGGGAG C
``` | SEQ ID NO: 363 |

Fig.7 (cont)

| Name | Sequence | Structure | SEQ ID |
|---|---|---|---|
| new | AUAAGACGAGCAAAAAGCUUGU<br>SEQ ID NO: 418 | ```
          G       G  C  GG     C  AU
     UGAC GGCGAGCUUUU GC CG UUAUAC UG \
     ACUG UUGUUCGAAAA CG GC AAUAUG AC  G
          G           A  A  AG     C  UC
     AL049829.4
``` | SEQ ID NO: 364 |
| miR-143 | UGAGAUGAAGCACUGUAGCuca<br>UUAGAUGAAGCACUGUAG<br>SEQ ID NO: 171 | ```
            G         G     U  - AG
     CCUGAG UGCAGUGCU CAUCUC GG UC  U \
     GGACUC AUGUCACGA GUAGAG CU AG  U
            G         A     U  G GG
     AC008681.7
``` | SEQ ID NO: 365 |
| miR-144 | UACAGUAUAGAUGAUGUACUAG<br>SEQ ID NO: 172 | ```
            G      A      A- GU
     GGCUGG AUAUCAUC UAUACUGUA GUUU G
     CUGAUC UGUAGUAG AUAUGACAU CAGA A
            A        -        CA  GU
``` | SEQ ID NO: 366 |
| miR-145 | GUCCAGUUUUCCCAGGAAUCCCUU<br>SEQ ID NO: 173 | ```
          C  UC  U  C              UGGAUG
     CUCA GG  CAGU UU CCAGGAAUCCCU       \
     GAGU UC  GUCA AA GGUCCUUAGGGG       C
          -  UU  U  A              UAGAAU
``` | SEQ ID NO: 367 |
| miR-146 | UGAGAACUGAAUUCCAUGGGUUU<br>SEQ ID NO: 174 | ```
          CU         C        AUAUC
     AGCU   GAGAACUGAAUU CAUGGGUU     A
     UCGA   UUCUUGACUUAA GUACCAG      A
          C-          A        ACUGU
``` | SEQ ID NO: 368 |
| miR-147 | GUGUGUGGAAAUGCUUCUGCC<br>SEQ ID NO: 175 | ```
            A-  CAA           ACA---  GA
     AAUCUA  AGA   CAUUUCUGCACAC     CCA \
     UUAGAU  UCU   GUAAAGGUGUGUG     GGU  C
            CG   UC-          ACCGAA   AU   human
``` | SEQ ID NO: 369 |
| miR-148 | UCAGUGCACUACAGAACUUUGU<br>SEQ ID NO: 176 | ```
                       -  A-  CC   -   AGU
     GAGGCAAAGUUCUG AG  CACU  GACU CUG    \
     CUCUGUUUCAAGAC UC  GUGA  CUGA GAU    A
                    A  AC  --   A   AGU   human
``` | SEQ ID NO: 370 |

Fig.7 (cont)

| | | | |
|---|---|---|---|
| miR-149 | UCUGGCUCCGUGUCUUCACUCC<br>SEQ ID NO:177 | ```
         G   C  G   A    GUG   G
GGCUCUG CUC GU UCUUC CUCCC  UUU U
UCGGGGC GAG CA GGAGG GAGGG  GAG C
         G   A  G    -    AG-   C
``` | SEQ ID NO:371 |
| miR-150 | UCUCCCAACCCUUGUACCAGUGU<br>SEQ ID NO:178 | ```
             AC  U   UG-   UG
CCCUGUCUCCCA CCU GUACCAG CUG \
GGGAUAGGGGGU GGA CAUGGUC GAC  C
             CC  -   CCA   UC
``` | SEQ ID NO:372 |
| miR-151 | CUAGACUGAGGCUCCUUGAGGU<br>SEQ ID NO:179 | ```
        C          CA         UGUCU
CCUG CCUCGAGGAGCU CAGUCUAGUA      \
GGAC GGAGUUCCUCGG GUCAGAUCAU      C
     A            A-          CCCUC
``` | SEQ ID NO:373 |
| miR-152 | UCAGUGCAUGACAGAACUUGG<br>SEQ ID NO:180 | ```
                  G  A  CC    CGG   C
CCGGGCCUAGGUUCUGU AU CACU GACU  GCU U
GGCCCGGGUUCAAGACA UA GUGA CUGA  CGA G
                  G  C  --    ---   G
``` | SEQ ID NO:374 |
| miR-153 | UUGCAUAGUCACAAAAGUGA<br>SEQ ID NO:181 | ```
       -         GU    A- AAU
CAGUG UCAUUUUUGUGAU UGCAGCU GU  \
GUAC  AGUGAAAACACUG ACGUUGA CG   A
       U         AU    CC  AGU
``` | SEQ ID NO:375 |
| miR-154 | UAGGUUAUCCGUGUUGCCUUCG<br>SEQ ID NO:182 | ```
           U    -  CCU--    UUU
GAAGAUAGGUUA CCGUGU UG    UCGC  \
UUUUUAUCCAGU GGCACA AC    AGUG   A
           U    U  UAAGC    UUU
``` | SEQ ID NO:376 |
| miR-155<br>[BIC-RNA] | UUAAUGCUAAUUGUGAUAGGGG<br>SEQ ID NO:183 | ```
              U U A       UUGGCC
CUGUUAAUGCUAAU G G UAGGGGUU    \
GACAAUUACGAUUG U C AUCCUCAG     U
              - C -       UCAGUC
``` | SEQ ID NO:377 |

Fig. 7 (cont)

| name | sequence | structure | |
|------|----------|-----------|---|
| miR-C1 | AACAUUCAACGCUGUCGGUGAGU<br>SEQ ID NO: 184 | ```
        U  A   U     CU      A     GGGAUUCA
    CCA GG ACA UCAACG GUCGGUG GUUU          \
    GGU CC UGU AGUUGC CAGCCAC CAAA          A
        U  A   C     --      ~     AAAACAAA
``` | SEQ ID NO: 378 |
| miR-C2 | UUUGGCAAUGGUAGAACUCACA<br>SEQ ID NO: 185 | ```
         UU     UGG    UCA          UAAGGU
    ACCAU UUGGCAA UAGAAC CACCGG      A
    UGGUA AACCGUU AUCUUG GUGGCC      A
         UC     CAG    ---          CAGGGU
``` | SEQ ID NO: 379 |
| miR-C3 | UAUGGCACUGGUAGAAUUCACUG<br>SEQ ID NO: 186 | ```
         G   AC--    GA         --  AC
    CUGU UAUGGC UGGUA AUUCACUG UGA  A
    GACA AUACCG GCCAU UAAGUGAC ACU  G
         A   GGAA    --         UG  CU
``` | SEQ ID NO: 380 |
| miR-C4 | CUUUUUGCGGUCUGGGCUUGUU<br>SEQ ID NO: 187 | ```
         -    C  CU    G   UUUU  C
    UGGAU CUUUUUG GGU GGGCUU CUG    CU G
    AUCUA GAAAAAC CCA CCCGAA GAC    GA A
         U    C  UU    G   UGAU  C
``` | SEQ ID NO: 381 |
| miR-C5 | UGGACGGAGAACUGAUAAGGGU<br>SEQ ID NO: 188 | ```
        U      C    AG    -  UG
    CCU UCCUUAUCA UUUUCC CCAGC UUUG A
    GGA GGGAAUAGU AAGAGG GGUUG GAAU C
        U      C    CA    U  CU
``` | SEQ ID NO: 382 |
| miR-C6 | UGGAGAGAAAGGCAGUUC<br>SEQ ID NO: 189 | ```
                A     G        AU  UC
    AGGGAUUGGAG GAAAG CAGUUCCUG GG  C
    UUCCUGGUCUC CUUUC GUCGGGAC  CC  C
                -     G        --  UC
``` | SEQ ID NO: 383 |

Fig.7 (cont)

| name | sequence | structure | |
|---|---|---|---|
| miR-C7 | CAAAGAAUUCUCCUUUUGGGCUU SEQ ID NO: 190 | ACUUUCCAAAGAAUUC U CCUU UU GGGCUU UCUCAU U<br>UGAAGGGUUUUUUAAG GGAA CCCGAA U<br>U U- UUUUAU | SEQ ID NO: 384 |
| miR-C8 | UCGUGUCUUGUGUUGCAGCCGG SEQ ID NO: 191 | A A C CGCUGC<br>UC GGCU CAACACAGGAC CGGG U<br>GG CCGA GUUGUGUUCUG GCUC C<br>- C U CCCAGU | SEQ ID NO: 385 |
| miR-C9 | UAACACUGUCUGGUAACGAUGU SEQ ID NO: 192 | - C UU UUG<br>GGGCAUC UUACCGGACAGUG UGGA UC \<br>CUUGUAG AAUGGUCUGUCAC AUCU AG G<br>C A C- UUC | SEQ ID NO: 386 |
| miR-C10 | CAUCCCUUGCAUGGUGGAGGGU SEQ ID NO: 193 | CA UC GU UGAGCUC<br>UCU CA CCUUGCAUG GGAGGG U<br>AGG GU GGGACGUAC CCUCCC C<br>AC UU AC CAAAAGU | SEQ ID NO: 387 |
| miR-C11 | GUGCCUACUGAGCUGACAUCAGU SEQ ID NO: 194 | G G A UA UCUCAU<br>CUCC GU CCU CUGAGCUGA UCAGU \<br>GAGG CA GGA GACUUGACU GGUCA U<br>A A C C- CACACU | SEQ ID NO: 388 |
| miR-C12 | UGAUAUGUUUGAUAUAUUAGGU SEQ ID NO: 195 | U- UA--- UU<br>CUGUG GAUAUGUUUGAUAUAU GGUUG \<br>GACAU UUAUACGAACUAUAUA CUAAU A<br>CC UCAAC UU | SEQ ID NO: 389 |

Fig.7 (cont.)

| name | sequence | structure | |
|------|----------|-----------|---|
| miR-C13 | CAACGGAAUCCCAAAAGCAGCU SEQ ID NO: 196 | `       C       C  AA       UU  - C`<br>`AGCGGG  AACGGAAUCC  AA  GCAGCUG  GU CU C`<br>`UCGUCC  UUGCUUUAGG  UU  CGUCGAC  UA GA A`<br>`       C       -  CA       CU  C G` | SEQ ID NO: 390 |
| miR-c14 | CUGACCUAUGAAUUGACA SEQ ID NO: 197 | `     C       -    A      UGCUCUC`<br>`UGACCUAUG AAUUG CAGCCAG        G`<br>`ACUGGAUAC UUAAC GUCGGUC        U`<br>`     -       C    C      UCCCCUC` | SEQ ID NO: 391 |
| miR-C15 | UACCACAGGGUAGAACCACGGA SEQ ID NO: 198 | `   -  G       A     UU  UC`<br>`UCCUG CCG UGGUUUUACCCU UGGUAGG ACG A`<br>`AGGAC GGC ACCAAGAUGGGA ACCAUCU UGU U`<br>`   A  -       C     --  CG` | SEQ ID NO: 392 |
| miR-C16 | AACUGGCCUACAAAGUCCCAG SEQ ID NO: 199 | `   A   U    C    A  A   AGU`<br>`GAG GCUGGG CUUUG GGGC AG UGAG   G`<br>`CUC UGACCC GAAAC UCCG UC ACUU   U`<br>`   C   U    A    G  A   GAC` | SEQ ID NO: 393 |
| miR-C17 | UGUAACAGCAACUCCAUGUGGA SEQ ID NO: 200 | `     U    A      G  --   U`<br>`AUCGGG GUAACAGCA CUCCAU UGGA CUG G`<br>`UAGUCU CAUUGUCGU GAGGUG ACCU GGC C`<br>`     U    C      -  UA   U` | SEQ ID NO: 394 |
| miR-C18 | UAGCAGCACAGAAAUAUUGGC SEQ ID NO: 201 | `     U       A-      UG GAA`<br>`AGCAGCACAG  AAUAUUGGCA  GG    G`<br>`UCGUCGUGUC  UUAUAACCGU  CU    U`<br>`                     GG -- GAG` | SEQ ID NO: 395 |

Fig.7 (cont)

| name | sequence | structure | |
|---|---|---|---|
| miR-C19 | UAGGUAGUUUCAUGUUGUUGG<br>SEQ ID NO: 202 | ```
         A   A    C       GGCCUGGG
GUGAAUU GGU GUUU AUGUUGUUG        U
CACUUAG CCA CAAA UACAACAAC        U
         C   C    U       ACAAGUCU
``` | SEQ ID NO: 396 |
| miR-C20 | UUCACCACCUUCUCCACCCAGC<br>SEQ ID NO: 203 | ```
          C    A     CA    GA  -   A
GGCUGUGC GGGU GAGAGGG GUGG GGU AAG G
CCGGUACG CCCA CUCUUCC CACU CCA UUC C
          A    C     AC    UC  C   U
``` | SEQ ID NO: 397 |
| miR-C21 | GGUCCAGAGGGGAGAUAGG<br>SEQ ID NO: 204 | ```
       G - C G      U  UUCCUG
UCAUU G UC A AGGGGAGA AGG     U
AGUAA U AG U UCUCUUCU UCC     G
       A A A A        - UUUUUA
``` | SEQ ID NO: 398 |
| miR-C22 | CCCAGUGUUCAGACUACCUGUU<br>SEQ ID NO: 205 | ```
    AAC      U       C    G---    G
GCC    CCAGUGU CAGACUAC UGU CA    GAG \
CGG    GGUUACA GUCUGAUG ACA GU    CUC  C
    AUU      C       -    U GUAA  U
``` | SEQ ID NO: 399 |
| miR-C23 | UAAUACUGCCUGGUAAUGAUGAC<br>SEQ ID NO: 206 | ```
      GGC    -      C      UAGUG
GCCGU    CAUC UUACGGGCAG AUUGGA    U
CGGCA    GUAG AAUGGUCCGUC UAAUCU   C
             U          A     CUAGU
``` | SEQ ID NO: 400 |
| miR-C24 | UACUCAGUAAGGCAUUGUUCU<br>SEQ ID NO: 207 | ```
         U   U            UUC   A
UACCUUAC CAG AAGGCAUUGUUC     UAU U
AUGGGAUG GUC UUCCGUGACAAG     AUA U
         U   U            UAA   A
``` | SEQ ID NO: 401 |

Fig.7 (cont)

| name | sequence | structure | |
|---|---|---|---|
| miR-C25 | AGAGGUAUAGCGCAUGGGAAGA<br>SEQ ID NO: 208 | ```
       U             A-           UG     C
  GUUCC  UUUUCCUAGC  UAUACUUCUU  UGGAU  \
  CGAGG  AGAAGGGUACG  AUAUGGAGAA  AUCUG  U
       U             CG           --     G
``` | SEQ ID NO: 402 |
| miR-C26 | UGAAAUGUUUAGGACCACUAG<br>SEQ ID NO: 209 | ```
       C         U     G     A    C U
  GGUC AGUGGUUCU GACA UUCA CAGUU UG \
  CCAG UCACCAGGA UUGU AAGU GUUAA AC A
       A         U     A     -    C G
``` | SEQ ID NO: 403 |
| miR-C27 | UUCCCUUUGUCAUCCUAUGCCUG<br>SEQ ID NO: 210 | ```
       U         A      U    GAGAAUA
  UGGAC UCCCUUUGUC UCCUA GCCU         \
  ACUUG AGGGAAACGG AGGGU CGGA         U
       C          A      -   GGAAGUA
``` | SEQ ID NO: 404 |
| miR-C28 | UCCUUCAUUCCACCGGAGUCUG<br>SEQ ID NO: 211 | ```
       UC         C         UCUUA
  CUCUUG  CUUCAUUCCAC  GGAGUCUG  U
  GAGGAC  GAAGUGAGGUG  CUUUAGAC  G
       UC         A         CAACC
``` | SEQ ID NO: 405 |
| miR-C29 | GUGAAAUGUUUAGGACCACUAGA<br>SEQ ID NO: 212 | ```
      U   C         U     G     A    C U
  GCC GGUC AGUGGUUCU GACA UUCA CAGUU UG \
  CGG CCAG UCACCAGGA UUGU AAGU GUUAA AC A
      C   A         U     A     -    C G
``` | SEQ ID NO: 406 |
| miR-C30 | UGGAAUGUAAGGAAGUGUGUGG<br>SEQ ID NO: 213 | ```
       -                  C U    AUAUC
  CCAGG CCACAUGCUUCUUUAUAU C CAUAG    \
  GGUUU GGUGUGUGAAGGAAUGUA G GUAUC    U
       U                  A -    ACGAC
``` | SEQ ID NO: 407 |

Fig.7 (cont)

| name | sequence | structure | |
|---|---|---|---|
| miR-C31 | UACAGUAGUCUGCACAUUGGUU<br>SEQ ID NO:214 | ```
     AUC      U         C   -------       G
GCC      CCAGUGU CAGACUAC UGU          UCAG A
CGG      GGUUACA GUCGAUG  ACA          GGUC G
     AUU      C         -    UGUACAG       G
``` | SEQ ID NO:408 |
| miR-C32 | CCCUGUAGAACCGAAUUUGUGU<br>a miR-10 variant<br>SEQ ID NO:215 | ```
      A   G    C        UG- AC
UAUAU CCCU UAGAA CGAAUUUGUG  GU  C
AUAUA GGGG AUCUU GCUUAGACAC  UA  C
      A   -    A        UGA CA
``` | SEQ ID NO:409 |
| miR-C33 | AACCCGUAGAUCCGAACUUGUGA<br>A a miR-99a variant<br>SEQ ID NO:216 | ```
      A   C    C   A     C  AU
CACA ACC GUAGAU CGA CUUGUG UG U
GUGU UGG UAUCUG GUU GAACAC AC C
      A   A    U   C     -  GU
``` | SEQ ID NO:410 |
| miR-C34 | GCUUCUCCUGGCUCUCCUCCCUC<br>SEQ ID NO:217 | ```
     C   U    UUG          -    GGAG
AAGG AGGGG GAGGGG   CGGGAGGAGC CGGGC  G
UUCC UCUCC CUCCUC   GUCCUCUUCG GUUCG  C
     -   -    UCG          C    GCGU
``` | SEQ ID NO:411 |

Fig. 7 (cont.)

| name | human | C. elegans | mouse liver | small intes | colon | cerebellum | cortex | midbrain | heart | spleen | Drosophila | fugu fish | zebrafish |
|---|---|---|---|---|---|---|---|---|---|---|---|---|---|
| let-7a-1 | AC007924 chr9 AC087784 chr17 identical precursor | | num.hits in trace date, 3 families of similar precursors | | found | | nearly identical precursor | found | | | | | |
| let-7a-2 | AP001359 chr11 | | | | | | nearly identical precursor | | | | | | |
| let-7a-3 | AL049853 chr22 | AF274345 chrX with diff. precursor | | | | | | | | | AE003659 diff. Precursor | | |
| let-7b | AL049853 chr22 | | nearly identical precursor | | | nearly ident precursor trace#8311003 | | found | | EST AI481799.1 spleen = cerebellum (mammary) | | with slightly diff precursor | |
| let-7c | AP001667 chr21 | | identical and diff. precursors | | | num.genomic hits, ident precursor;diff precursor -> EST AI614897 | numerous genomic hits | found | | | | | |
| let-7d | AC007924.3 chr9 AC087784 chr17 identical | | | | found | trace#8367042 nearly ident prec | trace#8358704 2 nearly ident prec | found | found | | | | |

| | | | | | | | | |
|---|---|---|---|---|---|---|---|---|
| let-7e | AC018755 chr19 | | | | ident precursor genomic DNA | | found | FOUND |
| let-7f-1 | AC007924 chr9 AC087784 chr17 | | | | | found | found | found |
| let-7f-2 | AL592046 chrX | | | | ident. precursor in zmtrace 18713911 | | | |
| let-7g | precursor ident. to mouse in AC092045.2 chr3 | | | | genomic hits, no EST | found | | |
| let-7h | | | | | found in cortex, no db hit | | | |

Fig. 7 (cont.)

Fig.7 (cont.)

| | | | | | | | | |
|---|---|---|---|---|---|---|---|---|
| let-7i | precursor ident. to mouse [AL117383.19]; also AC048341.22 | | found, supported by EST BB661268 | found | | | | |
| miR-1 | | | | | | | 2L,AE003667 | |
| miR-1b | AL449263.5 chr20 nt1-21 | U97405.1 nt 1-21 (22G) | no mouse hit (only nt1-21) | | | found | | |
| miR-1c | | | | | found | | | |
| miR-1d | AL449263.5 chr20 nt1-22 (23G) | | | | found, but no db hit | | | BF157601.1 with C23 (diff. precursor) |
| miR-2a-1 | | | | | trace hits(nt1-23) trace#91 523974 | | 2L,AE003663 | |

Fig. 7 (cont.)

Fig.7 (cont.)

| | | | | | | | | | | | | |
|---|---|---|---|---|---|---|---|---|---|---|---|---|
| miR-5 | | | | | | | | | 2R,AE003795 | | | |
| miR-6-1 | | | | | | | | | 2R,AE003795 | | | |
| miR-6-2 | | | | | | | | | 2R,AE003379 | | | |
| miR-6-3 | | | | | | | | | 2R,AE003379 | | | |
| miR-7 | AC003791 chr19 diff.precursor; EST BF373391 again different | | | | not cloned, but mouse EST predicts precursor similar to human | | | | 2R,AE003791 | | | |
| miR-8 | | | | | | | | | 2R,AE003805 | | | |

| | | | | | | |
|---|---|---|---|---|---|---|
| miR-9 | AC005316 chr15 AC026701 chr5 each with diff. precursor | | | | | |
| miR-10 | AF287967 chr11 (BOX B4/B5) | AF155142.1 chr19 diff prec.sligh.diff prec.s in trace hits | found | | 3L,AE003516 | 2diff precurs scaffold 3868 and 2417 |
| miR-11 | | not found, but AC011194 chr.11 predicts diff. precursor | | | AE001574 | |
| miR-12 | | | | | 3R,AE003735 | |
| miR-13a | | | | | X,AE003499 | |
| | | | | | 3R,AE003708 | |

Fig.7 (cont.)

Fig. 7 (cont.)

| | | | | | | | | | | | |
|---|---|---|---|---|---|---|---|---|---|---|---|
| miR-13b-1 | | | | | | | | | | 3R,AE003708 | |
| miR-13b-2 | | | | | | | | | | X,AE003446 | |
| miR-14 | | | | | | | | | | 2R,AE003833 | |
| miR-15a | 13, AC069475 | | | | | found | trace#72 137197 prec slig diff | | | | |
| miR-15b | | | | | | | trace#79 105069 | | | | |

| | | | | | | | |
|---|---|---|---|---|---|---|---|
| miR-16 | 13, AC069475 interesting leukemia locus | | | | | | AL606727 diff precurs |
| miR-16 | 3, NT_005740.6 | several trace, nearly ident precursor | found | genomic hits with 2 slightly diff precur.trace#502 93836,78368580 | found trace#7910506 9;nearly ident prec. as in human | found | |
| miR-17 | 13, AL138714 | | | | | | |
| miR-18 | 13, AL138714 | | | | | | |
| miR-19a | 13, AL138714 | | | | | found | |
| miR-19b-1 | 13, AL138714 | | | | | | G46757 with a USC |

Fig.7 (cont.)

Fig.7 (cont.)

| | | | | | | | | |
|---|---|---|---|---|---|---|---|---|
| miR-19b-2 | X, AC002407 | | | | | | | |
| miR-20 | 13, AL138714 | | found | | | | | |
| miR-21 | 17, AC004686 | | | AL604063 chr11, near ly ident precursor | found | | | |
| miR-22 | several highly similar ESTs; AW961691 shown | cDNAs from var. tissues, ide ntical precursor | | AK008913 cDNAs, same precursor | AK008913 (cDNA), prec ident to human | | found | |
| miR-23a | 19, AC020916 | | | | | found | found trace#62 540691 prec sli diff | |
| miR-23b | XM_072557.1 chr9, also human ESTs, prec nearly ident to mouse | | | | | EST AW124037 hypothal, EST AI848465 cerebellum | found | three hits in db |

| | | | | | | | |
|---|---|---|---|---|---|---|---|
| miR-24-1 | 9, AF043896 | | | found | | | |
| miR-24-2 | 19, AC020916 | | | | found EST AI286629 (thymus); nearly ident. to miR-24-1; EST AA111466 (whole embryo) different precursor | found | |
| miR-25 | 7, AC073842 second ident. copy found in chr7 | predicted in mouse (EST AI595864), but not cloned | | | | found | G46757 similar precursor |
| miR-26a | 3, AP000497 | | | | AC058818.9,trace# ace#804871973 precursor diff. from human | found | Scaffold_ 4097 different precursor |
| miR-26b | 2, AC021016 | | found | | found,trace#6986, 6494,slight.diff precursor | | |

Fig.7 (cont.)

Fig.7 (cont.)

| | | | | | | | | |
|---|---|---|---|---|---|---|---|---|
| miR-27a | 19, AC020916 | | found | | found, but no db hit | found, but no db hit for mouse | found | found | |
| miR-27b | XM 098843.1 chr9 identical precursor | | | | | found, maps to chr 13 MGSC mmtrace #44671617 | | | |
| miR-28 | 3, AC063932 | | | | | | | | |
| miR-29a | 7, AF017104 second ident.copy found in chr7 CLUSTER, this cluster also consvd in mouse: AC024913.32 | | found, AC024913.32 | found, mmtrace#23467334 | nearly ident precursor trace#2346133 4, EST AC024913.32 | | trace, EST, nearly ident prec | | |
| miR-29b | AL035209.1 chr1 CLUSTER of miR-29-b and 29-c; miRNA similar to miR-83 | | found | | AC024913.32;d iff precursor in EST BC342396 (retina) | AC024913.32;d found | FOUND | | Scaffold 17670.(A third copy) |

| | | | | | | | |
|---|---|---|---|---|---|---|---|
| miR-29c | | | | found | found | found, supported by ESTs | |
| miR-30a-s | nearly ident fold in AL035467.23 chr6 | found;ESTs, trace6802, 3889 all with 22G | | | found | | |
| miR-30a-as | 6, AL035467 | | | | found | | |
| miR-30b | human AF159227.6 chr8,different precursor | | found with diff. precursor in trace #85261735 | trace#7232525l | found | | Scaffold 17670 has two copies of this RNA |
| miR-30c | AL136164.8 chr.6 supported by ESTs (BF594736.1) | | found,but no db hit for mouse | | | found | |
| | | | | | found | found | Scaffold 3483, diff precursor |

Fig. 7 (cont.)

Fig. 7 (cont.)

| | | | | | | | | |
|---|---|---|---|---|---|---|---|---|
| miR-30d | AF159227.5 chr8 | | | | found, but no mouse db hit | | Scaffold 3483, diff fold | |
| miR-31 | 9, AL353732 | | | | | | | |
| miR-32 | 9, AL354797 | | | | | | | |
| miR-33 | 22, Z99716 | | | trace#4891071 | | | | |
| miR-95a | AP000962.2 chr21, ident to mouse; [similar to miR-10 and miR-51] | | mmtrace #92340982 | | | | G44780 with diff.precursor | |
| miR-95b | AC018755.3 chr.19; [similar to miR-10 and miR-51] | | | | | | | |

| | | | | | | | |
|---|---|---|---|---|---|---|---|
| miR-101 | AL158847.17 chr9 diff precursor | | | | AK021368.1 cDNA eyeball | found | U53213.1 T.fluviatilis |
| miR-122a | | abundant but no db hit, except woodchuck x13234 | | | | | |
| miR-122b | | | | | | | |
| miR-122a,b | | | | | | | |
| miR-123 | | genomic hits (trace#6108 147), no EST | | | | | Scaffold 3295 |

Fig.7 (cont.)

Fig. 7 (cont.)

| | | | | | | |
|---|---|---|---|---|---|---|
| miR-124a* | nearly ident. precursor in chr8[AC021518] chr20[AL096828] | found in Z72504.1 chrIV intron,diff precursor | | most abundant in cereb.,genomic hits (trace#21097008, 11737241) | abundant;seve ral trace hits;precurs= cerebellum | found | slightly diff precursor AC009251 chr2L |
| miR-124b | AC021518 chr8,nearly ident chr20 AL096828.29 | | | found, but no db hit | found | | |
| miR-125a | ident precur in AC018755.3 chr 19 | | | genomic hits trace#13921945, 48262259 and more | found | | |
| miR-125b | AP001359.4 chr11 AP001667.1 chr21(chr21 like mouse) | | | | trace#8398570 5 | found with A220 | found in AC006590.1 with diff fold | Scaffold_2358 |
| miR-126 | | | | trace#8521597 and more | | | found | with diff precursSc affold_32 95 |
| miR-127 | human AL117190.6 chr.14 same precurs as in mouse | | | hit in trace#79514537 | | | |

| | | | | | | |
|---|---|---|---|---|---|---|
| miR-128 | ident in AC016742.10 chr 2;diff prec in AC016943.7 chr.3 | | genomic hit trce#51670230 | found | | |
| miR-129 | human AC018662.3 chr7 | | found, but no db hit | | | |
| miR-130 | | | trace 60479278 | | | |
| miR-131 | AC005317.2 chr 15 sligh.diff precursor,but AC026701.6 chr 5 ident | | several trace hits,mouse AF155142 | found | | with diff fold AC091299.2 |
| miR-132 | AL137038.5 chr7 prec sligh.diff from mouse | | trace hit#86984641 | | Scaffold 828,diff prec | |

Fig.7 (cont.)

Fig.7 (cont.)

| | | | | | | | |
|---|---|---|---|---|---|---|---|
| miR-133 | AL391221.15 chr6 diff. Precursor ident to rat (33722.1) | | | | found, trace 62407955 | found | AC093340.1 diff. Precursor | Scaffold 1049;prec n nearly like mouse |
| miR-134 | AL132709.5 chr14 similar precursor | | | | trace16462031 | | | |
| miR-135 | AC092045.2 chr3 AC018659.35 chr2 (ident or simil to mouse) | | | | trace71495235,BSTBF780995.1(kidn.,spleen)(=chr3human) | found | | Scaffold 2125 with similar precurs |
| miR-136 | AL117190.6 chr14 ident to mouse | | | | trace18607175 3 | | | |
| miR-137 | AC027691.1 chr1 ,ident to mouse,nearly ident fish | | | | trace18977454,EST (hypothal)AI852436.1,ident | | | Scaffold 1844 nearly ident to mouse/man |
| miR-138 | AC006058.1 chr3 precursor diff | | | | mouse EST BB528620.2 | | | |

| | | | | | | | | | |
|---|---|---|---|---|---|---|---|---|---|
| miR-139 | AP003065.2 chr11 | | | | found, but no mouse hit | | | | |
| miR-140 | AC026468.8 chr.16,precursor nearly ident. | | several trace hits; trace#1053 0393 | | | | | | |
| miR-141 | AC005512.12 chr12,precursor slightli diff | | AC002397 chr6 | | | | | | |
| miR-142s | AC004687.1 chr17 BCL3/myc translocation locus,like mouse | | found | found | | found | | | |
| miR-142as* | | | several EST AI153235 | found | found | | | | |

Fig.7 (cont.)

Fig.7 (cont.)

| | | | | | | | | | |
|---|---|---|---|---|---|---|---|---|---|
| new | AL049829.4 chr14 | | | | | | found but no db hit | | |
| miR-143 | AC008681.7 chr5 | | | found, but no db hit | | found | | | |
| miR-144 | XM_064366.1 precursor nearly ident | found | | | | | found | | |
| miR-145 | AC008681.7 chr5 GG->GA, precur nearly like mouse, see 2 positions above | | | | | EST AA290206.1, trace 2143909 | | | |
| miR-146 | AC008388.7 chr5 diff precursor | | | | | found EST BF16334B.1 lung | Scaffold 934 similar | | |
| miR-147 | AL592549.7 | | | | | trace#34 639321 | | | |
| | | | | | | found | | | |

| | | | | | | | | | | |
|---|---|---|---|---|---|---|---|---|---|---|
| miR-148 | AC010719.4 | | | | | found, no db hit | | | | |
| miR-149 | | | | | | | | | | |
| miR-150 | | | trace#8472 1065,10352 801 | | | | | | | |
| miR-151 | | | trace#8845 6669 | | trace#85 955550 | | | | | |
| miR-152 | human chr 17 AC004477.1, nearly identical | | found in color,supportd.by trace#8370045;close match MCSC in chr18 (additional MC unlikely, not supported by trace and | | | | | | | |

Fig.7 (cont.)

Fig. 7 (cont.)

| | | | | | | | | | |
|---|---|---|---|---|---|---|---|---|---|
| miR-153 | AC006372.2 chr7 ident.precursor | | | | | | found sever. mmtrace 87010874 | | |
| miR-154 | AL132709.5 chr14 nearly identical precursor | | | | | | found sever. mmtrace 86715639 | | |
| miR-155 (BIC-RNA) | human BIC RNA:AF402776.1 (has U12C) | | found;chr 16 mouse | | | | | | |

Fig.7 (cont.)

| name | human | mouse | | | | | | | Drosophila | fugu fish | zebrafish |
| --- | --- | --- | --- | --- | --- | --- | --- | --- | --- | --- | --- |
| | | spleen | eye | kidney | testes | lung | thymus | skin | | | |
| miR-C1 | with different precursors in chr9 AL158075.11,chr1 AL135321.5 | | mouse trace #76647842 | | | found | | found | | scaffold_1919 | |
| miR-C2 | chr7 AC084864.2 similar precursor | | mouse trace #08841093 | | | | | | | scaffold_967 | AL590150.2 |
| miR-C3 | chr7 AC084864.2 ident.precursor | | trace #86029960 | | | | | | | scaffold_967 | AL590150.2 |
| miR-C4 | similar precursors in chr7 AC018662.3 | | trace #13085686 | | found | | | | | | |
| miR-C5 | chr15 AC069082.9 | | trace #87318220 | | | | | | found | scaffold_3671 | |
| miR-C6 | chr22 AC085664.2 ident.precursor | | chr16 AC012526.32 | | | | | | | | |
| miR-C7 | chr1 AL512843.7 similar prec. | | trace #86694995 | | | | | | | | |

| | | | | | | | | | | |
|---|---|---|---|---|---|---|---|---|---|---|
| miR-C8 | | | found, trace #51673384 | | | | | | | |
| miR-C9 | | | found, trace #78968803 | | | | | scaffold 2210, diff. precursor | | |
| miR-C10 | chrX AY222686.1 nearly ident. precursor | | found, trace #61928192 | | | | | | | |
| miR-C11 | chr9 XM_098943.1 has C17U;prec.nearly identical to mouse | | found, cDNA AI286629.1, has C17U | | | | | | | |
| miR-C12 | | found | found, trace#71 760450 | | | | | scaffold_2294 | | |
| miR-C13 | | | found, trace #88722637 | | | | | | | |

Fig.7 (cont.)

Fig. 7 (cont.)

| name | human | mouse | | | | | | | Drosophila | fuga fish | zebrafish |
| --- | --- | --- | --- | --- | --- | --- | --- | --- | --- | --- | --- |
| | | spleen | eye | kidney | testes | lung | thymus | skin | | | |
| miR-C14 | chr11 AC000159.6 | | | found, but no db hit | | | | | | | |
| miR-C15 | chr16 AC026468.6 nearly ident. precursor | | | EST BI687377.1, several trace | | | | | | scaffold_2083 | |
| miR-C16 | chr17 AC003101.1, similar precursor | | | found, trace#95 55103 | | | | | | scaffold_246 | |
| miR-C17 | chr11 AC000159.6, chr1 AC103590.2; diff. prec. | | | found, trace #87796602 | | | | | | scaffold_152 | |
| miR-C18 | | | | found, trace #47823768 (close to miR-16) | | found | | | | | |
| miR-C19 | chr17 AC009789.21 cloned from human cell line only | | | similar precursor in mouse chr11 AC011194.15 | | | | found | | scaffold_18334 | |
| miR-C20 | chr1 AL355310.19 cloned from human cell line only | | | | | | | | | | |

| | | | | | | | | |
|---|---|---|---|---|---|---|---|---|
| miR-C21 | chr3 AC063952.15 cloned from human cell line only | | | | | | | |
| miR-C22 | chr19 AC007229.1; chr1 AL137157.7 similar precursor; cloned from human cell line only | | | | | scaffold_8399 | | |
| miR-C23 | | | | | trace #72257777 found | scaffold_2210 | | |
| miR-C24 | | | | | trace #69879879 | | | |
| miR-C25 | | | | | trace #49754566 | | | |
| miR-C26 | AL136001 ident. precursor | | | | trace #11977216 | | | |

Fig. 7 (cont.)

Fig.7 (cont.)

| name | human | mouse | | | | | | | Drosophila | fugu fish | zebrafish |
|---|---|---|---|---|---|---|---|---|---|---|---|
| | | spleen | eye | kidney | testes | lung | thymus | skin | | | |
| miR-C27 | chr9 AL159990.12 identical precursor | | trace #91503159 | | | | | | | scaffold_725 | |
| miR-C28 | XM_036612.4, precursor very similar | | | | | | | XM_149012.1 | | scaffold_13664 | |
| miR-C29 | chr14 AL136001.6 nearly identical precursor | | | | | | | trace #18453604 | | | |
| miR-C30 | chr6 AL391221.15 similar precursor | | | | | | | trace #84055510 | | | |
| miR-C31 | chr9 AC006312.8 | | | | | | | trace #89079710 | | scaffold_5030 | |
| miR-C32 | | | | | | | | U77364.1, intronic location Hoxd4 gene | | scaffold_82 | |
| miR-C33 | | | | | | | | trace #84780544 | | scaffold_15612 | |
| miR-C34 | | | | | | | trace# 72109322 | | | | |

SEQUENCE LISTING

<160> NUMBER OF SEQ ID NOS: 418

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 1
tactatacaa cctactacct caatttgcc                                     29

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
actatgcaac ctactacctc t                                             21

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 3
actatacaac ctcctacctc a                                                    21

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 4
tggtgtttcc gcccgggaa                                                       19

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
tggaatgtaa agaagtatgg ag                                                   22

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
gctcctcaaa gctggctgtg ata                                                  23

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
tgagacacac tttgcccagt ga                                                   22

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
tcaatggttg tctagcttta t                                                    21

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
catatcacaa cgatcgttcc ttt                                                  23

<210> SEQ ID NO 10
<211> LENGTH: 22
<212> TYPE: DNA
<213> ORGANISM: Artificial Sequence

```
<220> FEATURE:
<223> OTHER INFORMATION: Synthetic oligonucleotide

<400> SEQUENCE: 10
aaaaagaaca gccactgtga ta                                              22

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 11
tggaagacta gtgattttgt tgt                                             23

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 12
gacatcttta cctgacagta tta                                             23

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 13
tcatacagct agataaccaa aga                                             23

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
acaaattcgg atctacaggg t                                               21

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
gcaagaactc agactgtgat g                                               21

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
accagtacct gatgtaatac tca                                             23
```

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
actcgtcaaa atggctgtga ta                                    22

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
taggagagag aaaaagactg a                                     21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
tagcagcaca taatggtttg t                                     21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
gccaatattt acgtgctgct a                                     21

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
tacaagtgcc ttcactgcag ta                                    22

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
tatctgcact agatgcacct ta                                    22

<210> SEQ ID NO 23
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 23
tcagttttgc atagatttgc aca                                            23

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 24
tacctgcact ataagcactt ta                                             22

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
tcaacatcag tctgataagc ta                                             22

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 26
acagttcttc aactggcagc tt                                             22

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
ggaaatccct ggcaatgtga t                                              21

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28
ctgttcctgc tgaactgagc ca                                             22

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29
tcagaccgag acaagtgcaa tg                                             22

<210> SEQ ID NO 30
```

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 30
agcctatcct ggattacttg aa                                              22

<210> SEQ ID NO 31
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 31
agcggaactt agccactgtg aa                                              22

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32
ctcaatagac tgtgagctcc tt                                              22

<210> SEQ ID NO 33
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 33
aaccgatttc agatggtgct ag                                              22

<210> SEQ ID NO 34
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 34
gctgcaaaca tccgactgaa ag                                              22

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
cagctatgcc agcatcttgc ct                                              22

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
```

-continued

```
gcaacttagt aatgtgcaat a                                              21

<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 37
tgcaatgcaa ctacaatgca cc                                             22

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
ctccatactt ctttacattc ca                                             22

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
gctgagtgta ggatgtttac a                                              21

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 40
gcttccagtc gaggatgttt aca                                            23

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
cgcaaggtcg gttctacggg tg                                             22

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
tcagttatca cagtactgta                                                20

<210> SEQ ID NO 43
<211> LENGTH: 23
<212> TYPE: DNA
```

```
<213> ORGANISM: Artificial Sequence
<220> FEATURE:
<223> OTHER INFORMATION: Synthetic oligonucleotide

<400> SEQUENCE: 43
acaaacacca ttgtcacact cca                                              23

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44
tggcattcac cgcgtgcctt a                                                21

<210> SEQ ID NO 45
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 45
cacaggttaa agggtctcag gga                                              23

<210> SEQ ID NO 46
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 46
tcacaagtta gggtctcagg ga                                               22

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 47
agccaagctc agacggatcc ga                                               22

<210> SEQ ID NO 48
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 48
aaaagagacc ggttcactct ga                                               22

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 49
gcaagcccag accgaaaaaa g                                                21
```

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
gcccttttaa cattgcactc                                               20

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 51
actttcggtt atctagcttt a                                             21

<210> SEQ ID NO 52
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 52
acgaccatgg ctgtagactg tta                                           23

<210> SEQ ID NO 53
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 53
tgagctacag tgcttcatct ca                                            22

<210> SEQ ID NO 54
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' - phosphate
<220> FEATURE:
<221> NAME/KEY: misc_feature
<222> LOCATION: (1)..(3)
<223> OTHER INFORMATION: Bases 1 - 3 are RNA
<220> FEATURE:
<221> NAME/KEY: misc_feature
<222> LOCATION: (18)..(18)
<223> OTHER INFORMATION: 3' - Amino-Modifier C-7

<400> SEQUENCE: 54
uuuaaccgcg aattccag                                                 18

<210> SEQ ID NO 55
<211> LENGTH: 18
<212> TYPE: DNA
<213> ORGANISM: Artificial Sequence
<220> FEATURE:

```
<223> OTHER INFORMATION: Synthetic oligonucleotide
<220> FEATURE:
<221> NAME/KEY: misc_feature
<222> LOCATION: (16)..(18)
<223> OTHER INFORMATION: Bases 16 - 18 are RNA

<400> SEQUENCE: 55
acggaattcc tcactaaa                                                        18

<210> SEQ ID NO 56
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 56
gactagctgg aattcgcggt taaa                                                 24

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 57
cagccaacgg aattcctcac taaa                                                 24

<210> SEQ ID NO 58
<211> LENGTH: 22
<212> TYPE: RNA
<213> ORGANISM: Drosophila melanogaster

<400> SEQUENCE: 58
uggaauguaa agaaguaugg ag                                                   22

<210> SEQ ID NO 59
<211> LENGTH: 23
<212> TYPE: RNA
<213> ORGANISM: Drosophila melanogaster

<400> SEQUENCE: 59
uaucacagcc agcuuugaug agc                                                  23

<210> SEQ ID NO 60
<211> LENGTH: 23
<212> TYPE: RNA
<213> ORGANISM: Drosophila melanogaster

<400> SEQUENCE: 60
uaucacagcc agcuuugagg agc                                                  23

<210> SEQ ID NO 61
<211> LENGTH: 22
<212> TYPE: RNA
<213> ORGANISM: Drosophila melanogaster

<400> SEQUENCE: 61
ucacugggca aagugugucu ca                                                   22

<210> SEQ ID NO 62
<211> LENGTH: 21
<212> TYPE: RNA
<213> ORGANISM: Drosophila melanogaster
```

```
<400> SEQUENCE: 62
auaaagcuag acaaccauug a                                              21

<210> SEQ ID NO 63
<211> LENGTH: 23
<212> TYPE: RNA
<213> ORGANISM: Drosophila melanogaster

<400> SEQUENCE: 63
aaaggaacga ucguugugau aug                                            23

<210> SEQ ID NO 64
<211> LENGTH: 22
<212> TYPE: RNA
<213> ORGANISM: Drosophila melanogaster

<400> SEQUENCE: 64
uaucacagug gcuguucuuu uu                                             22

<210> SEQ ID NO 65
<211> LENGTH: 23
<212> TYPE: RNA
<213> ORGANISM: Drosophila melanogaster

<400> SEQUENCE: 65
uggaagacua gugauuuugu ugu                                            23

<210> SEQ ID NO 66
<211> LENGTH: 23
<212> TYPE: RNA
<213> ORGANISM: Drosophila melanogaster

<400> SEQUENCE: 66
uaauacuguc agguaaagau guc                                            23

<210> SEQ ID NO 67
<211> LENGTH: 23
<212> TYPE: RNA
<213> ORGANISM: Drosophila melanogaster

<400> SEQUENCE: 67
ucuuugguua ucuagcugua uga                                            23

<210> SEQ ID NO 68
<211> LENGTH: 21
<212> TYPE: RNA
<213> ORGANISM: Drosophila melanogaster

<400> SEQUENCE: 68
acccuguaga uccgaauuug u                                              21

<210> SEQ ID NO 69
<211> LENGTH: 21
<212> TYPE: RNA
<213> ORGANISM: Drosophila melanogaster

<400> SEQUENCE: 69
caucacaguc ugaguucuug c                                              21

<210> SEQ ID NO 70
<211> LENGTH: 23
<212> TYPE: RNA
```

```
<213> ORGANISM: Drosophila melanogaster

<400> SEQUENCE: 70
ugaguauuac aucagguacu ggu                                              23

<210> SEQ ID NO 71
<211> LENGTH: 22
<212> TYPE: RNA
<213> ORGANISM: Drosophila melanogaster

<400> SEQUENCE: 71
uaucacagcc auuuugacga gu                                               22

<210> SEQ ID NO 72
<211> LENGTH: 22
<212> TYPE: RNA
<213> ORGANISM: Drosophila melanogaster

<400> SEQUENCE: 72
uaucacagcc auuuugauga gu                                               22

<210> SEQ ID NO 73
<211> LENGTH: 21
<212> TYPE: RNA
<213> ORGANISM: Drosophila melanogaster

<400> SEQUENCE: 73
ucagucuuuu ucucucuccu a                                                21

<210> SEQ ID NO 74
<211> LENGTH: 22
<212> TYPE: RNA
<213> ORGANISM: Drosophila melanogaster

<400> SEQUENCE: 74
ugagguagua gguuguauag uu                                               22

<210> SEQ ID NO 75
<211> LENGTH: 22
<212> TYPE: RNA
<213> ORGANISM: Homo sapiens

<400> SEQUENCE: 75
ugagguagua gguuguauag uu                                               22

<210> SEQ ID NO 76
<211> LENGTH: 22
<212> TYPE: RNA
<213> ORGANISM: Homo sapiens

<400> SEQUENCE: 76
ugagguagua gguugugugg uu                                               22

<210> SEQ ID NO 77
<211> LENGTH: 22
<212> TYPE: RNA
<213> ORGANISM: Homo sapiens

<400> SEQUENCE: 77
ugagguagua gguuguaugg uu                                               22

<210> SEQ ID NO 78
<211> LENGTH: 21
```

```
<212> TYPE: RNA
<213> ORGANISM: Homo sapiens

<400> SEQUENCE: 78
agagguagua gguugcauag u                                        21

<210> SEQ ID NO 79
<211> LENGTH: 21
<212> TYPE: RNA
<213> ORGANISM: Homo sapiens

<400> SEQUENCE: 79
ugagguagga gguuguauag u                                        21

<210> SEQ ID NO 80
<211> LENGTH: 22
<212> TYPE: RNA
<213> ORGANISM: Homo sapiens

<400> SEQUENCE: 80
ugagguagua gauuguauag uu                                       22

<210> SEQ ID NO 81
<211> LENGTH: 22
<212> TYPE: RNA
<213> ORGANISM: Homo sapiens

<400> SEQUENCE: 81
uagcagcaca uaaugguuug ug                                       22

<210> SEQ ID NO 82
<211> LENGTH: 22
<212> TYPE: RNA
<213> ORGANISM: Homo sapiens

<400> SEQUENCE: 82
uagcagcacg uaaauauugg cg                                       22

<210> SEQ ID NO 83
<211> LENGTH: 20
<212> TYPE: RNA
<213> ORGANISM: Homo sapiens

<400> SEQUENCE: 83
acugcaguga aggcacuugu                                          20

<210> SEQ ID NO 84
<211> LENGTH: 22
<212> TYPE: RNA
<213> ORGANISM: Homo sapiens

<400> SEQUENCE: 84
uaaggugcau cuagugcaga ua                                       22

<210> SEQ ID NO 85
<211> LENGTH: 23
<212> TYPE: RNA
<213> ORGANISM: Homo sapiens

<400> SEQUENCE: 85
ugugcaaauc uaugcaaaac uga                                      23

<210> SEQ ID NO 86
```

```
<211> LENGTH: 23
<212> TYPE: RNA
<213> ORGANISM: Homo sapiens

<400> SEQUENCE: 86
ugugcaaauc caugcaaaac uga                                               23

<210> SEQ ID NO 87
<211> LENGTH: 22
<212> TYPE: RNA
<213> ORGANISM: Homo sapiens

<400> SEQUENCE: 87
uaaagugcuu auagugcagg ua                                                22

<210> SEQ ID NO 88
<211> LENGTH: 22
<212> TYPE: RNA
<213> ORGANISM: Homo sapiens

<400> SEQUENCE: 88
uagcuuauca gacugauguu ga                                                22

<210> SEQ ID NO 89
<211> LENGTH: 22
<212> TYPE: RNA
<213> ORGANISM: Homo sapiens

<400> SEQUENCE: 89
aagcugccag uugaagaacu gu                                                22

<210> SEQ ID NO 90
<211> LENGTH: 21
<212> TYPE: RNA
<213> ORGANISM: Homo sapiens

<400> SEQUENCE: 90
aucacauugc cagggauuuc c                                                 21

<210> SEQ ID NO 91
<211> LENGTH: 22
<212> TYPE: RNA
<213> ORGANISM: Homo sapiens

<400> SEQUENCE: 91
uggcucaguu cagcaggaac ag                                                22

<210> SEQ ID NO 92
<211> LENGTH: 22
<212> TYPE: RNA
<213> ORGANISM: Homo sapiens

<400> SEQUENCE: 92
cauugcacuu gucucggucu ga                                                22

<210> SEQ ID NO 93
<211> LENGTH: 22
<212> TYPE: RNA
<213> ORGANISM: Homo sapiens

<400> SEQUENCE: 93
uucaaguaau ccaggauagg cu                                                22
```

```
<210> SEQ ID NO 94
<211> LENGTH: 22
<212> TYPE: RNA
<213> ORGANISM: Homo sapiens

<400> SEQUENCE: 94
uucaaguaau ucaggauagg uu                                              22

<210> SEQ ID NO 95
<211> LENGTH: 22
<212> TYPE: RNA
<213> ORGANISM: Homo sapiens

<400> SEQUENCE: 95
uucacagugg cuaaguuccg cu                                              22

<210> SEQ ID NO 96
<211> LENGTH: 22
<212> TYPE: RNA
<213> ORGANISM: Homo sapiens

<400> SEQUENCE: 96
aaggagcuca cagucuauug ag                                              22

<210> SEQ ID NO 97
<211> LENGTH: 22
<212> TYPE: RNA
<213> ORGANISM: Homo sapiens

<400> SEQUENCE: 97
cuagcaccau cugaaaucgg uu                                              22

<210> SEQ ID NO 98
<211> LENGTH: 22
<212> TYPE: RNA
<213> ORGANISM: Homo sapiens

<400> SEQUENCE: 98
cuuucagucg gauguuugca gc                                              22

<210> SEQ ID NO 99
<211> LENGTH: 21
<212> TYPE: RNA
<213> ORGANISM: Homo sapiens

<400> SEQUENCE: 99
ggcaagaugc uggcauagcu g                                               21

<210> SEQ ID NO 100
<211> LENGTH: 21
<212> TYPE: RNA
<213> ORGANISM: Homo sapiens

<400> SEQUENCE: 100
uauugcacau uacuaaguug c                                               21

<210> SEQ ID NO 101
<211> LENGTH: 19
<212> TYPE: RNA
<213> ORGANISM: Homo sapiens

<400> SEQUENCE: 101
gugcauugua guugcauug                                                  19
```

<210> SEQ ID NO 102
<211> LENGTH: 22
<212> TYPE: RNA
<213> ORGANISM: Homo sapiens

<400> SEQUENCE: 102
uggaauguaa agaaguaugg ag                                    22

<210> SEQ ID NO 103
<211> LENGTH: 23
<212> TYPE: RNA
<213> ORGANISM: Homo sapiens

<400> SEQUENCE: 103
uggaagacua gugauuuugu ugu                                   23

<210> SEQ ID NO 104
<211> LENGTH: 23
<212> TYPE: RNA
<213> ORGANISM: Homo sapiens

<400> SEQUENCE: 104
ucuuugguua ucuagcugua uga                                   23

<210> SEQ ID NO 105
<211> LENGTH: 21
<212> TYPE: RNA
<213> ORGANISM: Homo sapiens

<400> SEQUENCE: 105
acccuguaga uccgaauuug u                                     21

<210> SEQ ID NO 106
<211> LENGTH: 22
<212> TYPE: RNA
<213> ORGANISM: Mus musculus

<400> SEQUENCE: 106
ugagguagua gguuguauag uu                                    22

<210> SEQ ID NO 107
<211> LENGTH: 22
<212> TYPE: RNA
<213> ORGANISM: Mus musculus

<400> SEQUENCE: 107
ugagguagua gguugugugg uu                                    22

<210> SEQ ID NO 108
<211> LENGTH: 22
<212> TYPE: RNA
<213> ORGANISM: Mus musculus

<400> SEQUENCE: 108
ugagguagua gguuguaugg uu                                    22

<210> SEQ ID NO 109
<211> LENGTH: 21
<212> TYPE: RNA
<213> ORGANISM: Mus musculus

<400> SEQUENCE: 109
agagguagua gguugcauag u                                     21

<210> SEQ ID NO 110
<211> LENGTH: 21
<212> TYPE: RNA
<213> ORGANISM: Mus musculus

<400> SEQUENCE: 110
ugagguagga gguuguauag u                                             21

<210> SEQ ID NO 111
<211> LENGTH: 22
<212> TYPE: RNA
<213> ORGANISM: Mus musculus

<400> SEQUENCE: 111
ugagguagua gauuguauag uu                                            22

<210> SEQ ID NO 112
<211> LENGTH: 22
<212> TYPE: RNA
<213> ORGANISM: Mus musculus

<400> SEQUENCE: 112
ugagguagua guuuguacag ua                                            22

<210> SEQ ID NO 113
<211> LENGTH: 22
<212> TYPE: RNA
<213> ORGANISM: Mus musculus

<400> SEQUENCE: 113
ugagguagua guguguacag uu                                            22

<210> SEQ ID NO 114
<211> LENGTH: 19
<212> TYPE: RNA
<213> ORGANISM: Mus musculus

<400> SEQUENCE: 114
ugagguagua guuugugcu                                                19

<210> SEQ ID NO 115
<211> LENGTH: 22
<212> TYPE: RNA
<213> ORGANISM: Mus musculus

<400> SEQUENCE: 115
uggaauguaa agaaguaugu aa                                            22

<210> SEQ ID NO 116
<211> LENGTH: 22
<212> TYPE: RNA
<213> ORGANISM: Mus musculus

<400> SEQUENCE: 116
uggaauguaa agaaguaugu ac                                            22

<210> SEQ ID NO 117
<211> LENGTH: 23
<212> TYPE: RNA
<213> ORGANISM: Mus musculus

<400> SEQUENCE: 117

-continued uggaauguaa agaaguaugu auu         23

<210> SEQ ID NO 118
<211> LENGTH: 23
<212> TYPE: RNA
<213> ORGANISM: Mus musculus

<400> SEQUENCE: 118
ucuuugguua ucuagcugua uga         23

<210> SEQ ID NO 119
<211> LENGTH: 22
<212> TYPE: RNA
<213> ORGANISM: Mus musculus

<400> SEQUENCE: 119
uagcagcaca uaaugguuug ug          22

<210> SEQ ID NO 120
<211> LENGTH: 22
<212> TYPE: RNA
<213> ORGANISM: Mus musculus

<400> SEQUENCE: 120
uagcagcaca ucaugguuua ca          22

<210> SEQ ID NO 121
<211> LENGTH: 22
<212> TYPE: RNA
<213> ORGANISM: Mus musculus

<400> SEQUENCE: 121
uagcagcacg uaaauauugg cg          22

<210> SEQ ID NO 122
<211> LENGTH: 22
<212> TYPE: RNA
<213> ORGANISM: Mus musculus

<400> SEQUENCE: 122
uaaggugcau cuagugcaga ua          22

<210> SEQ ID NO 123
<211> LENGTH: 23
<212> TYPE: RNA
<213> ORGANISM: Mus musculus

<400> SEQUENCE: 123
ugugcaaauc caugcaaaac uga         23

<210> SEQ ID NO 124
<211> LENGTH: 23
<212> TYPE: RNA
<213> ORGANISM: Mus musculus

<400> SEQUENCE: 124
uaaagugcuu auagugcagg uag         23

<210> SEQ ID NO 125
<211> LENGTH: 22
<212> TYPE: RNA
<213> ORGANISM: Mus musculus

<400> SEQUENCE: 125

-continued

```
uagcuuauca gacugauguu ga                                              22

<210> SEQ ID NO 126
<211> LENGTH: 22
<212> TYPE: RNA
<213> ORGANISM: Mus musculus

<400> SEQUENCE: 126
aagcugccag uugaagaacu gu                                              22

<210> SEQ ID NO 127
<211> LENGTH: 21
<212> TYPE: RNA
<213> ORGANISM: Mus musculus

<400> SEQUENCE: 127
aucacauugc cagggauuuc c                                               21

<210> SEQ ID NO 128
<211> LENGTH: 23
<212> TYPE: RNA
<213> ORGANISM: Mus musculus

<400> SEQUENCE: 128
aucacauugc cagggauuac cac                                             23

<210> SEQ ID NO 129
<211> LENGTH: 22
<212> TYPE: RNA
<213> ORGANISM: Mus musculus

<400> SEQUENCE: 129
uggcucaguu cagcaggaac ag                                              22

<210> SEQ ID NO 130
<211> LENGTH: 22
<212> TYPE: RNA
<213> ORGANISM: Mus musculus

<400> SEQUENCE: 130
uucaaguaau ccaggauagg cu                                              22

<210> SEQ ID NO 131
<211> LENGTH: 22
<212> TYPE: RNA
<213> ORGANISM: Mus musculus

<400> SEQUENCE: 131
uucaaguaau ucaggauagg uu                                              22

<210> SEQ ID NO 132
<211> LENGTH: 22
<212> TYPE: RNA
<213> ORGANISM: Mus musculus

<400> SEQUENCE: 132
uucacagugg cuaaguuccg cu                                              22

<210> SEQ ID NO 133
<211> LENGTH: 20
<212> TYPE: RNA
<213> ORGANISM: Mus musculus
```

```
<400> SEQUENCE: 133
uucacagugg cuaaguucug                                              20

<210> SEQ ID NO 134
<211> LENGTH: 22
<212> TYPE: RNA
<213> ORGANISM: Mus musculus

<400> SEQUENCE: 134
cuagcaccau cugaaaucgg uu                                           22

<210> SEQ ID NO 135
<211> LENGTH: 23
<212> TYPE: RNA
<213> ORGANISM: Mus musculus

<400> SEQUENCE: 135
uagcaccauu ugaaaucagu guu                                          23

<210> SEQ ID NO 136
<211> LENGTH: 22
<212> TYPE: RNA
<213> ORGANISM: Mus musculus

<400> SEQUENCE: 136
uagcaccauu ugaaaucggu ua                                           22

<210> SEQ ID NO 137
<211> LENGTH: 23
<212> TYPE: RNA
<213> ORGANISM: Mus musculus

<400> SEQUENCE: 137
uguaaacauc cucgacugga agc                                          23

<210> SEQ ID NO 138
<211> LENGTH: 22
<212> TYPE: RNA
<213> ORGANISM: Mus musculus

<400> SEQUENCE: 138
cuuucagucg gauguuugca gc                                           22

<210> SEQ ID NO 139
<211> LENGTH: 21
<212> TYPE: RNA
<213> ORGANISM: Mus musculus

<400> SEQUENCE: 139
uguaaacauc cuacacucag c                                            21

<210> SEQ ID NO 140
<211> LENGTH: 23
<212> TYPE: RNA
<213> ORGANISM: Mus musculus

<400> SEQUENCE: 140
uguaaacauc cuacacucuc agc                                          23

<210> SEQ ID NO 141
<211> LENGTH: 22
<212> TYPE: RNA
<213> ORGANISM: Mus musculus
```

-continued

```
<400> SEQUENCE: 141
uguaaacauc cccgacugga ag                                              22

<210> SEQ ID NO 142
<211> LENGTH: 20
<212> TYPE: RNA
<213> ORGANISM: Mus musculus

<400> SEQUENCE: 142
acccguagau ccgaucuugu                                                 20

<210> SEQ ID NO 143
<211> LENGTH: 22
<212> TYPE: RNA
<213> ORGANISM: Mus musculus

<400> SEQUENCE: 143
cacccguaga accgaccuug cg                                              22

<210> SEQ ID NO 144
<211> LENGTH: 20
<212> TYPE: RNA
<213> ORGANISM: Mus musculus

<400> SEQUENCE: 144
uacaguacug ugauaacuga                                                 20

<210> SEQ ID NO 145
<211> LENGTH: 23
<212> TYPE: RNA
<213> ORGANISM: Mus musculus

<400> SEQUENCE: 145
uggaguguga caauggguguu ugu                                            23

<210> SEQ ID NO 146
<211> LENGTH: 23
<212> TYPE: RNA
<213> ORGANISM: Mus musculus

<400> SEQUENCE: 146
uggaguguga caauggguguu uga                                            23

<210> SEQ ID NO 147
<211> LENGTH: 22
<212> TYPE: RNA
<213> ORGANISM: Mus musculus

<400> SEQUENCE: 147
uggaguguga caauggguguu ug                                             22

<210> SEQ ID NO 148
<211> LENGTH: 21
<212> TYPE: RNA
<213> ORGANISM: Mus musculus

<400> SEQUENCE: 148
cauuauuacu uuugguacgc g                                               21

<210> SEQ ID NO 149
<211> LENGTH: 22
<212> TYPE: RNA
```

<213> ORGANISM: Mus musculus

<400> SEQUENCE: 149
uuaaggcacg cggugaaugc ca                                    22

<210> SEQ ID NO 150
<211> LENGTH: 21
<212> TYPE: RNA
<213> ORGANISM: Mus musculus

<400> SEQUENCE: 150
uuaaggcacg cgggugaaug c                                     21

<210> SEQ ID NO 151
<211> LENGTH: 23
<212> TYPE: RNA
<213> ORGANISM: Mus musculus

<400> SEQUENCE: 151
ucccugagac ccuuuaaccu gug                                   23

<210> SEQ ID NO 152
<211> LENGTH: 22
<212> TYPE: RNA
<213> ORGANISM: Mus musculus

<400> SEQUENCE: 152
ucccugagac ccuaacuugu ga                                    22

<210> SEQ ID NO 153
<211> LENGTH: 21
<212> TYPE: RNA
<213> ORGANISM: Mus musculus

<400> SEQUENCE: 153
ucguaccgug aguaauaaug c                                     21

<210> SEQ ID NO 154
<211> LENGTH: 22
<212> TYPE: RNA
<213> ORGANISM: Mus musculus

<400> SEQUENCE: 154
ucggauccgu cugagcuugg cu                                    22

<210> SEQ ID NO 155
<211> LENGTH: 22
<212> TYPE: RNA
<213> ORGANISM: Mus musculus

<400> SEQUENCE: 155
ucacagugaa ccggucucuu uu                                    22

<210> SEQ ID NO 156
<211> LENGTH: 21
<212> TYPE: RNA
<213> ORGANISM: Mus musculus

<400> SEQUENCE: 156 cuuuuucgg ucugggcuug c                                      21

<210> SEQ ID NO 157
<211> LENGTH: 20

<212> TYPE: RNA
<213> ORGANISM: Mus musculus

<400> SEQUENCE: 157
cagugcaaug uuaaaagggc                                                    20

<210> SEQ ID NO 158
<211> LENGTH: 21
<212> TYPE: RNA
<213> ORGANISM: Mus musculus

<400> SEQUENCE: 158
uaaagcuaga uaaccgaaag u                                                  21

<210> SEQ ID NO 159
<211> LENGTH: 23
<212> TYPE: RNA
<213> ORGANISM: Mus musculus

<400> SEQUENCE: 159
uaacagucua cagccauggu cgu                                                23

<210> SEQ ID NO 160
<211> LENGTH: 22
<212> TYPE: RNA
<213> ORGANISM: Mus musculus

<400> SEQUENCE: 160
uugguccccu ucaaccagcu gu                                                 22

<210> SEQ ID NO 161
<211> LENGTH: 22
<212> TYPE: RNA
<213> ORGANISM: Mus musculus

<400> SEQUENCE: 161
ugugacuggu ugaccagagg ga                                                 22

<210> SEQ ID NO 162
<211> LENGTH: 24
<212> TYPE: RNA
<213> ORGANISM: Mus musculus

<400> SEQUENCE: 162
uauggcuuuu uauuccuaug ugaa                                               24

<210> SEQ ID NO 163
<211> LENGTH: 23
<212> TYPE: RNA
<213> ORGANISM: Mus musculus

<400> SEQUENCE: 163
acuccauuug uuuugaugau gga                                                23

<210> SEQ ID NO 164
<211> LENGTH: 22
<212> TYPE: RNA
<213> ORGANISM: Mus musculus

<400> SEQUENCE: 164
uauugcuuaa gaauacgcgu ag                                                 22

<210> SEQ ID NO 165

```
<211> LENGTH: 17
<212> TYPE: RNA
<213> ORGANISM: Mus musculus

<400> SEQUENCE: 165
agcuggucuu gugaauc                                                        17

<210> SEQ ID NO 166
<211> LENGTH: 18
<212> TYPE: RNA
<213> ORGANISM: Mus musculus

<400> SEQUENCE: 166
ucuacagugc acgugucu                                                       18

<210> SEQ ID NO 167
<211> LENGTH: 21
<212> TYPE: RNA
<213> ORGANISM: Mus musculus

<400> SEQUENCE: 167
agugguuuua cccuauggua g                                                   21

<210> SEQ ID NO 168
<211> LENGTH: 21
<212> TYPE: RNA
<213> ORGANISM: Mus musculus

<400> SEQUENCE: 168
aacacugucu gguaaagaug g                                                   21

<210> SEQ ID NO 169
<211> LENGTH: 20
<212> TYPE: RNA
<213> ORGANISM: Mus musculus

<400> SEQUENCE: 169
cauaaaguag aaagcacuac                                                     20

<210> SEQ ID NO 170
<211> LENGTH: 22
<212> TYPE: RNA
<213> ORGANISM: Mus musculus

<400> SEQUENCE: 170
uguaguguuu ccuacuuuau gg                                                  22

<210> SEQ ID NO 171
<211> LENGTH: 22
<212> TYPE: RNA
<213> ORGANISM: Mus musculus

<400> SEQUENCE: 171
ugagaugaag cacguagcu ca                                                   22

<210> SEQ ID NO 172
<211> LENGTH: 22
<212> TYPE: RNA
<213> ORGANISM: Mus musculus

<400> SEQUENCE: 172
uacaguauag augauguacu ag                                                  22
```

```
<210> SEQ ID NO 173
<211> LENGTH: 24
<212> TYPE: RNA
<213> ORGANISM: Mus musculus

<400> SEQUENCE: 173
guccaguuuu cccaggaauc ccuu                                              24

<210> SEQ ID NO 174
<211> LENGTH: 23
<212> TYPE: RNA
<213> ORGANISM: Mus musculus

<400> SEQUENCE: 174
ugagaacuga auccauggg uuu                                                23

<210> SEQ ID NO 175
<211> LENGTH: 21
<212> TYPE: RNA
<213> ORGANISM: Mus musculus

<400> SEQUENCE: 175
guguguggaa augcuucugc c                                                 21

<210> SEQ ID NO 176
<211> LENGTH: 22
<212> TYPE: RNA
<213> ORGANISM: Mus musculus

<400> SEQUENCE: 176
ucagugcacu acagaacuuu gu                                                22

<210> SEQ ID NO 177
<211> LENGTH: 22
<212> TYPE: RNA
<213> ORGANISM: Mus musculus

<400> SEQUENCE: 177
ucuggcuccg ugucuucacu cc                                                22

<210> SEQ ID NO 178
<211> LENGTH: 23
<212> TYPE: RNA
<213> ORGANISM: Mus musculus

<400> SEQUENCE: 178
ucucccaacc cuuguaccag ugu                                               23

<210> SEQ ID NO 179
<211> LENGTH: 22
<212> TYPE: RNA
<213> ORGANISM: Mus musculus

<400> SEQUENCE: 179
cuagacugag gcuccuugag gu                                                22

<210> SEQ ID NO 180
<211> LENGTH: 21
<212> TYPE: RNA
<213> ORGANISM: Mus musculus

<400> SEQUENCE: 180
ucagugcaug acagaacuug g                                                 21
```

-continued

```
<210> SEQ ID NO 181
<211> LENGTH: 20
<212> TYPE: RNA
<213> ORGANISM: Mus musculus

<400> SEQUENCE: 181
uugcauaguc acaaaaguga                                               20

<210> SEQ ID NO 182
<211> LENGTH: 22
<212> TYPE: RNA
<213> ORGANISM: Mus musculus

<400> SEQUENCE: 182
uagguuaucc guguugccuu cg                                            22

<210> SEQ ID NO 183
<211> LENGTH: 22
<212> TYPE: RNA
<213> ORGANISM: Mus musculus

<400> SEQUENCE: 183
uuaaugcuaa uugugauagg gg                                            22

<210> SEQ ID NO 184
<211> LENGTH: 23
<212> TYPE: RNA
<213> ORGANISM: Mus musculus

<400> SEQUENCE: 184
aacauucaac gcugucggug agu                                           23

<210> SEQ ID NO 185
<211> LENGTH: 22
<212> TYPE: RNA
<213> ORGANISM: Mus musculus

<400> SEQUENCE: 185
uuuggcaaug guagaacuca ca                                            22

<210> SEQ ID NO 186
<211> LENGTH: 23
<212> TYPE: RNA
<213> ORGANISM: Mus musculus

<400> SEQUENCE: 186
uauggcacug guagaauuca cug                                           23

<210> SEQ ID NO 187
<211> LENGTH: 22
<212> TYPE: RNA
<213> ORGANISM: Unknown
<220> FEATURE:
<223> OTHER INFORMATION: Sequence isolated from both Homo sapiens (Human
      osteocaroma cells) and Mus musculus

<400> SEQUENCE: 187
cuuuuugcgg ucugggcuug uu                                            22

<210> SEQ ID NO 188
<211> LENGTH: 22
<212> TYPE: RNA
<213> ORGANISM: Mus musculus
```

```
<400> SEQUENCE: 188
uggacggaga acugauaagg gu                                        22

<210> SEQ ID NO 189
<211> LENGTH: 18
<212> TYPE: RNA
<213> ORGANISM: Mus musculus

<400> SEQUENCE: 189
uggagagaaa ggcaguuc                                             18

<210> SEQ ID NO 190
<211> LENGTH: 23
<212> TYPE: RNA
<213> ORGANISM: Unknown
<220> FEATURE:
<223> OTHER INFORMATION: Sequence isolated from both Homo sapiens (Human
      osteocaroma cells) and Mus musculus

<400> SEQUENCE: 190
caaagaauuc uccuuuuggg cuu                                       23

<210> SEQ ID NO 191
<211> LENGTH: 22
<212> TYPE: RNA
<213> ORGANISM: Mus musculus

<400> SEQUENCE: 191
ucgugucuug uguugcagcc gg                                        22

<210> SEQ ID NO 192
<211> LENGTH: 21
<212> TYPE: RNA
<213> ORGANISM: Mus musculus

<400> SEQUENCE: 192
uaacacuguc ugguaacgau g                                         21

<210> SEQ ID NO 193
<211> LENGTH: 22
<212> TYPE: RNA
<213> ORGANISM: Mus musculus

<400> SEQUENCE: 193
caucccuugc augguggagg gu                                        22

<210> SEQ ID NO 194
<211> LENGTH: 23
<212> TYPE: RNA
<213> ORGANISM: Mus musculus

<400> SEQUENCE: 194
gugccuacug agcugacauc agu                                       23

<210> SEQ ID NO 195
<211> LENGTH: 22
<212> TYPE: RNA
<213> ORGANISM: Mus musculus

<400> SEQUENCE: 195
ugauauguuu gauauauuag gu                                        22

<210> SEQ ID NO 196
```

```
<211> LENGTH: 22
<212> TYPE: RNA
<213> ORGANISM: Mus musculus

<400> SEQUENCE: 196
caacggaauc ccaaaagcag cu                                              22

<210> SEQ ID NO 197
<211> LENGTH: 18
<212> TYPE: RNA
<213> ORGANISM: Mus musculus

<400> SEQUENCE: 197
cugaccuaug aauugaca                                                   18

<210> SEQ ID NO 198
<211> LENGTH: 22
<212> TYPE: RNA
<213> ORGANISM: Mus musculus

<400> SEQUENCE: 198
uaccacaggg uagaaccacg ga                                              22

<210> SEQ ID NO 199
<211> LENGTH: 21
<212> TYPE: RNA
<213> ORGANISM: Mus musculus

<400> SEQUENCE: 199
aacuggccua caaaguccca g                                               21

<210> SEQ ID NO 200
<211> LENGTH: 22
<212> TYPE: RNA
<213> ORGANISM: Mus musculus

<400> SEQUENCE: 200
uguaacagca acuccaugug ga                                              22

<210> SEQ ID NO 201
<211> LENGTH: 21
<212> TYPE: RNA
<213> ORGANISM: Mus musculus

<400> SEQUENCE: 201
uagcagcaca gaaauauugg c                                               21

<210> SEQ ID NO 202
<211> LENGTH: 21
<212> TYPE: RNA
<213> ORGANISM: Homo sapiens

<400> SEQUENCE: 202
uagguaguuu cauguuguug g                                               21

<210> SEQ ID NO 203
<211> LENGTH: 22
<212> TYPE: RNA
<213> ORGANISM: Homo sapiens

<400> SEQUENCE: 203
uucaccaccu ucuccaccca gc                                              22
```

```
<210> SEQ ID NO 204
<211> LENGTH: 19
<212> TYPE: RNA
<213> ORGANISM: Homo sapiens

<400> SEQUENCE: 204
gguccagagg ggagauagg                                                19

<210> SEQ ID NO 205
<211> LENGTH: 22
<212> TYPE: RNA
<213> ORGANISM: Homo sapiens

<400> SEQUENCE: 205
cccaguguuc agacuaccug uu                                            22

<210> SEQ ID NO 206
<211> LENGTH: 23
<212> TYPE: RNA
<213> ORGANISM: Mus musculus

<400> SEQUENCE: 206
uaauacugcc ugguaaugau gac                                           23

<210> SEQ ID NO 207
<211> LENGTH: 21
<212> TYPE: RNA
<213> ORGANISM: Mus musculus

<400> SEQUENCE: 207
uacucaguaa ggcauuguuc u                                             21

<210> SEQ ID NO 208
<211> LENGTH: 22
<212> TYPE: RNA
<213> ORGANISM: Mus musculus

<400> SEQUENCE: 208
agagguauag cgcaugggaa ga                                            22

<210> SEQ ID NO 209
<211> LENGTH: 21
<212> TYPE: RNA
<213> ORGANISM: Mus musculus

<400> SEQUENCE: 209
ugaaauguuu aggaccacua g                                             21

<210> SEQ ID NO 210
<211> LENGTH: 23
<212> TYPE: RNA
<213> ORGANISM: Mus musculus

<400> SEQUENCE: 210
uucccuuugu cauccuaugc cug                                           23

<210> SEQ ID NO 211
<211> LENGTH: 22
<212> TYPE: RNA
<213> ORGANISM: Mus musculus

<400> SEQUENCE: 211
uccuucauuc caccggaguc ug                                            22
```

```
<210> SEQ ID NO 212
<211> LENGTH: 23
<212> TYPE: RNA
<213> ORGANISM: Mus musculus

<400> SEQUENCE: 212
gugaaauguu uaggaccacu aga                                              23

<210> SEQ ID NO 213
<211> LENGTH: 22
<212> TYPE: RNA
<213> ORGANISM: Mus musculus

<400> SEQUENCE: 213
uggaauguaa ggaagugugu gg                                               22

<210> SEQ ID NO 214
<211> LENGTH: 22
<212> TYPE: RNA
<213> ORGANISM: Mus musculus

<400> SEQUENCE: 214
uacaguaguc ugcacauugg uu                                               22

<210> SEQ ID NO 215
<211> LENGTH: 22
<212> TYPE: RNA
<213> ORGANISM: Mus musculus

<400> SEQUENCE: 215
cccuguagaa ccgaauuugu gu                                               22

<210> SEQ ID NO 216
<211> LENGTH: 24
<212> TYPE: RNA
<213> ORGANISM: Mus musculus

<400> SEQUENCE: 216
aacccguaga uccgaacuug ugaa                                             24

<210> SEQ ID NO 217
<211> LENGTH: 23
<212> TYPE: RNA
<213> ORGANISM: Mus musculus

<400> SEQUENCE: 217
gcuucuccug gcucuccucc cuc                                              23

<210> SEQ ID NO 218
<211> LENGTH: 91
<212> TYPE: RNA
<213> ORGANISM: Drosophila melanogaster
<220> FEATURE:
<221> NAME/KEY: misc_RNA
<222> LOCATION: (1)..(91)
<223> OTHER INFORMATION: predicted precursor structure: mir-1, 5' to 3'
      sequence

<400> SEQUENCE: 218
uucagccuuu gagaguucca ugcuuccuug cauucaauag uuauauucaa gcauauggaa      60
uguaaagaag uauggagcga aaucuggcga g                                     91

<210> SEQ ID NO 219
```

```
<211> LENGTH: 76
<212> TYPE: RNA
<213> ORGANISM: Drosophila melanogaster
<220> FEATURE:
<221> NAME/KEY: misc_RNA
<222> LOCATION: (1)..(76)
<223> OTHER INFORMATION: predicted precursor structure: mir-2a-1, 5' to
      3' sequence

<400> SEQUENCE: 219
gcugggcucu caaagugguu gugaaaugca uuccgcuuu gcgcggcaua ucacagccag    60 cuugaugag cuuagc                                                   76

<210> SEQ ID NO 220
<211> LENGTH: 72
<212> TYPE: RNA
<213> ORGANISM: Drosophila melanogaster
<220> FEATURE:
<221> NAME/KEY: misc_RNA
<222> LOCATION: (1)..(72)
<223> OTHER INFORMATION: predicted precursor structure: mir-2a-2, 5' to
      3' sequence

<400> SEQUENCE: 220
aucuaagccu caucaagugg uugugauaug gauacccaac gcauaucaca gccagcuuug    60
augagcuagg au                                                       72

<210> SEQ ID NO 221
<211> LENGTH: 77
<212> TYPE: RNA
<213> ORGANISM: Drosophila melanogaster
<220> FEATURE:
<221> NAME/KEY: misc_RNA
<222> LOCATION: (1)..(77)
<223> OTHER INFORMATION: predicted precursor structure: mir-2b-1, 5' to
      3' sequence

<400> SEQUENCE: 221
cuucaacugu cuucaaagug gcagugacau guugucaaca auauucauau cacagccagc    60
uuugaggagc guugcgg                                                   77

<210> SEQ ID NO 222
<211> LENGTH: 83
<212> TYPE: RNA
<213> ORGANISM: Drosophila melanogaster
<220> FEATURE:
<221> NAME/KEY: misc_RNA
<222> LOCATION: (1)..(83)
<223> OTHER INFORMATION: predicted precursor structure: mir-2b-2, 5' to
      3' sequence

<400> SEQUENCE: 222
uugugucauu cuucaaagug guugugaaau guuugccuuu uuaugccuau ucauaucaca    60
gccagcuuug aggagcgacg cga                                            83

<210> SEQ ID NO 223
<211> LENGTH: 69
<212> TYPE: RNA
<213> ORGANISM: Drosophila melanogaster
<220> FEATURE:
<221> NAME/KEY: misc_RNA
<222> LOCATION: (1)..(69)
<223> OTHER INFORMATION: predicted precursor structure: mir-3, 5' to 3'
      sequence

<400> SEQUENCE: 223
```

```
gauccuggga ugcaucuugu gcaguuaugu uucaaucuca caucacuggg caaagugugu        60
cucaagauc                                                               69
```

<210> SEQ ID NO 224
<211> LENGTH: 82
<212> TYPE: RNA
<213> ORGANISM: Drosophila melanogaster
<220> FEATURE:
<221> NAME/KEY: misc_RNA
<222> LOCATION: (1)..(82)
<223> OTHER INFORMATION: predicted precursor structure: mir-4, 5' to 3'
      sequence

<400> SEQUENCE: 224

```
uugcaauuag uuucuuuggu cguccagccu uagggugauu uuccgguca uaaagcuaga        60 caaccauuga aguucguugu gg                                                82
```

<210> SEQ ID NO 225
<211> LENGTH: 69
<212> TYPE: RNA
<213> ORGANISM: Drosophila melanogaster
<220> FEATURE:
<221> NAME/KEY: misc_RNA
<222> LOCATION: (1)..(69)
<223> OTHER INFORMATION: predicted precursor structure: mir-5, 5' to 3'
      sequence

<400> SEQUENCE: 225

```
gcuaaaagga acgaucguug ugauaugagu uguuccuaa cauaucacag ugauuuuccu        60
uuauaacgc                                                               69
```

<210> SEQ ID NO 226
<211> LENGTH: 81
<212> TYPE: RNA
<213> ORGANISM: Drosophila melanogaster
<220> FEATURE:
<221> NAME/KEY: misc_RNA
<222> LOCATION: (1)..(81)
<223> OTHER INFORMATION: predicted precursor structure: mir-6-1, 5' to
      3' sequence

<400> SEQUENCE: 226

```
uuuaauguag agggaauagu ugcugugcug uaaguuaaua uaccauaucu auaucacagg        60
gcuguucuuu uuguaccuaa a                                                 81
```

<210> SEQ ID NO 227
<211> LENGTH: 74
<212> TYPE: RNA
<213> ORGANISM: Drosophila melanogaster
<220> FEATURE:
<221> NAME/KEY: misc_RNA
<222> LOCATION: (1)..(74)
<223> OTHER INFORMATION: predicted precursor structure: mir-6-2, 5' to
      3' sequence

<400> SEQUENCE: 227

```
uaacccaagg gaacuucugc ugcugauaua uuauugaaaa acuacuauau cacaguggcu        60 guucuuuug guug                                                          74
```

<210> SEQ ID NO 228
<211> LENGTH: 79
<212> TYPE: RNA
<213> ORGANISM: Drosophila melanogaster
<220> FEATURE:
<221> NAME/KEY: misc_RNA

```
<222> LOCATION: (1)..(79)
<223> OTHER INFORMATION: predicted precursor structure: mir-6-3, 5' to
      3' sequence

<400> SEQUENCE: 228
caaaaagaag ggaacgguug cugaugaugu aguuugaaac ucucacaauu uauaucacag    60
uggcuguucu uuuuguuug                                                 79

<210> SEQ ID NO 229
<211> LENGTH: 88
<212> TYPE: RNA
<213> ORGANISM: Drosophila melanogaster
<220> FEATURE:
<221> NAME/KEY: misc_RNA
<222> LOCATION: (1)..(88)
<223> OTHER INFORMATION: predicted precursor structure: mir-7, 5' to 3'
      sequence

<400> SEQUENCE: 229
gagugcauuc cguauggaag acuagugauu uuguguuug gucuuuggua auaacaauaa    60
aucccuuguc uucuuacggc gugcauuu                                       88

<210> SEQ ID NO 230
<211> LENGTH: 87
<212> TYPE: RNA
<213> ORGANISM: Drosophila melanogaster
<220> FEATURE:
<221> NAME/KEY: misc_RNA
<222> LOCATION: (1)..(87)
<223> OTHER INFORMATION: predicted precursor structure: mir-8, 5' to 3'
      sequence

<400> SEQUENCE: 230
aaggacaucu guucacaucu uaccgggcag cauuagaucc uuuuuauaac ucuaauacug    60
ucagguaaag augucguccg ugccuu                                         87

<210> SEQ ID NO 231
<211> LENGTH: 78
<212> TYPE: RNA
<213> ORGANISM: Drosophila melanogaster
<220> FEATURE:
<221> NAME/KEY: misc_RNA
<222> LOCATION: (1)..(78)
<223> OTHER INFORMATION: predicted precursor structure: mir-9, 5' to 3'
      sequence

<400> SEQUENCE: 231
gcuauguugu cuuugguuau cuagcuguau gagugauaaa uaacgucaua aagcuagcuu    60
accgaaguua auauuagc                                                  78

<210> SEQ ID NO 232
<211> LENGTH: 77
<212> TYPE: RNA
<213> ORGANISM: Drosophila melanogaster
<220> FEATURE:
<221> NAME/KEY: misc_RNA
<222> LOCATION: (1)..(77)
<223> OTHER INFORMATION: predicted precursor structure: mir-10, 5' to 3'
      sequence

<400> SEQUENCE: 232
ccacgucuac ccuguagauc cgaauuuguu uuauacuagc uuuaaggaca aauucgguuc    60
uagagagguu ugugugg                                                   77
```

```
<210> SEQ ID NO 233
<211> LENGTH: 75
<212> TYPE: RNA
<213> ORGANISM: Drosophila melanogaster
<220> FEATURE:
<221> NAME/KEY: misc_RNA
<222> LOCATION: (1)..(75)
<223> OTHER INFORMATION: predicted precursor structure: mir-11, 5' to 3'
      sequence

<400> SEQUENCE: 233
gcacuuguca agaacuuucu cugugacccg cguguacuua aaagccgcau cacagucuga    60
guucuugcug agugc                                                    75

<210> SEQ ID NO 234
<211> LENGTH: 74
<212> TYPE: RNA
<213> ORGANISM: Drosophila melanogaster
<220> FEATURE:
<221> NAME/KEY: misc_RNA
<222> LOCATION: (1)..(74)
<223> OTHER INFORMATION: predicted precursor structure: mir-12, 5' to 3'
      sequence

<400> SEQUENCE: 234
uacgguugag uauuacauca gguacuggug ugccuuaaau ccaacaacca guacuuaugu    60
cauacuacgc cgug                                                     74

<210> SEQ ID NO 235
<211> LENGTH: 75
<212> TYPE: RNA
<213> ORGANISM: Drosophila melanogaster
<220> FEATURE:
<221> NAME/KEY: misc_RNA
<222> LOCATION: (1)..(75)
<223> OTHER INFORMATION: predicted precursor structure: mir-13a, 5' to
      3' sequence

<400> SEQUENCE: 235
uacguaacuc cucaaagggu ugugaaaugu cgacuauuau cuacucauau cacagccauu    60
uugaugaguu ucgug                                                    75

<210> SEQ ID NO 236
<211> LENGTH: 68
<212> TYPE: RNA
<213> ORGANISM: Drosophila melanogaster
<220> FEATURE:
<221> NAME/KEY: misc_RNA
<222> LOCATION: (1)..(68)
<223> OTHER INFORMATION: predicted precursor structure: mir-13b-1, 5' to
      3' sequence

<400> SEQUENCE: 236
ccaugucguu aaaauguuug ugaacuuaug uauucacaau cauaucacag ccauuuugac    60
gaguuugg                                                            68

<210> SEQ ID NO 237
<211> LENGTH: 70
<212> TYPE: RNA
<213> ORGANISM: Drosophila melanogaster
<220> FEATURE:
<221> NAME/KEY: misc_RNA
<222> LOCATION: (1)..(70)
<223> OTHER INFORMATION: predicted precursor structure: mir-13b-2, 5' to
      3' sequence

<400> SEQUENCE: 237
```
uauuaacgcg ucaaaaugac ugugagcuau guggauuuga cuucauauca cagccauuuu    60
gacgaguuug                                                           70

<210> SEQ ID NO 238
<211> LENGTH: 65
<212> TYPE: RNA
<213> ORGANISM: Drosophila melanogaster
<220> FEATURE:
<221> NAME/KEY: misc_RNA
<222> LOCATION: (1)..(65)
<223> OTHER INFORMATION: predicted precursor structure: mir-14, 5' to 3'
      sequence

<400> SEQUENCE: 238
ugugggagcg agacguggga cucacugugc uuauuaaaua gucagucuug uuucucucuc    60
cuaua                                                                65

<210> SEQ ID NO 239
<211> LENGTH: 80
<212> TYPE: RNA
<213> ORGANISM: Homo sapiens
<220> FEATURE:
<221> NAME/KEY: misc_RNA
<222> LOCATION: (1)..(80)
<223> OTHER INFORMATION: predicted precursor structure: let-7a-1, 5' to
      3' sequence

<400> SEQUENCE: 239
ugggaugagg uaguagguug uauaguuuua gggucacacc caccacuggg agauaacuau    60
acaaucuacu gcuuuccua                                                 80

<210> SEQ ID NO 240
<211> LENGTH: 72
<212> TYPE: RNA
<213> ORGANISM: Homo sapiens
<220> FEATURE:
<221> NAME/KEY: misc_RNA
<222> LOCATION: (1)..(72)
<223> OTHER INFORMATION: predicted precursor structure: let-7a-2, 5' to
      3' sequence

<400> SEQUENCE: 240
agguugaggu aguagguugu auaguuuaga auuacaucaa gggagauaac uguacagccu    60
ccuagcuuuc cu                                                        72

<210> SEQ ID NO 241
<211> LENGTH: 74
<212> TYPE: RNA
<213> ORGANISM: Homo sapiens
<220> FEATURE:
<221> NAME/KEY: misc_RNA
<222> LOCATION: (1)..(74)
<223> OTHER INFORMATION: predicted precursor structure: let-7a-3, 5' to
      3' sequence

<400> SEQUENCE: 241
gggugaggua guagguugua uaguuugggg cucugcccug cuauggaua acauauacaau    60 cuacugucuu uccu                                                      74

<210> SEQ ID NO 242
<211> LENGTH: 83
<212> TYPE: RNA
<213> ORGANISM: Homo sapiens
<220> FEATURE:

```
<221> NAME/KEY: misc_RNA
<222> LOCATION: (1)..(83)
<223> OTHER INFORMATION: predicted precursor structure: let-7b, 5' to 3'
      sequence

<400> SEQUENCE: 242
cggggugagg uaguagguug ugugguuuca gggcagugau uugcccuc ggaagauaac       60 uauacaaccu acugccuucc cug                                            83

<210> SEQ ID NO 243
<211> LENGTH: 85
<212> TYPE: RNA
<213> ORGANISM: Homo sapiens
<220> FEATURE:
<221> NAME/KEY: misc_RNA
<222> LOCATION: (1)..(85)
<223> OTHER INFORMATION: predicted precursor structure: let-7c, 5' to 3'
      sequence

<400> SEQUENCE: 243
gcauccgggu ugagguagua gguuguaugg uuuagaguua cacccugggg aguuaacugu     60
acaaccuucu agcuuuccuu ggagc                                          85

<210> SEQ ID NO 244
<211> LENGTH: 87
<212> TYPE: RNA
<213> ORGANISM: Homo sapiens
<220> FEATURE:
<221> NAME/KEY: misc_RNA
<222> LOCATION: (1)..(87)
<223> OTHER INFORMATION: predicted precursor structure: let-7d, 5' to 3'
      sequence

<400> SEQUENCE: 244
ccuaggaaga gguaguaggu ugcauaguuu uagggcaggg auuuugccca caaggaggua     60
acuauacgac cugcugccuu ucuuagg                                        87

<210> SEQ ID NO 245
<211> LENGTH: 79
<212> TYPE: RNA
<213> ORGANISM: Homo sapiens
<220> FEATURE:
<221> NAME/KEY: misc_RNA
<222> LOCATION: (1)..(79)
<223> OTHER INFORMATION: predicted precursor structure: let-7e, 5' to 3'
      sequence

<400> SEQUENCE: 245
cccgggcuga gguaggaggu uguauaguug aggaggacac ccaaggagau cacuauacgg     60
ccuccuagcu uucccagg                                                  79

<210> SEQ ID NO 246
<211> LENGTH: 87
<212> TYPE: RNA
<213> ORGANISM: Homo sapiens
<220> FEATURE:
<221> NAME/KEY: misc_RNA
<222> LOCATION: (1)..(87)
<223> OTHER INFORMATION: predicted precursor structure: let-7f-1, 5' to
      3' sequence

<400> SEQUENCE: 246
ucagagugag guaguagauu guauaguugu ggguaguga uuuuacccug uucaggagau      60
aacuauacaa ucuauugccu ucccuga                                        87
```

<210> SEQ ID NO 247
<211> LENGTH: 85
<212> TYPE: RNA
<213> ORGANISM: Homo sapiens
<220> FEATURE:
<221> NAME/KEY: misc_RNA
<222> LOCATION: (1)..(85)
<223> OTHER INFORMATION: predicted precursor structure: let-7f-2, 5' to
      3' sequence

<400> SEQUENCE: 247
cugugggaug agguaguaga uuguauaguu uuagggucau accccaucuu ggagauaacu    60
auacagucua cugucuuucc cacgg                                         85

<210> SEQ ID NO 248
<211> LENGTH: 83
<212> TYPE: RNA
<213> ORGANISM: Homo sapiens
<220> FEATURE:
<221> NAME/KEY: misc_RNA
<222> LOCATION: (1)..(83)
<223> OTHER INFORMATION: predicted precursor structure: mir-15, 5' to 3'
      sequence

<400> SEQUENCE: 248
ccuuggagua aaguagcagc acauaauggu uuguggauuu ugaaaaggug caggccauau    60
ugugcugccu caaaaauaca agg                                           83

<210> SEQ ID NO 249
<211> LENGTH: 89
<212> TYPE: RNA
<213> ORGANISM: Homo sapiens
<220> FEATURE:
<221> NAME/KEY: misc_RNA
<222> LOCATION: (1)..(89)
<223> OTHER INFORMATION: predicted precursor structure: mir-16, 5' to 3'
      sequence

<400> SEQUENCE: 249
gucagcagug ccuuagcagc acguaaauau uggcguuaag auucuaaaau uaucuccagu    60
auuaacugug cugcugaagu aagguugac                                     89

<210> SEQ ID NO 250
<211> LENGTH: 84
<212> TYPE: RNA
<213> ORGANISM: Homo sapiens
<220> FEATURE:
<221> NAME/KEY: misc_RNA
<222> LOCATION: (1)..(84)
<223> OTHER INFORMATION: predicted precursor structure: mir-17, 5' to 3'
      sequence

<400> SEQUENCE: 250
gucagaauaa ugucaaagug cuuacagugc agguagugau augugcaucu acugcaguga    60
aggcacuugu agcauuaugg ugac                                          84

<210> SEQ ID NO 251
<211> LENGTH: 71
<212> TYPE: RNA
<213> ORGANISM: Homo sapiens
<220> FEATURE:
<221> NAME/KEY: misc_RNA
<222> LOCATION: (1)..(71)
<223> OTHER INFORMATION: predicted precursor structure: mir-18, 5' to 3'
      sequence

```
<400> SEQUENCE: 251
uguucuaagg ugcaucuagu gcagauagug aaguagauua gcaucuacug cccuaagugc    60
uccuucuggc a                                                        71

<210> SEQ ID NO 252
<211> LENGTH: 82
<212> TYPE: RNA
<213> ORGANISM: Homo sapiens
<220> FEATURE:
<221> NAME/KEY: misc_RNA
<222> LOCATION: (1)..(82)
<223> OTHER INFORMATION: predicted precursor structure: mir-19a, 5' to
      3' sequence

<400> SEQUENCE: 252
gcagcccucu guuaguuuug cauaguugca cuacaagaag aauguaguug ugcaaaucua    60
ugcaaaacug augguggccu gc                                            82

<210> SEQ ID NO 253
<211> LENGTH: 87
<212> TYPE: RNA
<213> ORGANISM: Homo sapiens
<220> FEATURE:
<221> NAME/KEY: misc_RNA
<222> LOCATION: (1)..(87)
<223> OTHER INFORMATION: predicted precursor structure: mir-19b-1, 5' to
      3' sequence

<400> SEQUENCE: 253
cacuguucua ugguuaguuu ugcagguuug cauccagcug ugugauauuc ugcugugcaa    60
auccaugcaa aacugacugu gguagug                                       87

<210> SEQ ID NO 254
<211> LENGTH: 96
<212> TYPE: RNA
<213> ORGANISM: Homo sapiens
<220> FEATURE:
<221> NAME/KEY: misc_RNA
<222> LOCATION: (1)..(96)
<223> OTHER INFORMATION: predicted precursor structure: 19b-2, 5' to 3'
      sequence

<400> SEQUENCE: 254
acauugcuac uuacaauuag uuuugcaggu uugcauuuca gcguauauau guauaugugg    60
cugugcaaau ccaugcaaaa cugauuguga uaaugu                             96

<210> SEQ ID NO 255
<211> LENGTH: 71
<212> TYPE: RNA
<213> ORGANISM: Homo sapiens
<220> FEATURE:
<221> NAME/KEY: misc_RNA
<222> LOCATION: (1)..(71)
<223> OTHER INFORMATION: predicted precursor structure: mir-20, 5' to 3'
      sequence

<400> SEQUENCE: 255
guagcacuaa agugcuuaua gugcagguag uguuuaguua ucuacugcau uaugagcacu    60
uaaaguacug c                                                        71

<210> SEQ ID NO 256
<211> LENGTH: 72
<212> TYPE: RNA
<213> ORGANISM: Homo sapiens
```

```
<220> FEATURE:
<221> NAME/KEY: misc_RNA
<222> LOCATION: (1)..(72)
<223> OTHER INFORMATION: predicted precursor structure: mir-21, 5' to 3'
      sequence

<400> SEQUENCE: 256
ugucggguag cuuaucagac ugauguugac uguugaaucu cauggcaaca ccagucgaug      60
ggcugucuga ca                                                         72

<210> SEQ ID NO 257
<211> LENGTH: 84
<212> TYPE: RNA
<213> ORGANISM: Homo sapiens
<220> FEATURE:
<221> NAME/KEY: misc_RNA
<222> LOCATION: (1)..(84)
<223> OTHER INFORMATION: predicted precursor structure: mir-22, 5' to 3'
      sequence

<400> SEQUENCE: 257
ggcugagccg caguaguucu ucagugggcaa gcuuuauguc cugacccagc uaaagcugcc     60
aguugaagaa cuguugcccu cugc                                            84

<210> SEQ ID NO 258
<211> LENGTH: 73
<212> TYPE: RNA
<213> ORGANISM: Homo sapiens
<220> FEATURE:
<221> NAME/KEY: misc_RNA
<222> LOCATION: (1)..(73)
<223> OTHER INFORMATION: predicted precursor structure: mir-23, 5' to 3'
      sequence

<400> SEQUENCE: 258
ggccggcugg gguuccuggg gaugggauuu gcuuccuguc acaaaucaca uugccaggga     60
uuuccaaccg acc                                                        73

<210> SEQ ID NO 259
<211> LENGTH: 68
<212> TYPE: RNA
<213> ORGANISM: Homo sapiens
<220> FEATURE:
<221> NAME/KEY: misc_RNA
<222> LOCATION: (1)..(68)
<223> OTHER INFORMATION: predicted precursor structure: mir-24-1, 5' to
      3' sequence

<400> SEQUENCE: 259
cuccggugcc uacugagcug auaucaguuc ucauuuuaca cacuggcuca guucagcagg     60
aacaggag                                                              68

<210> SEQ ID NO 260
<211> LENGTH: 73
<212> TYPE: RNA
<213> ORGANISM: Homo sapiens
<220> FEATURE:
<221> NAME/KEY: misc_RNA
<222> LOCATION: (1)..(73)
<223> OTHER INFORMATION: predicted precursor structure: mir-24-2, 5' to
      3' sequence

<400> SEQUENCE: 260
cucugccucc cgugccuacu gagcugaaac acaguugguu uguguacacu ggcucaguuc     60
agcaggaaca ggg                                                        73
```

-continued

<210> SEQ ID NO 261
<211> LENGTH: 84
<212> TYPE: RNA
<213> ORGANISM: Homo sapiens
<220> FEATURE:
<221> NAME/KEY: misc_RNA
<222> LOCATION: (1)..(84)
<223> OTHER INFORMATION: predicted precursor structure: mir-25, 5' to 3'
      sequence

<400> SEQUENCE: 261
ggccaguguu gagaggcgga gacuugggca auugcuggac gcugcccugg gcauugcacu    60
ugucucgguc ugacagugcc ggcc                                          84

<210> SEQ ID NO 262
<211> LENGTH: 89
<212> TYPE: RNA
<213> ORGANISM: Homo sapiens
<220> FEATURE:
<221> NAME/KEY: misc_RNA
<222> LOCATION: (1)..(89)
<223> OTHER INFORMATION: predicted precursor structure: mir-26a, 5' to
      3' sequence

<400> SEQUENCE: 262 aggccgugge cucguucaag uaauccagga uaggcugugc agguccccaau gggccuauuc    60 uugguuacuu gcacggggac gcgggccuu                                     89

<210> SEQ ID NO 263
<211> LENGTH: 77
<212> TYPE: RNA
<213> ORGANISM: Homo sapiens
<220> FEATURE:
<221> NAME/KEY: misc_RNA
<222> LOCATION: (1)..(77)
<223> OTHER INFORMATION: predicted precursor structure: mir-26b, 5' to
      3' sequence

<400> SEQUENCE: 263
ccgggaccca guucaaguaa uucaggauag guugugugcu guccagccug uucuccauua    60
cuuggcucgg ggaccgg                                                  77

<210> SEQ ID NO 264
<211> LENGTH: 78
<212> TYPE: RNA
<213> ORGANISM: Homo sapiens
<220> FEATURE:
<221> NAME/KEY: misc_RNA
<222> LOCATION: (1)..(78)
<223> OTHER INFORMATION: predicted precursor structure: mir-27, 5' to 3'
      sequence

<400> SEQUENCE: 264
cugaggagca gggcuuagcu gcuugugagc agguccaca ccaagucgug uucacagugg     60
cuaaguuccg cccccccag                                                78

<210> SEQ ID NO 265
<211> LENGTH: 86
<212> TYPE: RNA
<213> ORGANISM: Homo sapiens
<220> FEATURE:
<221> NAME/KEY: misc_RNA
<222> LOCATION: (1)..(86)
<223> OTHER INFORMATION: predicted precursor structure: mir-28, 5' to 3'
      sequence -continued

<400> SEQUENCE: 265
gguccuugcc cucaaggagc ucacagucua uugaguuacc uuucugacuu ucccacuaga    60
uugugagcuc cuggagggca ggcacu                                        86

<210> SEQ ID NO 266
<211> LENGTH: 64
<212> TYPE: RNA
<213> ORGANISM: Homo sapiens
<220> FEATURE:
<221> NAME/KEY: misc_RNA
<222> LOCATION: (1)..(64)
<223> OTHER INFORMATION: predicted precursor structure: mir-29, 5' to 3'
      sequence

<400> SEQUENCE: 266
augacugauu ucuuuggug uucagaguca auauaauuuu cuagcaccau cugaaaucgg    60
uuau                                                                64

<210> SEQ ID NO 267
<211> LENGTH: 71
<212> TYPE: RNA
<213> ORGANISM: Homo sapiens
<220> FEATURE:
<221> NAME/KEY: misc_RNA
<222> LOCATION: (1)..(71)
<223> OTHER INFORMATION: predicted precursor structure: mir-30, 5' to 3'
      sequence

<400> SEQUENCE: 267
gcgacuguaa acauccucga cuggaagcug ugaagccaca gaugggcuuu cagucggaug    60
uuugcagcug c                                                        71

<210> SEQ ID NO 268
<211> LENGTH: 71
<212> TYPE: RNA
<213> ORGANISM: Homo sapiens
<220> FEATURE:
<221> NAME/KEY: misc_RNA
<222> LOCATION: (1)..(71)
<223> OTHER INFORMATION: predicted precursor structure: mir-31, 5' to 3'
      sequence

<400> SEQUENCE: 268
ggagaggagg caagaugcug gcauagcugu ugaacuggga accugcuaug ccaacauauu    60
gccaucuuuc c                                                        71

<210> SEQ ID NO 269
<211> LENGTH: 70
<212> TYPE: RNA
<213> ORGANISM: Homo sapiens
<220> FEATURE:
<221> NAME/KEY: misc_RNA
<222> LOCATION: (1)..(70)
<223> OTHER INFORMATION: predicted precursor structure: mir-32, 5' to 3'
      sequence

<400> SEQUENCE: 269
ggagauauug cacauuacua aguugcaugu ugcacggcc ucaaugcaau uuagugugug    60
ugauauuuuc                                                          70

<210> SEQ ID NO 270
<211> LENGTH: 69
<212> TYPE: RNA

```
<213> ORGANISM: Homo sapiens
<220> FEATURE:
<221> NAME/KEY: misc_RNA
<222> LOCATION: (1)..(69)
<223> OTHER INFORMATION: predicted precursor structure: mir-33, 5' to 3'
      sequence

<400> SEQUENCE: 270
cuguggugca uuguaguugc auugcauguu cuggugguac ccaugcaaug uuuccacagu      60
gcaucacag                                                             69

<210> SEQ ID NO 271
<211> LENGTH: 90
<212> TYPE: RNA
<213> ORGANISM: Mus musculus
<220> FEATURE:
<221> NAME/KEY: misc_RNA
<222> LOCATION: (1)..(90)
<223> OTHER INFORMATION: predicted precursor structure: let-7a-1, 5' to
      3' sequence

<400> SEQUENCE: 271
cacuguggga ugagguagua gguuguauag uuuuaggguc acacccacca cugggagaua      60
acuauacaau cuacugucuu uccuaacgug                                      90

<210> SEQ ID NO 272
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: let-7a-2, 5' to
      3' sequence

<400> SEQUENCE: 272
agguugaggu aguagguugu auaguuuaga auuacaucaa gggagauaac uguacagccu      60
ccuagcuuuc cu                                                         72

<210> SEQ ID NO 273
<211> LENGTH: 74
<212> TYPE: RNA
<213> ORGANISM: Mus musculus
<220> FEATURE:
<221> NAME/KEY: misc_RNA
<222> LOCATION: (1)..(74)
<223> OTHER INFORMATION: predicted precursor structure: let-7a-3, 5' to
      3' sequence

<400> SEQUENCE: 273
gggugaggua guagguugua uaguuugggg cucugcccug cuaugggaua acuauacaau      60
cuacugucuu uccu                                                       74

<210> SEQ ID NO 274
<211> LENGTH: 83
<212> TYPE: RNA
<213> ORGANISM: Mus musculus
<220> FEATURE:
<221> NAME/KEY: misc_RNA
<222> LOCATION: (1)..(83)
<223> OTHER INFORMATION: predicted precursor structure: let-7b, 5' to 3'
      sequence

<400> SEQUENCE: 274
cggggugagg uaguagguug uguggguuca gggcagugau guugcccuc ggaagauaac       60
```

```
uauacaaccu acugccuucc cug                                         83

<210> SEQ ID NO 275
<211> LENGTH: 85
<212> TYPE: RNA
<213> ORGANISM: Mus musculus
<220> FEATURE:
<221> NAME/KEY: misc_RNA
<222> LOCATION: (1)..(85)
<223> OTHER INFORMATION: predicted precursor structure: let-7c, 5' to 3'
      sequence

<400> SEQUENCE: 275
gcauccgggu ugagguagua gguuguaugg uuuagaguua cacccugggg auuaacugua    60
caaccuucua gcuuuccuug gagcg                                         85

<210> SEQ ID NO 276
<211> LENGTH: 87
<212> TYPE: RNA
<213> ORGANISM: Mus musculus
<220> FEATURE:
<221> NAME/KEY: misc_RNA
<222> LOCATION: (1)..(87)
<223> OTHER INFORMATION: predicted precursor structure: let-7d, 5' to 3'
      sequence

<400> SEQUENCE: 276
ccuaggaaga gguaguaggu ugcauaguuu uagggcaggg auuuugccca caaggaggua    60
acuauacgac cugcugccuu ucuuagg                                       87

<210> SEQ ID NO 277
<211> LENGTH: 79
<212> TYPE: RNA
<213> ORGANISM: Mus musculus
<220> FEATURE:
<221> NAME/KEY: misc_RNA
<222> LOCATION: (1)..(79)
<223> OTHER INFORMATION: predicted precursor structure: let-7e, 5' to 3'
      sequence

<400> SEQUENCE: 277
cccgggcuga gguaggaggu uguauaguug aggaggacac ccaaggagau cacuauacgg    60
ccuccuagcu uuccccagg                                                79

<210> SEQ ID NO 278
<211> LENGTH: 87
<212> TYPE: RNA
<213> ORGANISM: Mus musculus
<220> FEATURE:
<221> NAME/KEY: misc_RNA
<222> LOCATION: (1)..(87)
<223> OTHER INFORMATION: predicted precursor structure: let-7f-1, 5' to
      3' sequence

<400> SEQUENCE: 278
ucagagugag guaguagauu guauaguugu ggguaguga uuuuacccug uucaggagau    60
aacuauacaa ucuauugccu ucccuga                                      87

<210> SEQ ID NO 279
<211> LENGTH: 85
<212> TYPE: RNA
<213> ORGANISM: Mus musculus
<220> FEATURE:
<221> NAME/KEY: misc_RNA
<222> LOCATION: (1)..(85)
<223> OTHER INFORMATION: predicted precursor structure: let-7f-2, 5' to
```

-continued

3' sequence

<400> SEQUENCE: 279
cugugggaug agguaguaga uuguauaguu uuagggucau accccaucuu ggagauaacu    60
auacagucua cugucuuucc cacgg                                         85

<210> SEQ ID NO 280
<211> LENGTH: 88
<212> TYPE: RNA
<213> ORGANISM: Mus musculus
<220> FEATURE:
<221> NAME/KEY: misc_RNA
<222> LOCATION: (1)..(88)
<223> OTHER INFORMATION: predicted precursor structure: let-7g, 5' to 3'
      sequence

<400> SEQUENCE: 280
ccaggcugag guaguaguuu guacaguuug agggucuaug auaccacccg guacaggaga    60
uaacuguaca ggccacugcc uugccagg                                      88

<210> SEQ ID NO 281
<211> LENGTH: 85
<212> TYPE: RNA
<213> ORGANISM: Mus musculus
<220> FEATURE:
<221> NAME/KEY: misc_RNA
<222> LOCATION: (1)..(85)
<223> OTHER INFORMATION: predicted precursor structure: let-7i, 5' to 3'
      sequence

<400> SEQUENCE: 281
cuggcugagg uaguaguuug ugcuguuggu cggguuguga cauugcccgc uguggagaua    60
acugcgcaag cuacugccuu gcuag                                         85

<210> SEQ ID NO 282
<211> LENGTH: 91
<212> TYPE: RNA
<213> ORGANISM: Mus musculus
<220> FEATURE:
<221> NAME/KEY: misc_RNA
<222> LOCATION: (1)..(91)
<223> OTHER INFORMATION: predicted precursor structure: mir-1, 5' to 3'
      sequence

<400> SEQUENCE: 282
uucagccuuu gagaguucca ugcuuccuug cauucaauag uuauauucaa gcauauggaa    60
uguaaagaag uauggagcga aaucuggcga g                                  91

<210> SEQ ID NO 283
<211> LENGTH: 79
<212> TYPE: RNA
<213> ORGANISM: Mus musculus
<220> FEATURE:
<221> NAME/KEY: misc_RNA
<222> LOCATION: (1)..(79)
<223> OTHER INFORMATION: predicted precursor structure: mir-1b, 5' to 3'
      sequence

<400> SEQUENCE: 283
uacucagagc acauacuucu uuauguaccc auaugaacau ucagugcuau ggaauguaaa    60
gaaguaugua uuuugggua                                                79

<210> SEQ ID NO 284
<211> LENGTH: 77

```
<212> TYPE: RNA
<213> ORGANISM: Mus musculus
<220> FEATURE:
<221> NAME/KEY: misc_RNA
<222> LOCATION: (1)..(77)
<223> OTHER INFORMATION: predicted precursor structure: mir-1d, 5' to 3'
      sequence

<400> SEQUENCE: 284
gcuugggaca cauacuucuu uauaugccca uaugaaccug cuaagcuaug gaauguaaag      60
aaguauguau uucaggc                                                    77

<210> SEQ ID NO 285
<211> LENGTH: 76
<212> TYPE: RNA
<213> ORGANISM: Mus musculus
<220> FEATURE:
<221> NAME/KEY: misc_RNA
<222> LOCATION: (1)..(76)
<223> OTHER INFORMATION: predicted precursor structure: mir-2a-1, 5' to
      3' sequence

<400> SEQUENCE: 285
gcugggcucu caaagugguu gugaaaugca uuccgcuuu gcgcggcaua ucacagccag       60
cuuugaugag cuuagc                                                     76

<210> SEQ ID NO 286
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-2a-2, 5' to
      3' sequence

<400> SEQUENCE: 286
aucuaagccu caucaagugg uugugauaug gauacccaac gcauaucaca gccagcuuug      60
augagcuagg au                                                         72

<210> SEQ ID NO 287
<211> LENGTH: 77
<212> TYPE: RNA
<213> ORGANISM: Mus musculus
<220> FEATURE:
<221> NAME/KEY: misc_RNA
<222> LOCATION: (1)..(77)
<223> OTHER INFORMATION: predicted precursor structure: mir-2b-1, 5' to
      3' sequence

<400> SEQUENCE: 287
cuucaacugu cuucaaagug gcagugacau guugucaaca auauucauau cacagccagc      60
uuugaggagc guugcgg                                                    77

<210> SEQ ID NO 288
<211> LENGTH: 83
<212> TYPE: RNA
<213> ORGANISM: Mus musculus
<220> FEATURE:
<221> NAME/KEY: misc_RNA
<222> LOCATION: (1)..(83)
<223> OTHER INFORMATION: predicted precursor structure: mir-2b-2, 5' to
      3' sequence

<400> SEQUENCE: 288
uugugucauu cuucaaagug guugugaaau guuugccuuu uuaugccuau ucauaucaca      60
```

```
gccagcuuug aggagcgacg cga                                              83

<210> SEQ ID NO 289
<211> LENGTH: 69
<212> TYPE: RNA
<213> ORGANISM: Mus musculus
<220> FEATURE:
<221> NAME/KEY: misc_RNA
<222> LOCATION: (1)..(69)
<223> OTHER INFORMATION: predicted precursor structure: mir-3, 5' to 3'
      sequence

<400> SEQUENCE: 289
gauccuggga ugcaucuugu gcaguuaugu uucaaucuca caucacuggg caaagugugu      60
cucaagauc                                                              69

<210> SEQ ID NO 290
<211> LENGTH: 82
<212> TYPE: RNA
<213> ORGANISM: Mus musculus
<220> FEATURE:
<221> NAME/KEY: misc_RNA
<222> LOCATION: (1)..(82)
<223> OTHER INFORMATION: predicted precursor structure: mir-4, 5' to 3'
      sequence

<400> SEQUENCE: 290
uugcaauuag uuucuuuggu cguccagccu uagggugauu uuccgguca uaaagcuaga      60 caaccauuga aguucguugu gg                                              82

<210> SEQ ID NO 291
<211> LENGTH: 69
<212> TYPE: RNA
<213> ORGANISM: Mus musculus
<220> FEATURE:
<221> NAME/KEY: misc_RNA
<222> LOCATION: (1)..(69)
<223> OTHER INFORMATION: predicted precursor structure: mir-5, 5' to 3'
      sequence

<400> SEQUENCE: 291
gcuaaaagga acgaucguug ugauaugagu uguuuccuaa cauaucacag ugauuuuccu      60
uuauaacgc                                                              69

<210> SEQ ID NO 292
<211> LENGTH: 81
<212> TYPE: RNA
<213> ORGANISM: Mus musculus
<220> FEATURE:
<221> NAME/KEY: misc_RNA
<222> LOCATION: (1)..(81)
<223> OTHER INFORMATION: predicted precursor structure: mir-6-1, 5' to
      3' sequence

<400> SEQUENCE: 292
uuuaauguag agggaauagu ugcugugcug uaaguuaaua uaccauaucu auaucacagg      60
gcuguucuuu uuguaccuaa a                                               81

<210> SEQ ID NO 293
<211> LENGTH: 74
<212> TYPE: RNA
<213> ORGANISM: Mus musculus
<220> FEATURE:
<221> NAME/KEY: misc_RNA
<222> LOCATION: (1)..(74)
```

```
<223> OTHER INFORMATION: predicted precursor structure: mir-6-2, 5' to
      3' sequence

<400> SEQUENCE: 293 uacccaagg  gaacuucugc  ugcugauaua  uuauugaaaa  acuacuauau  cacaguggcu     60 guucuuuug  guug                                                          74

<210> SEQ ID NO 294
<211> LENGTH: 79
<212> TYPE: RNA
<213> ORGANISM: Mus musculus
<220> FEATURE:
<221> NAME/KEY: misc_RNA
<222> LOCATION: (1)..(79)
<223> OTHER INFORMATION: predicted precursor structure: mir-6-3, 5' to
      3' sequence

<400> SEQUENCE: 294 caaaagaag  ggaacgguug  cugaugaugu  aguuugaaac  ucucacaauu  uauaucacag     60
uggcuguucu  uuuuguuug                                                    79

<210> SEQ ID NO 295
<211> LENGTH: 88
<212> TYPE: RNA
<213> ORGANISM: Mus musculus
<220> FEATURE:
<221> NAME/KEY: misc_RNA
<222> LOCATION: (1)..(88)
<223> OTHER INFORMATION: predicted precursor structure: mir-7, 5' to 3'
      sequence

<400> SEQUENCE: 295
gagugcauuc  cguauggaag  acuagugauu  uguuguuug  gucuuuggua  auaacaauaa     60 auccccuuguc  uucuuacggc  gugcauuu                                        88

<210> SEQ ID NO 296
<211> LENGTH: 87
<212> TYPE: RNA
<213> ORGANISM: Mus musculus
<220> FEATURE:
<221> NAME/KEY: misc_RNA
<222> LOCATION: (1)..(87)
<223> OTHER INFORMATION: predicted precursor structure: mir-8, 5' to 3'
      sequence

<400> SEQUENCE: 296
aaggacaucu  guucacaucu  uaccgggcag  cauuagaucc  uuuuuauaac  ucuaauacug    60
ucagguaaag  augucguccg  ugccuu                                           87

<210> SEQ ID NO 297
<211> LENGTH: 78
<212> TYPE: RNA
<213> ORGANISM: Mus musculus
<220> FEATURE:
<221> NAME/KEY: misc_RNA
<222> LOCATION: (1)..(78)
<223> OTHER INFORMATION: predicted precursor structure: mir-9, 5' to 3'
      sequence

<400> SEQUENCE: 297
gcuauguugu  cuuugguuau  cuagcuguau  gagugauaaa  uaacgucaua  aagcuagcuu    60
accgaaguua  auauuagc                                                     78

<210> SEQ ID NO 298
```

```
<211> LENGTH: 77
<212> TYPE: RNA
<213> ORGANISM: Mus musculus
<220> FEATURE:
<221> NAME/KEY: misc_RNA
<222> LOCATION: (1)..(77)
<223> OTHER INFORMATION: predicted precursor structure: mir-10, 5' to 3'
      sequence

<400> SEQUENCE: 298
ccacgucuac ccuguagauc cgaauuuguu uuauacuagc uuuaaggaca aauucgguuc        60
uagagagguu ugugugg                                                      77

<210> SEQ ID NO 299
<211> LENGTH: 75
<212> TYPE: RNA
<213> ORGANISM: Mus musculus
<220> FEATURE:
<221> NAME/KEY: misc_RNA
<222> LOCATION: (1)..(75)
<223> OTHER INFORMATION: predicted precursor structure: mir-11, 5' to 3'
      sequence

<400> SEQUENCE: 299
gcacuuguca agaacuuucu cugugacccg cguguacuua aaagccgcau cacagucuga        60
guucuugcug agugc                                                        75

<210> SEQ ID NO 300
<211> LENGTH: 74
<212> TYPE: RNA
<213> ORGANISM: Mus musculus
<220> FEATURE:
<221> NAME/KEY: misc_RNA
<222> LOCATION: (1)..(74)
<223> OTHER INFORMATION: predicted precursor structure: mir-12, 5' to 3'
      sequence

<400> SEQUENCE: 300
uacgguugag uauuacauca gguacuggug ugccuuaaau ccaacaacca guacuuaugu        60
cauacuacgc cgug                                                         74

<210> SEQ ID NO 301
<211> LENGTH: 75
<212> TYPE: RNA
<213> ORGANISM: Mus musculus
<220> FEATURE:
<221> NAME/KEY: misc_RNA
<222> LOCATION: (1)..(75)
<223> OTHER INFORMATION: predicted precursor structure: mir-13a, 5' to
      3' sequence

<400> SEQUENCE: 301
uacguaacuc cucaaagggu ugugaaaugu cgacuauuau cuacucauau cacagccauu        60
uugaugaguu ucgug                                                        75

<210> SEQ ID NO 302
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-13b-1, 5' to
      3' sequence

<400> SEQUENCE: 302
```

```
ccaugucguu aaaauguuug ugaacuuaug uauucacaau cauaucacag ccauuuugac      60
gaguuugg                                                               68

<210> SEQ ID NO 303
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-13b-2, 5' to
      3' sequence

<400> SEQUENCE: 303
uauuaacgcg ucaaaaugac ugugagcuau guggauuuga cuucauauca cagccauuuu      60
gacgaguuug                                                             70

<210> SEQ ID NO 304
<211> LENGTH: 65
<212> TYPE: RNA
<213> ORGANISM: Mus musculus
<220> FEATURE:
<221> NAME/KEY: misc_RNA
<222> LOCATION: (1)..(65)
<223> OTHER INFORMATION: predicted precursor structure: mir-14, 5' to 3'
      sequence

<400> SEQUENCE: 304
ugugggagcg agacguggga cucacugugc uuauuaaaua gucagucuug uuucucucuc      60
cuaua                                                                  65

<210> SEQ ID NO 305
<211> LENGTH: 83
<212> TYPE: RNA
<213> ORGANISM: Mus musculus
<220> FEATURE:
<221> NAME/KEY: misc_RNA
<222> LOCATION: (1)..(83)
<223> OTHER INFORMATION: predicted precursor structure: mir-15a, 5' to
      3' sequence

<400> SEQUENCE: 305
ccuuggagua aaguagcagc acauaauggu uuguggauuu ugaaaaggug caggccauau      60
ugugcugccu caaaaauaca agg                                              83

<210> SEQ ID NO 306
<211> LENGTH: 64
<212> TYPE: RNA
<213> ORGANISM: Mus musculus
<220> FEATURE:
<221> NAME/KEY: misc_RNA
<222> LOCATION: (1)..(64)
<223> OTHER INFORMATION: predicted precursor structure: mir-15b, 5' to
      3' sequence

<400> SEQUENCE: 306
cuguagcagc acaucauggu uuacauacua cagucaagau gcgaaucauu auuugcugcu      60
cuag                                                                   64

<210> SEQ ID NO 307
<211> LENGTH: 89
<212> TYPE: RNA
<213> ORGANISM: Mus musculus
<220> FEATURE:
<221> NAME/KEY: misc_RNA
```

```
<222> LOCATION: (1)..(89)
<223> OTHER INFORMATION: predicted precursor structure: mir-16, 5' to 3'
      sequence

<400> SEQUENCE: 307
gucagcagug ccuuagcagc acguaaauau uggcguuaag auucuaaaau uaucuccagu    60
auuaacugug cugcugaagu aagguugac                                     89

<210> SEQ ID NO 308
<211> LENGTH: 81
<212> TYPE: RNA
<213> ORGANISM: Mus musculus
<220> FEATURE:
<221> NAME/KEY: misc_RNA
<222> LOCATION: (1)..(81)
<223> OTHER INFORMATION: predicted precursor structure: mir-16, 5' to 3'
      sequence

<400> SEQUENCE: 308
guuccacucu agcagcacgu aaauauuggc guagugaaau auauauuaaa caccaauauu    60
acugugcugc uuuaguguga c                                             81

<210> SEQ ID NO 309
<211> LENGTH: 84
<212> TYPE: RNA
<213> ORGANISM: Mus musculus
<220> FEATURE:
<221> NAME/KEY: misc_RNA
<222> LOCATION: (1)..(84)
<223> OTHER INFORMATION: predicted precursor structure: mir-17, 5' to 3'
      sequence

<400> SEQUENCE: 309
gucagaauaa ugucaaagug cuuacagugc agguagugau augugcaucu acugcaguga    60
aggcacuugu agcauuaugg ugac                                          84

<210> SEQ ID NO 310
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-18, 5' to 3'
      sequence

<400> SEQUENCE: 310
uguucuaagg ugcaucuagu gcagauagug aaguagauua gcaucuacug cccuaagugc    60
uccuucuggc a                                                        71

<210> SEQ ID NO 311
<211> LENGTH: 82
<212> TYPE: RNA
<213> ORGANISM: Mus musculus
<220> FEATURE:
<221> NAME/KEY: misc_RNA
<222> LOCATION: (1)..(82)
<223> OTHER INFORMATION: predicted precursor structure: mir-19a, 5' to
      3' sequence

<400> SEQUENCE: 311
gcaguccucu guuaguuuug cauaguugca cuacaagaag aauguaguug ugcaaaucua    60
ugcaaaacug augguggccu gc                                            82
```

```
<210> SEQ ID NO 312
<211> LENGTH: 87
<212> TYPE: RNA
<213> ORGANISM: Mus musculus
<220> FEATURE:
<221> NAME/KEY: misc_RNA
<222> LOCATION: (1)..(87)
<223> OTHER INFORMATION: predicted precursor structure: mir-19b-1, 5' to
      3' sequence

<400> SEQUENCE: 312
cacuguucua ugguuaguuu ugcagguuug cauccagcug ugugauauuc ugcugugcaa      60
auccaugcaa aacugacugu gguagug                                         87

<210> SEQ ID NO 313
<211> LENGTH: 96
<212> TYPE: RNA
<213> ORGANISM: Mus musculus
<220> FEATURE:
<221> NAME/KEY: misc_RNA
<222> LOCATION: (1)..(96)
<223> OTHER INFORMATION: predicted precursor structure: mir-19b-2, 5' to
      3' sequence

<400> SEQUENCE: 313
acauugcuac uuacaauuag uuuugcaggu uugcauuuca gcguauauau guauaugugg      60
cugugcaaau ccaugcaaaa cugauuguga uaaugu                               96

<210> SEQ ID NO 314
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-20, 5' to 3'
      sequence

<400> SEQUENCE: 314
guagcacuaa agugcuuaua gugcagguag uguuuaguua ucuacugcau uaugagcacu      60
uaaaguacug c                                                          71

<210> SEQ ID NO 315
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-21, 5' to 3'
      sequence

<400> SEQUENCE: 315
ugucggguag cuuaucagac ugauguugac uguugaaucu cauggcaaca ccagucgaug      60
ggcugucuga ca                                                         72

<210> SEQ ID NO 316
<211> LENGTH: 85
<212> TYPE: RNA
<213> ORGANISM: Mus musculus
<220> FEATURE:
<221> NAME/KEY: misc_RNA
<222> LOCATION: (1)..(85)
<223> OTHER INFORMATION: predicted precursor structure: mir-22, 5' to 3'
      sequence

<400> SEQUENCE: 316
```

```
ggcugagccg caguaguucu ucaguggcaa gcuuuauguc cugacccagc uaaagcugcc    60
aguugaagaa cuguugcccu cugcc                                          85
```

<210> SEQ ID NO 317
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-23a, 5' to
      3' sequence

<400> SEQUENCE: 317

```
ggccggcugg gguuccuggg gaugggauuu gcuuccuguc acaaaucaca uugccaggga    60
uuuccaaccg acc                                                       73
```

<210> SEQ ID NO 318
<211> LENGTH: 74
<212> TYPE: RNA
<213> ORGANISM: Mus musculus
<220> FEATURE:
<221> NAME/KEY: misc_RNA
<222> LOCATION: (1)..(74)
<223> OTHER INFORMATION: predicted precursor structure: mir-23b, 5' to
      3' sequence

<400> SEQUENCE: 318

```
ggcugcuugg guuccuggca ugcugauuug ugacuugaga uuaaaaucac auugccaggg    60
auuaccacgc aacc                                                      74
```

<210> SEQ ID NO 319
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-24-1, 5' to
      3' sequence

<400> SEQUENCE: 319

```
cuccggugcc uacugagcug auaucaguuc ucauuuuaca cacuggcuca guucagcagg    60
aacaggag                                                             68
```

<210> SEQ ID NO 320
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-24-2, 5' to
      3' sequence

<400> SEQUENCE: 320

```
cucugccucc cgugccuacu gagcugaaac acaguugguu uguguacacu ggcucaguuc    60
agcaggaaca ggg                                                       73
```

<210> SEQ ID NO 321
<211> LENGTH: 84
<212> TYPE: RNA
<213> ORGANISM: Mus musculus
<220> FEATURE:

```
<221> NAME/KEY: misc_RNA
<222> LOCATION: (1)..(84)
<223> OTHER INFORMATION: predicted precursor structure: mir-25, 5' to 3'
      sequence

<400> SEQUENCE: 321
ggccaguguu gagaggcgga gacuugggca auugcuggac gcugcccugg gcauugcacu    60
ugucucgguc ugacagugcc ggcc                                          84

<210> SEQ ID NO 322
<211> LENGTH: 86
<212> TYPE: RNA
<213> ORGANISM: Mus musculus
<220> FEATURE:
<221> NAME/KEY: misc_RNA
<222> LOCATION: (1)..(86)
<223> OTHER INFORMATION: predicted precursor structure: mir-26a, 5' to
      3' sequence

<400> SEQUENCE: 322
aggccguggc cucguucaag uaauccagga uaggcugugc aggucccaau ggccuaucuu    60
gguuacuugc acggggacgc gggccu                                        86

<210> SEQ ID NO 323
<211> LENGTH: 77
<212> TYPE: RNA
<213> ORGANISM: Mus musculus
<220> FEATURE:
<221> NAME/KEY: misc_RNA
<222> LOCATION: (1)..(77)
<223> OTHER INFORMATION: predicted precursor structure: mir-26b, 5' to
      3' sequence

<400> SEQUENCE: 323
ccgggaccca guucaaguaa uucaggauag guguguugcu guccagccug uucuccauua    60
cuuggcucgg ggaccgg                                                  77

<210> SEQ ID NO 324
<211> LENGTH: 78
<212> TYPE: RNA
<213> ORGANISM: Mus musculus
<220> FEATURE:
<221> NAME/KEY: misc_RNA
<222> LOCATION: (1)..(78)
<223> OTHER INFORMATION: predicted precursor structure: mir-27a, 5' to
      3' sequence

<400> SEQUENCE: 324
cugaggagca gggcuuagcu gcuugugagc aggguccaca ccaagucgug uucacagugg    60
cuaaguuccg cccccccag                                                78

<210> SEQ ID NO 325
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-27b, 5' to
      3' sequence

<400> SEQUENCE: 325
aggugcagag cuuagcugau uggugaacag ugauugguuu ccgcuuuguu cacaguggcu    60
aaguucugca ccu                                                      73
```

```
<210> SEQ ID NO 326
<211> LENGTH: 86
<212> TYPE: RNA
<213> ORGANISM: Mus musculus
<220> FEATURE:
<221> NAME/KEY: misc_RNA
<222> LOCATION: (1)..(86)
<223> OTHER INFORMATION: predicted precursor structure: mir-28, 5' to 3'
      sequence

<400> SEQUENCE: 326 ggccuugcc cucaaggagc ucacagucua uugaguuacc uuucugacuu ucccacuaga        60
uugugagcuc cuggagggca ggcacu                                           86

<210> SEQ ID NO 327
<211> LENGTH: 64
<212> TYPE: RNA
<213> ORGANISM: Mus musculus
<220> FEATURE:
<221> NAME/KEY: misc_RNA
<222> LOCATION: (1)..(64)
<223> OTHER INFORMATION: predicted precursor structure: mir-29a, 5' to
      3' sequence

<400> SEQUENCE: 327
augacugauu ucuuuggug uucagaguca auauaauuuu cuagcaccau cugaaaucgg        60
uuau                                                                   64

<210> SEQ ID NO 328
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-29b, 5' to
      3' sequence

<400> SEQUENCE: 328
aggaagcugg uuucauaugg ugguuuagau uuaaauagug auugcuagc accauuugaa        60 aucaguguuc u                                                           71

<210> SEQ ID NO 329
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-30a-s, 5' to
      3' sequence

<400> SEQUENCE: 329
gcgacuguaa acauccucga cuggaagcug ugaagccaca aaugggcuuu cagucggaug       60
uuugcagcug c                                                           71

<210> SEQ ID NO 330
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-30a-as, 5'
      to 3' sequence
```

-continued

```
<400> SEQUENCE: 330
gcgacuguaa acauccucga cuggaagcug ugaagccaca aaugggcuuu cagucggaug    60
uuugcagcug c                                                         71

<210> SEQ ID NO 331
<211> LENGTH: 60
<212> TYPE: RNA
<213> ORGANISM: Mus musculus
<220> FEATURE:
<221> NAME/KEY: misc_RNA
<222> LOCATION: (1)..(60)
<223> OTHER INFORMATION: predicted precursor structure: mir-30b, 5' to
      3' sequence

<400> SEQUENCE: 331
auguaaacau ccuacacuca gcugucauac augcguuggc ugggaugugg auguuuacgu    60

<210> SEQ ID NO 332
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-30c, 5' to
      3' sequence

<400> SEQUENCE: 332
agauacugua aacauccuac acucucagcu guggaaagua agaaagcugg gagaaggcug    60
uuuacucuuu cu                                                        72

<210> SEQ ID NO 333
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-30d, 5' to
      3' sequence

<400> SEQUENCE: 333
guuguuguaa caucccccga cuggaagcug uaagacacag cuaagcuuuc agucagaugu    60
uugcugcuac                                                           70

<210> SEQ ID NO 334
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-31, 5' to 3'
      sequence

<400> SEQUENCE: 334
ggagaggagg caagaugcug gcauagcugu ugaacgggga accugcuaug ccaacauauu    60
gccaucuuuc c                                                         71

<210> SEQ ID NO 335
<211> LENGTH: 70
<212> TYPE: RNA
<213> ORGANISM: Mus musculus
<220> FEATURE:
<221> NAME/KEY: misc_RNA
```

```
<222> LOCATION: (1)..(70)
<223> OTHER INFORMATION: predicted precursor structure: mir-32, 5' to 3'
      sequence

<400> SEQUENCE: 335
ggagauauug cacauuacua aguugcaugu ugucacggcc ucaaugcaau uuagugugug    60
ugauauuuuc                                                           70

<210> SEQ ID NO 336
<211> LENGTH: 69
<212> TYPE: RNA
<213> ORGANISM: Mus musculus
<220> FEATURE:
<221> NAME/KEY: misc_RNA
<222> LOCATION: (1)..(69)
<223> OTHER INFORMATION: predicted precursor structure: mir-33, 5' to 3'
      sequence

<400> SEQUENCE: 336
cuguggugca uuguaguugc auugcauguu cuggugguac ccaugcaaug uuccacagu     60 gcaucacag                                                            69

<210> SEQ ID NO 337
<211> LENGTH: 65
<212> TYPE: RNA
<213> ORGANISM: Mus musculus
<220> FEATURE:
<221> NAME/KEY: misc_RNA
<222> LOCATION: (1)..(65)
<223> OTHER INFORMATION: predicted precursor structure: mir-99a, 5' to
      3' sequence

<400> SEQUENCE: 337
cauaaacccg uagauccgau cuugugguga aguggaccgc gcaagcucgu uucuaugggu    60
cugug                                                                65

<210> SEQ ID NO 338
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-99b, 5' to
      3' sequence

<400> SEQUENCE: 338
ggcacccacc cguagaaccg accuugcggg gccuucgccg cacacaagcu cgucucugug    60
gguccguguc                                                           70

<210> SEQ ID NO 339
<211> LENGTH: 57
<212> TYPE: RNA
<213> ORGANISM: Mus musculus
<220> FEATURE:
<221> NAME/KEY: misc_RNA
<222> LOCATION: (1)..(57)
<223> OTHER INFORMATION: predicted precursor structure: mir-101, 5' to
      3' sequence

<400> SEQUENCE: 339
ucaguuauca cagugcugau gcuguccauu cuaaaggua aguacuguga uaacuga        57

<210> SEQ ID NO 340
<211> LENGTH: 66
```

```
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-122a, 5' to
      3' sequence

<400> SEQUENCE: 340
agcuguggag ugugacaaug guguuugugu ccaaaccauc aaacgccauu aucacacuaa    60
auagcu                                                              66

<210> SEQ ID NO 341
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-123, 5' to
      3' sequence

<400> SEQUENCE: 341
ugacagcaca uuauuacuuu ugguacgcgc ugugacacuu caaacucgua ccgugaguaa    60
uaaugcgcgg uca                                                      73

<210> SEQ ID NO 342
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-124a, 5' to
      3' sequence
<220> FEATURE:
<221> NAME/KEY: misc_RNA
<222> LOCATION: (1)..(68)
<223> OTHER INFORMATION: predicted precursor structure: mir-124a*, 5' to
      3' sequence

<400> SEQUENCE: 342
cucugcgugu ucacagcgga ccuugauuua augucuauac aauuaaggca cgcggugaau    60
gccaagag                                                            68

<210> SEQ ID NO 343
<211> LENGTH: 67
<212> TYPE: RNA
<213> ORGANISM: Mus musculus
<220> FEATURE:
<221> NAME/KEY: misc_RNA
<222> LOCATION: (1)..(67)
<223> OTHER INFORMATION: predicted precursor structure: mir-124b, 5' to
      3' sequence

<400> SEQUENCE: 343
cucuccgugu ucacagcgga ccuugauuua augucauaca auuaaggcac gcggugaaug    60
ccaagag                                                             67

<210> SEQ ID NO 344
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-125a, 5' to
```

3' sequence

<400> SEQUENCE: 344 cuggucccu gagacccuuu aaccugugag gacguccagg gucacaggug agguucuugg     60
gagccugg                                                             68

<210> SEQ ID NO 345
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-125b, 5' to
      3' sequence

<400> SEQUENCE: 345 gccuagucc ugagacccua acuugugagg uauuuuagua acaucacaag ucagguucuu     60
gggaccuagg c                                                         71

<210> SEQ ID NO 346
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-126, 5' to
      3' sequence

<400> SEQUENCE: 346
ugacagcaca uuauuacuuu ugguacgcgc ugugacacuu caaacucgua ccgugaguaa     60
uaaugcgcgg uca                                                       73

<210> SEQ ID NO 347
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-127, 5' to
      3' sequence

<400> SEQUENCE: 347
ccagccugcu gaagcucaga gggcucugau ucagaaagau caucggaucc gucugagcuu     60
ggcuggucgg                                                           70

<210> SEQ ID NO 348
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-128, 5' to
      3' sequence

<400> SEQUENCE: 348
guuggauucg gggccguagc acugucugag agguuuacau uucucacagu gaaccggucu     60
cuuuuucagc                                                           70

<210> SEQ ID NO 349
<211> LENGTH: 72

```
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-129, 5' to
      3' sequence

<400> SEQUENCE: 349
ggaucuuuuu gcggucuggg cuugcuguuc cucucaacag uagucaggaa gcccuuaccc      60
caaaaaguau cu                                                         72

<210> SEQ ID NO 350
<211> LENGTH: 64
<212> TYPE: RNA
<213> ORGANISM: Mus musculus
<220> FEATURE:
<221> NAME/KEY: misc_RNA
<222> LOCATION: (1)..(64)
<223> OTHER INFORMATION: predicted precursor structure: mir-130, 5' to
      3' sequence

<400> SEQUENCE: 350
gagcucuuuu cacauugugc uacugucuaa cguguaccga gcagugcaau guuaaaaggg      60
cauc                                                                  64

<210> SEQ ID NO 351
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-131, 5' to
      3' sequence

<400> SEQUENCE: 351
guuguuaucu uugguuaucu agcuguauga guguauuggu cuucauaaag cuagauaacc      60
gaaaguaaaa ac                                                         72

<210> SEQ ID NO 352
<211> LENGTH: 66
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-132, 5' to
      3' sequence

<400> SEQUENCE: 352
gggcaaccgu ggcuuucgau uguuacugug ggaaccggag guaacagucu acagccaugg      60
ucgccc                                                                66

<210> SEQ ID NO 353
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-133, 5' to
      3' sequence

<400> SEQUENCE: 353
gcuaaagcug guaaaaugga accaaaucgc cucuucaaug gauuuggucc ccuucaacca      60
``` gcuguagc                                                              68

<210> SEQ ID NO 354
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-134, 5' to
      3' sequence

<400> SEQUENCE: 354
agggugugug acugguugac cagaggggcg ugcacucugu ucacccugug ggccaccuag    60
ucaccaaccc u                                                          71

<210> SEQ ID NO 355
<211> LENGTH: 60
<212> TYPE: RNA
<213> ORGANISM: Mus musculus
<220> FEATURE:
<221> NAME/KEY: misc_RNA
<222> LOCATION: (1)..(60)
<223> OTHER INFORMATION: predicted precursor structure: mir-135, 5' to
      3' sequence

<400> SEQUENCE: 355
cuauggcuuu uuauuccuau gugauucuau ugcucgcuca uauagggauu ggagccgugg    60

<210> SEQ ID NO 356
<211> LENGTH: 62
<212> TYPE: RNA
<213> ORGANISM: Mus musculus
<220> FEATURE:
<221> NAME/KEY: misc_RNA
<222> LOCATION: (1)..(62)
<223> OTHER INFORMATION: predicted precursor structure: mir-136, 5' to
      3' sequence

<400> SEQUENCE: 356
gaggacucca uuuguuuuga ugauggauuc uuaagcucca ucaucgucuc aaaugagucu    60
uc                                                                    62

<210> SEQ ID NO 357
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-137, 5' to
      3' sequence

<400> SEQUENCE: 357
cuucggugac ggguauucuu gggugggauaa uacggauuac guuguuauug cuuaagaaua    60
cgcguagucg agg                                                        73

<210> SEQ ID NO 358
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: mir-138, 5' to
      3' sequence

```
<400> SEQUENCE: 358
cagcuggugu ugugaaucag gccgacgagc agcgcauccu cuuacccggc uauuucacga      60 caccagdgguu g                                                         71

<210> SEQ ID NO 359
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-139, 5' to
      3' sequence

<400> SEQUENCE: 359
guguauucua cagugcacgu gucuccagug uggcucggag gcuggagacg cggcccuguu      60
ggaguaac                                                              68

<210> SEQ ID NO 360
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-140, 5' to
      3' sequence

<400> SEQUENCE: 360
ccugccagug guuuuacccu augguagguu acgucaugcu guucuaccac aggguagaac      60
cacggacagg                                                            70

<210> SEQ ID NO 361
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-141, 5' to
      3' sequence

<400> SEQUENCE: 361
ggguccaucu uccagugcag uguuggaugg uugaaguaug aagcccuaa cacugucugg       60 uaaagauggc cc                                                         72

<210> SEQ ID NO 362
<211> LENGTH: 64
<212> TYPE: RNA
<213> ORGANISM: Mus musculus
<220> FEATURE:
<221> NAME/KEY: misc_RNA
<222> LOCATION: (1)..(64)
<223> OTHER INFORMATION: predicted precursor structure: mir-142s, 5' to
      3' sequence

<400> SEQUENCE: 362
acccauaaag uagaaagcac uacuaacagc acuggagggu guaguguuuc cuacuuuaug      60
gaug                                                                  64

<210> SEQ ID NO 363
<211> LENGTH: 64
<212> TYPE: RNA
```

```
<213> ORGANISM: Mus musculus
<220> FEATURE:
<221> NAME/KEY: misc_RNA
<222> LOCATION: (1)..(64)
<223> OTHER INFORMATION: predicted precursor structure: mir-142as*, 5'
      to 3' sequence

<400> SEQUENCE: 363
acccauaaag uagaaagcac uacuaacagc acuggagggu guaguguuuc cuacuuuaug    60
gaug                                                                 64

<210> SEQ ID NO 364
<211> LENGTH: 71
<212> TYPE: RNA
<213> ORGANISM: Mus musculus
<220> FEATURE:
<221> NAME/KEY: misc_RNA
<222> LOCATION: (1)..(71)
<223> OTHER INFORMATION: predicted precursor structure: new, 5' to 3'
      sequence

<400> SEQUENCE: 364
ugacgggcga gcuuuuggcc cggguuauac cugaugcuca cguauaagac gagcaaaaag    60
cuuguugguc a                                                         71

<210> SEQ ID NO 365
<211> LENGTH: 63
<212> TYPE: RNA
<213> ORGANISM: Mus musculus
<220> FEATURE:
<221> NAME/KEY: misc_RNA
<222> LOCATION: (1)..(63)
<223> OTHER INFORMATION: predicted precursor structure: mir-143, 5' to
      3' sequence

<400> SEQUENCE: 365
ccugaggugc agugcugcau cucuggucag uugggagucu gagaugaagc acuguagcuc    60
agg                                                                  63

<210> SEQ ID NO 366
<211> LENGTH: 66
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-144, 5' to
      3' sequence

<400> SEQUENCE: 366
ggcugggaua ucaucauaua cuguaaguuu gugaugagac acuacaguau agaugaugua    60
cuaguc                                                               66

<210> SEQ ID NO 367
<211> LENGTH: 70
<212> TYPE: RNA
<213> ORGANISM: Mus musculus
<220> FEATURE:
<221> NAME/KEY: misc_RNA
<222> LOCATION: (1)..(70)
<223> OTHER INFORMATION: predicted precursor structure: mir-145, 5' to
      3' sequence

<400> SEQUENCE: 367
cucacggucc aguuuuccca ggaauccccuu ggaugcuaag auggggauuc cuggaaauac    60
```
uguucuugag 70

<210> SEQ ID NO 368
<211> LENGTH: 65
<212> TYPE: RNA
<213> ORGANISM: Mus musculus
<220> FEATURE:
<221> NAME/KEY: misc_RNA
<222> LOCATION: (1)..(65)
<223> OTHER INFORMATION: predicted precursor structure: mir-146, 5' to
      3' sequence

<400> SEQUENCE: 368
agcucugaga acugaauucc auggguuaua ucaaugucag accugugaaa uucaguucuu    60
cagcu                                                                65

<210> SEQ ID NO 369
<211> LENGTH: 72
<212> TYPE: RNA
<213> ORGANISM: Mus musculus
<220> FEATURE:
<221> NAME/KEY: misc_RNA
<222> LOCATION: (1)..(72)
<223> OTHER INFORMATION: predicted precursor structure: mir-147, 5' to
      3' sequence

<400> SEQUENCE: 369
aaucuaaaga caacauuucu gcacacacac cagacuaugg aagccagugu guggaaaugc    60
uucugcuaga uu                                                        72

<210> SEQ ID NO 370
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precusor structure: mir-148, 5' to 3'
      sequence

<400> SEQUENCE: 370
gaggcaaagu ucugagacac uccgacucug aguaugauag aagucagugc acuacagaac    60
uuugucuc                                                             68

<210> SEQ ID NO 371
<211> LENGTH: 66
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-149, 5' to
      3' sequence

<400> SEQUENCE: 371
ggcucuggcu ccgugucuuc acucccgugu uuguccgagg agggagggag ggacagaggc    60
ggggcu                                                               66

<210> SEQ ID NO 372
<211> LENGTH: 65
<212> TYPE: RNA
<213> ORGANISM: Mus musculus
<220> FEATURE:
<221> NAME/KEY: misc_RNA
<222> LOCATION: (1)..(65)
<223> OTHER INFORMATION: predicted precursor structure: mir-150, 5' to -continued 3' sequence

<400> SEQUENCE: 372
cccugucucc aacccuugu accagugcug ugccucagac ccugguacag gccuggggga    60
uaggg                                                                65

<210> SEQ ID NO 373
<211> LENGTH: 68
<212> TYPE: RNA
<213> ORGANISM: Mus musculus
<220> FEATURE:
<221> NAME/KEY: misc_RNA
<222> LOCATION: (1)..(68)
<223> OTHER INFORMATION: predicted precursor structure: mir-151, 5' to
      3' sequence

<400> SEQUENCE: 373
ccugcccucg aggagcucac agucuaguau gucuccuccc uacuagacug aggcuccuug    60
aggacagg                                                             68

<210> SEQ ID NO 374
<211> LENGTH: 73
<212> TYPE: RNA
<213> ORGANISM: Mus musculus
<220> FEATURE:
<221> NAME/KEY: misc_RNA
<222> LOCATION: (1)..(73)
<223> OTHER INFORMATION: predicted precursor structure: mir-152, 5' to
      3' sequence

<400> SEQUENCE: 374
ccgggccuag guucugugau acacuccgac ucgggcucug gagcagucag ugcaugacag    60
aacuugggcc cgg                                                       73

<210> SEQ ID NO 375
<211> LENGTH: 69
<212> TYPE: RNA
<213> ORGANISM: Mus musculus
<220> FEATURE:
<221> NAME/KEY: misc_RNA
<222> LOCATION: (1)..(69)
<223> OTHER INFORMATION: predicted precursor structure: mir-153, 5' to
      3' sequence

<400> SEQUENCE: 375
cagugucauu uuugugaugu ugcagcuagu aauaugagcc caguugcaua gucacaaaag    60
ugaucauug                                                            69

<210> SEQ ID NO 376
<211> LENGTH: 66
<212> TYPE: RNA
<213> ORGANISM: Mus musculus
<220> FEATURE:
<221> NAME/KEY: misc_RNA
<222> LOCATION: (1)..(66)
<223> OTHER INFORMATION: predicted precursor structure: mir-154, 5' to
      3' sequence

<400> SEQUENCE: 376
gaagauaggu uauccguguu gccuucgcuu uauuugugac gaaucauaca cgguugaccu    60
auuuuu                                                               66

<210> SEQ ID NO 377
<211> LENGTH: 65

```
<212> TYPE: RNA
<213> ORGANISM: Mus musculus
<220> FEATURE:
<221> NAME/KEY: mice_RNA
<222> LOCATION: (1)..(65)
<223> OTHER INFORMATION: predicted precursor structure: mir-155
      (BIC-RNA), 5' to 3' sequence

<400> SEQUENCE: 377 cguuaaugc uaauugugau aggguuuug gccucugacu gacuccuacc uguuagcauu    60
aacag                                                              65

<210> SEQ ID NO 378
<211> LENGTH: 76
<212> TYPE: RNA
<213> ORGANISM: Homo sapiens and Mus musculus
<220> FEATURE:
<221> NAME/KEY: misc_RNA
<222> LOCATION: (1)..(76)
<223> OTHER INFORMATION: predicted precursor structure: mir-C1, 5' to 3'
      sequence

<400> SEQUENCE: 378
ccauggaaca uucaacgcug ucggugaguu ugggauucaa aaacaaaaaa accaccgacc   60
guugacugua ccuugg                                                  76

<210> SEQ ID NO 379
<211> LENGTH: 75
<212> TYPE: RNA
<213> ORGANISM: Homo sapiens and Mus musculus
<220> FEATURE:
<221> NAME/KEY: misc_RNA
<222> LOCATION: (1)..(75)
<223> OTHER INFORMATION: predicted precursor structure: mir-C2, 5' to 3'
      sequence

<400> SEQUENCE: 379
accauuuuug gcaauggag aacucacacc gguaagguaa ugggacccgg ugguucuaga    60
cuugccaacu auggu                                                   75

<210> SEQ ID NO 380
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precursor structure: mir-C3, 5' to 3'
      sequence

<400> SEQUENCE: 380
cuguguaugg cacgguaga auucacugug aacagucuca gucagugaau uaccgaaggg   60
ccauaaacag                                                         70

<210> SEQ ID NO 381
<211> LENGTH: 73
<212> TYPE: RNA
<213> ORGANISM: Homo sapiens and Mus musculus
<220> FEATURE:
<221> NAME/KEY: misc_RNA
<222> LOCATION: (1)..(73)
<223> OTHER INFORMATION: predicted precursor structure: mir-C4, 5' to 3'
      sequence

<400> SEQUENCE: 381
uggaucuuuu ugcggucugg gcuugcuguu uucucgacag uagucaggaa gcccuuaccc   60
```

-continued caaaaaguau cua                                                73

<210> SEQ ID NO 382
<211> LENGTH: 69
<212> TYPE: RNA
<213> ORGANISM: Homo sapiens and Mus musculus
<220> FEATURE:
<221> NAME/KEY: misc_RNA
<222> LOCATION: (1)..(69)
<223> OTHER INFORMATION: predicted precursor structure: mir-C5, 5' to 3'
      sequence

<400> SEQUENCE: 382 ccuuccuua ucacuuuucc agccagcuuu gugacucuaa guguuggacg gagaacugau    60
aaggguagg                                                          69

<210> SEQ ID NO 383
<211> LENGTH: 65
<212> TYPE: RNA
<213> ORGANISM: Homo sapiens and Mus musculus
<220> FEATURE:
<221> NAME/KEY: misc_RNA
<222> LOCATION: (1)..(65)
<223> OTHER INFORMATION: predicted precursor structure: mir-C6, 5' to 3'
      sequence

<400> SEQUENCE: 383
agggauugga gagaaaggca guccugaug gucccuccc aggggcuggc uuccucugg      60 uccuu                                                              65

<210> SEQ ID NO 384
<211> LENGTH: 71
<212> TYPE: RNA
<213> ORGANISM: Homo sapiens and Mus musculus
<220> FEATURE:
<221> NAME/KEY: misc_RNA
<222> LOCATION: (1)..(71)
<223> OTHER INFORMATION: predicted precursor structure: mir-C7, 5' to 3'
      sequence

<400> SEQUENCE: 384 acuuccaaa gaaucuccu uugggcuuu cucauuuuau uuuaagcccu aaggugaauu      60
uuuugggaag u                                                       71

<210> SEQ ID NO 385
<211> LENGTH: 61
<212> TYPE: RNA
<213> ORGANISM: Homo sapiens and Mus musculus
<220> FEATURE:
<221> NAME/KEY: misc_RNA
<222> LOCATION: (1)..(61)
<223> OTHER INFORMATION: predicted precursor structure: mir-C8, 5' to 3'
      sequence

<400> SEQUENCE: 385
ucaggcuaca acacaggacc cgggcgcugc ucugaccccu cgugucuugu guugcagccg  60
g                                                                 61

<210> SEQ ID NO 386
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)

```
<223> OTHER INFORMATION: predicted precursor structure: mir-C9, 5' to 3'
      sequence

<400> SEQUENCE: 386
gccguggcca ucuuacuggg cagcauugga uagugucuga ucucuaauac ugccugguaa    60
ugaugacggc                                                          70

<210> SEQ ID NO 387
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-C10, 5' to
      3' sequence

<400> SEQUENCE: 387
ucucacaucc cuugcauggu ggagggugag cucucugaaa accccuccca caugcagggu    60
uugcagga                                                            68

<210> SEQ ID NO 388
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-C11, 5' to
      3' sequence

<400> SEQUENCE: 388
cuccggugcc uacugagcug auaucaguuc ucauuucaca cacuggcuca guucagcagg    60
aacaggag                                                            68

<210> SEQ ID NO 389
<211> LENGTH: 67
<212> TYPE: RNA
<213> ORGANISM: Homo sapiens and Mus musculus
<220> FEATURE:
<221> NAME/KEY: misc_RNA
<222> LOCATION: (1)..(67)
<223> OTHER INFORMATION: predicted precursor structure: mir-C12, 5' to
      3' sequence

<400> SEQUENCE: 389
cugugugaua uguuugauau auuagguugu uauuuaaucc aacuauauau caagcauauu    60
ccuacag                                                             67

<210> SEQ ID NO 390
<211> LENGTH: 74
<212> TYPE: RNA
<213> ORGANISM: Homo sapiens and Mus musculus
<220> FEATURE:
<221> NAME/KEY: misc_RNA
<222> LOCATION: (1)..(74)
<223> OTHER INFORMATION: predicted precursor structure: mir-C13, 5' to
      3' sequence

<400> SEQUENCE: 390
agcgggcaac ggaaucccaa aagcagcugu ugucuccaga gcauuccagc ugcacuugga    60
uuucguuccc ugcu                                                     74

<210> SEQ ID NO 391
```

```
<211> LENGTH: 62
<212> TYPE: RNA
<213> ORGANISM: Homo sapiens and Mus musculus
<220> FEATURE:
<221> NAME/KEY: misc_RNA
<222> LOCATION: (1)..(62)
<223> OTHER INFORMATION: predicted precursor structure: mir-c14, 5' to
      3' sequence

<400> SEQUENCE: 391
cugaccuaug aauugacagc cagugcucuc gucucccuc uggcugccaa uuccauaggu    60
ca                                                                  62

<210> SEQ ID NO 392
<211> LENGTH: 72
<212> TYPE: RNA
<213> ORGANISM: Homo sapiens and Mus musculus
<220> FEATURE:
<221> NAME/KEY: misc_RNA
<222> LOCATION: (1)..(72)
<223> OTHER INFORMATION: predicted precursor structure: mir-c15, 5' to
      3' sequence

<400> SEQUENCE: 392
uccugccggu gguuuuaccc uaugguaggu uacgucaugc uguucuacca caggguagaa    60
ccacggacag ga                                                       72

<210> SEQ ID NO 393
<211> LENGTH: 66
<212> TYPE: RNA
<213> ORGANISM: Homo sapiens and Mus musculus
<220> FEATURE:
<221> NAME/KEY: misc_RNA
<222> LOCATION: (1)..(66)
<223> OTHER INFORMATION: predicted precursor structure: mir-c16, 5' to
      3' sequence

<400> SEQUENCE: 393
gagagcuggg ucuuugcggg caagaugaga gugucaguuc aacuggccua caaaguccca    60
guccuc                                                              66

<210> SEQ ID NO 394
<211> LENGTH: 67
<212> TYPE: RNA
<213> ORGANISM: Homo sapiens and Mus musculus
<220> FEATURE:
<221> NAME/KEY: misc_RNA
<222> LOCATION: (1)..(67)
<223> OTHER INFORMATION: predicted precursor structure: mir-c17, 5' to
      3' sequence

<400> SEQUENCE: 394
aucgggugua acagcaacuc cauguggacu gugcucggau uccaguggag cugcuguuac    60
uucugau                                                             67

<210> SEQ ID NO 395
<211> LENGTH: 58
<212> TYPE: RNA
<213> ORGANISM: Homo sapiens and Mus musculus
<220> FEATURE:
<221> NAME/KEY: misc_RNA
<222> LOCATION: (1)..(58)
<223> OTHER INFORMATION: predicted precursor structure: mir-c18, 5' to
      3' sequence

<400> SEQUENCE: 395
```

```
uagcagcaca gaaauauugg caugggggaag ugagucugcc aauauuggcu gugcugcu        58
```

<210> SEQ ID NO 396
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precursor structure: mic-c19, 5' to
      3' sequence

<400> SEQUENCE: 396

```
gugaauuagg uaguuucaug uuguugggcc uggguuucug aacacaacaa cauuaaacca        60
cccgauucac                                                              70
```

<210> SEQ ID NO 397
<211> LENGTH: 75
<212> TYPE: RNA
<213> ORGANISM: Homo sapiens and Mus musculus
<220> FEATURE:
<221> NAME/KEY: misc_RNA
<222> LOCATION: (1)..(75)
<223> OTHER INFORMATION: predicted precursor structure: mir-c20, 5' to
      3' sequence

<400> SEQUENCE: 397

```
ggcugugccg gguagagagg gcagugggag guaagagcuc uucacccuuc accaccuucu        60
ccacccagca uggcc                                                        75
```

<210> SEQ ID NO 398
<211> LENGTH: 62
<212> TYPE: RNA
<213> ORGANISM: Homo sapiens and Mus musculus
<220> FEATURE:
<221> NAME/KEY: misc_RNA
<222> LOCATION: (1)..(62)
<223> OTHER INFORMATION: predicted precursor structure: mir-c21, 5' to
      3' sequence

<400> SEQUENCE: 398

```
ucauuggucc agaggggaga uagguuccug ugauuuuucc uucuucucua agaauaaau         60 ga                                                                      62
```

<210> SEQ ID NO 399
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precursor structure: mir-c22, 5' to
      3' sequence

<400> SEQUENCE: 399

```
gccaucccag uguucagacu accuguucag gaggcuggga cauguacagu agucugcaca        60
uugguuaggc                                                              70
```

<210> SEQ ID NO 400
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precusor structure: mir-c23, 5' to 3'

-continued sequence

<400> SEQUENCE: 400
gccguggcca ucuuacuggg cagcauugga uagugucuga ucucuaauac ugccugguaa    60
ugaugacggc                                                          70

<210> SEQ ID NO 401
<211> LENGTH: 66
<212> TYPE: RNA
<213> ORGANISM: Homo sapiens and Mus musculus
<220> FEATURE:
<221> NAME/KEY: misc_RNA
<222> LOCATION: (1)..(66)
<223> OTHER INFORMATION: predicted precursor structure: mir-c24, 5' to
      3' sequence

<400> SEQUENCE: 401
uaccuuacuc aguaaggcau uguucuucua uauuaauaaa ugaacagugc cuucugugu     60 agggua                                                              66

<210> SEQ ID NO 402
<211> LENGTH: 72
<212> TYPE: RNA
<213> ORGANISM: Homo sapiens and Mus musculus
<220> FEATURE:
<221> NAME/KEY: misc_RNA
<222> LOCATION: (1)..(72)
<223> OTHER INFORMATION: predicted precursor structure: mir-c25, 5' to
      3' sequence

<400> SEQUENCE: 402
guuccuuuuu ccaugcaua uacuucuuug uggaucuggu cuaaagaggu auagcgcaug     60
ggaagaugga gc                                                       72

<210> SEQ ID NO 403
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-c26, 5' to
      3' sequence

<400> SEQUENCE: 403
cggucagugg uuucuggaca auucaccagu uuugacagaa uucgugaaug uuaagguacc    60
acugacca                                                            68

<210> SEQ ID NO 404
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-c27, 5' to
      3' sequence

<400> SEQUENCE: 404
uggacuuccc uuugucaucc uaugccugag aauauaugaa ggaggcuggg aaggcaaagg    60
gacguuca                                                            68

<210> SEQ ID NO 405
<211> LENGTH: 68

```
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-c28, 5' to
      3' sequence

<400> SEQUENCE: 405
cucuuguccu ucauuccacc ggagucuguc uuaugccaac cagauuucag uggagugaag      60
cucaggag                                                              68

<210> SEQ ID NO 406
<211> LENGTH: 76
<212> TYPE: RNA
<213> ORGANISM: Homo sapiens and Mus musculus
<220> FEATURE:
<221> NAME/KEY: misc_RNA
<222> LOCATION: (1)..(76)
<223> OTHER INFORMATION: predicted precursor structure: mir-c29, 5' to
      3' sequence

<400> SEQUENCE: 406
gccuggucca gugguucuug acaguucaac aguucuguag cacaauugug aaauguuuag      60
gaccacuaga cccggc                                                     76

<210> SEQ ID NO 407
<211> LENGTH: 73
<212> TYPE: RNA
<213> ORGANISM: Homo sapiens and Mus musculus
<220> FEATURE:
<221> NAME/KEY: misc_RNA
<222> LOCATION: (1)..(73)
<223> OTHER INFORMATION: predicted precursor structure: mir-c30, 5' to
      3' sequence

<400> SEQUENCE: 407
ccaggccaca ugcuucuuua uauccucaua gauaucucag cacuauggaa uguaaggaag      60 uguguggut ugg                                                         73

<210> SEQ ID NO 408
<211> LENGTH: 70
<212> TYPE: RNA
<213> ORGANISM: Homo sapiens and Mus musculus
<220> FEATURE:
<221> NAME/KEY: misc_RNA
<222> LOCATION: (1)..(70)
<223> OTHER INFORMATION: predicted precursor structure: mir-C31, 5' to
      3' sequence

<400> SEQUENCE: 408
gccaucccag uguucagacu accuguucag gaggcuggga cauguacagu agucugcaca      60
uugguuaggc                                                            70

<210> SEQ ID NO 409
<211> LENGTH: 68
<212> TYPE: RNA
<213> ORGANISM: Homo sapiens and Mus musculus
<220> FEATURE:
<221> NAME/KEY: misc_RNA
<222> LOCATION: (1)..(68)
<223> OTHER INFORMATION: predicted precursor structure: mir-c32, 5' to
      3' sequence

<400> SEQUENCE: 409
uauauacccu guagaaccga auuugugugg uacccacaua gucacagauu cgauucuagg      60
``` ggaauaua                                                          68

<210> SEQ ID NO 410
<211> LENGTH: 80
<212> TYPE: RNA
<213> ORGANISM: Homo sapiens and Mus musculus
<220> FEATURE:
<221> NAME/KEY: misc_RNA
<222> LOCATION: (1)..(80)
<223> OTHER INFORMATION: predicted precursor structure: mir-c33, 5' to
      3' sequence

<400> SEQUENCE: 410
ccuguugcca caaacccgua gauccgaacu uguggauua guccgcacaa gcuuguaucu      60
auagguaugu gucuguuagg                                                 80

<210> SEQ ID NO 411
<211> LENGTH: 79
<212> TYPE: RNA
<213> ORGANISM: Homo sapiens and Mus musculus
<220> FEATURE:
<221> NAME/KEY: misc_RNA
<222> LOCATION: (1)..(79)
<223> OTHER INFORMATION: predicted precursor structure: mir-c34, 5' to
      3' sequence

<400> SEQUENCE: 411
aaggcagggg ugagggguug cgggaggagc cgggcggagg cugcggcuug cgcuucuccu     60
ggcucuccuc ccucuccuu                                                 79

<210> SEQ ID NO 412
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 412
cagccacacg gcaccgaatt cctcactaaa                                     30

<210> SEQ ID NO 413
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 413
gactagcttg gtgccgaatt cgcggttaaa                                     30

<210> SEQ ID NO 414
<211> LENGTH: 21
<212> TYPE: RNA
<213> ORGANISM: Caenorhabditis elegans

<400> SEQUENCE: 414
ucccugagac cucaagugug a                                              21

<210> SEQ ID NO 415
<211> LENGTH: 22
<212> TYPE: RNA
<213> ORGANISM: Drosophila melanogaster

<400> SEQUENCE: 415

```
ucccugagac ccuaacuugu ga                                              22

<210> SEQ ID NO 416
<211> LENGTH: 22
<212> TYPE: RNA
<213> ORGANISM: Homo sapiens and Mus musculus

<400> SEQUENCE: 416
ucccugagac ccuaacuugu ga                                              22

<210> SEQ ID NO 417
<211> LENGTH: 24
<212> TYPE: RNA
<213> ORGANISM: Homo sapiens and Mus musculus

<400> SEQUENCE: 417
ucccugagac ccuuuaaccu guga                                            24

<210> SEQ ID NO 418
<211> LENGTH: 22
<212> TYPE: RNA
<213> ORGANISM: Mus musculus

<400> SEQUENCE: 418
auaagacgag caaaaagcuu gu                                              22
```

IDENTIFICATION OF NOVEL GENES CODING FOR SMALL TEMPORAL RNAS

This application is a divisional of U.S. Ser. No. 12/775,947 filed May 7, 2010; which is a divisional of Ser. No. 11/747,409 filed May 11, 2007, now U.S. Pat. No. 7,723,510, issued May 25, 2010; which is a divisional of Ser. No. 10/490,955 filed Sep. 15, 2009, now U.S. Pat. No. 7,232,806 issued Jun. 19, 2007, which is a 35 U.S.C. 371 National Phase Entry Application from PCT/EP2002/10881, filed Sep. 27, 2002, which claims the benefit of European Patent Application Nos. 01123453.1 filed on Sep. 28, 2001, 02006712.0 filed on Mar. 22, 2002 and 02016772.2 filed Jul. 26, 2002, the disclosure of which are incorporated herein in their entirety by reference.

The present invention relates to novel small expressed (micro)RNA molecules associated with physiological regulatory mechanisms, particularly in developmental control.

In *Caenorhabditis elegans*, lin-4 and let-7 encode 22- and 21-nucleotide RNAs, respectively (1, 2), that function as key regulators of developmental timing (3-5). Because the appearance of these short RNAs is regulated during development, they are also referred to as "microRNAs" (miRNAs) or small temporal RNAs (stRNAs) (6). lin-4 and let-21 are the only known miRNAs to date.

Two distinct pathways exist in animals and plants in which 21- to 23-nucleotide RNAs function as post-transcriptional regulators of gene expression. Small interfering RNAs (siRNAs) act as mediators of sequence-specific mRNA degradation in RNA interference (RNAi) (7-11) whereas miRNAs regulate developmental timing by mediating sequence-specific repression of mRNA translation (3-5). siRNAs and miRNAs are excised from double-stranded RNA (dsRNA) precursors by Dicer (12, 13, 29), a multidomain RNase III protein, thus producing RNA species of similar size. However, siRNAs are believed to be double-stranded (8, 11, 12), while miRNAs are single-stranded (6).

We show that many more short, particularly 21- and 22-nt expressed RNAs, termed microRNAs (miRNAs), exist in invertebrates and vertebrates, and that some of these novel RNAs, similar to let-7 RNA (6), are also highly conserved. This suggests that sequence-specific post-transcriptional regulatory mechanisms mediated by small RNAs are more general than previously appreciated.

The present invention relates to an isolated nucleic acid molecule comprising:
(a) a nucleotide sequence as shown in Table 1, Table 2, Table 3 or Table 4
(b) a nucleotide sequence which is the complement of (a),
(c) a nucleotide sequence which has an identity of at least 80%, preferably of at least 90% and more preferably of at least 99%, to a sequence of (a) or (b) and/or
(d) a nucleotide sequence which hybridizes under stringent conditions to a sequence of (a), (b) end/or (c).

In a preferred embodiment the invention relates to miRNA molecules and analogs thereof, to miRNA precursor molecules and to DNA molecules encoding miRNA or miRNA precursor molecules.

Preferably the identity of sequence (c) to a sequence of (a) or (b) is at least 90%, more preferably at least 95%. The determination of identity (percent) may be carried out as follows:

$$I = n : L$$

wherein I is the identity in percent, n is the number of identical nucleotides between a given sequence and a comparative sequence as shown in Table 1, Table 2, Table 3 or Table 4 and L is the length of the comparative sequence. It should be noted that the nucleotides A, C, G and U as depicted in Tables 1, 2, 3 and 4 may denote ribonucleotides, deoxyribonucleotides and/or other nucleotide analogs, e.g. synthetic non-naturally occurring nucleotide analogs. Further nucleobases may be substituted by corresponding nucleobases capable of forming analogous H-bonds to a complementary nucleic acid sequence, e.g. U may be substituted by T.

Further, the invention encompasses nucleotide sequences which hybridize under stringent conditions with the nucleotide sequence as shown in Table 1. Table 2, Table 3 or Table 4, a complementary sequence thereof or a highly identical sequence. Stringent hybridization conditions comprise washing for 1 h in 1×SSC and 0.1% SDS at 45° C., preferably at 48° C. and more preferably at 50° C., particularly for 1 h in 0.2×SSC and 0.1% SDS.

The isolated nucleic acid molecules of the invention preferably have a length of from 18 to 100 nucleotides, and more preferably from 18 to 80 nucleotides. It should be noted that mature miRNAs usually have a length of 19-24 nucleotides, particularly 21, 22 or 23 nucleotides. The miRNAs, however, may be also provided as a precursor which usually has a length of 50-90 nucleotides, particularly 60-80 nucleotides. It should be noted that the precursor may be produced by processing of a primary transcript which may have a length of >100 nucleotides.

The nucleic acid molecules may be present in single-stranded or double-stranded form. The miRNA as such is usually a single-stranded molecule, while the mi-precursor is usually an at least partially self-complementary molecule capable of forming double-stranded portions, e.g. stem- and loop-structures. DNA molecules encoding the miRNA and miRNA precursor molecules. The nucleic acids may be selected from RNA, DNA or nucleic acid analog molecules, such as sugar- or backbone-modified ribonucleotides or deoxyribonucleotides. It should be noted, however, that other nucleic analogs, such as peptide nucleic acids (PNA) or locked nucleic acids (LNA), are also suitable.

In an embodiment of the invention the nucleic acid molecule is an RNA- or DNA molecule, which contains at least one modified nucleotide analog, i.e. a naturally occurring ribonucleotide or deoxyribonucleotide is substituted by a non-naturally occurring nucleotide. The modified nucleotide analog may be located for example at the 5'-end and/or the 3'-end of the nucleic acid molecule.

Preferred nucleotide analogs are selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. In preferred sugar-modified ribonucleotides the 2'-OH-group is replaced by a group selected from H, OR, R, halo, SH, SR, $NH_2$, NHR, $NR_2$ or CN, wherein R is $C_1$-$C_8$ alkyl, alkenyl or alkynyl and halo is F, Cl, Br or I. In preferred backbone-modified ribonucleotides the phosphoester group connecting to adjacent ribonucleotides is replaced by a modified group, e.g. of phosphothioate group. It should be noted that the above modifications may be combined.

The nucleic acid molecules of the invention may be obtained by chemical synthesis methods or by recombinant methods, e.g. by enzymatic transcription from synthetic DNA-templates or from DNA-plasmids isolated from recombinant organisms. Typically phage RNA-polymerases are used for transcription, such as T7, T3 or SP6 RNA-polymerases.

The invention also relates to a recombinant expression vector comprising a recombinant nucleic acid operatively linked to an expression control sequence, wherein expression, i.e. transcription and optionally further processing results in a miRNA-molecule or miRNA precursor molecule as described above. The vector is preferably a DNA-vector, e.g. a viral vector or a plasmid, particularly an expression vector suitable for nucleic acid expression in eukaryotic, more particularly mammalian cells. The recombinant nucleic acid contained in said vector may be a sequence which results in the transcription of the miRNA-molecule as such, a precursor or a primary transcript thereof, which may be further processed to give the miRNA-molecule.

Further, the invention relates to diagnostic or therapeutic applications of the claimed nucleic acid molecules. For example, miRNAs may be detected in biological samples, e.g. in tissue sections, in order to determine and classify certain cell types or tissue types or miRNA-associated pathogenic disorders which are characterized by differential expression of miRNA-molecules or miRNA-molecule patterns. Further, the developmental stage of cells may be classified by determining temporarily expressed miRNA-molecules.

Further, the claimed nucleic acid molecules are suitable for therapeutic applications. For example, the nucleic acid molecules may be used as modulators or targets of developmental processes or disorders associated with developmental dysfunctions, such as cancer. For example, miR-15 and miR-16 probably function as tumor-suppressors and thus expression or delivery of these RNAs or analogs or precursors thereof to tumor cells may provide therapeutic efficacy, particularly against leukemias, such as B-cell chronic lymphocytic leukemia (B-CLL). Further, miR-10 is a possible regulator of the translation of Hox Genes, particularly Hox 3 and Hox 4 (or Scr and Dfd in *Drosophila*).

In general, the claimed nucleic acid molecules may be used as a modulator of the expression of genes which are at least partially complementary to said nucleic acid. Further, miRNA molecules may act as target for therapeutic screening procedures, e.g. inhibition or activation of miRNA molecules might modulate a cellular differentiation process, e.g. apoptosis.

Furthermore, existing miRNA molecules may be used as starting materials for the manufacture of sequence-modified miRNA molecules, in order to modify the target-specificity thereof, e.g. an oncogene, a multidrug-resistance gene or another therapeutic target gene. The novel engineered miRNA molecules preferably have an identity of at least 80% to the starting miRNA, e.g. as depicted in Tables 1, 2, 3 and 4. Further, miRNA molecules can be modified, in order that they are symmetrically processed and then generated as double-stranded siRNAs which are again directed against therapeutically relevant targets.

Furthermore, miRNA molecules may be used for tissue reprogramming procedures, e.g. a differentiated cell line might be transformed by expression of miRNA molecules into a different cell type or a stem cell.

For diagnostic or therapeutic applications, the claimed RNA molecules are preferably provided as a pharmaceutical composition. This pharmaceutical composition comprises as an active agent at least one nucleic acid molecule as described above and optionally a pharmaceutically acceptable carrier.

The administration of the pharmaceutical composition may be carried out by known methods, wherein a nucleic acid is introduced into a desired target cell in vitro or in vivo.

Commonly used gene transfer techniques include calcium phosphate, DEAE-dextran, electroporation and microinjection and viral methods [30, 31, 32, 33, 34]. A recent addition to this arsenal of techniques for the introduction of DNA into cells is the use of cationic liposomes [35]. Commercially available cationic lipid formulations are e.g. Tfx 50 (Promega) or Lipofectamin 2000 (Life Technologies).

The composition may be in form of a solution, e.g. an injectable solution, a cream, ointment, tablet, suspension or the like. The composition may be administered in any suitable way, e.g. by injection, by oral, topical, nasal, rectal application etc. The carrier may be any suitable pharmaceutical carrier. Preferably, a carrier is used, which is capable of increasing the efficacy of the RNA molecules to enter the target-cells. Suitable examples of such carriers are liposomes, particularly cationic liposomes.

Further, the invention relates to a method of identifying novel microRNA-molecules and precursors thereof, in eukaryotes, particularly in vertebrates and more particularly in mammals, such as humans or mice. This method comprises: ligating 5'- and 3'-adapter-molecules to the end of a size-fractionated RNA-population, reverse transcribing said adapter-ligated RNA-population, and characterizing said reverse transcribed RNA-molecules, e.g. by amplification, concatamerization, cloning and sequencing.

A method as described above already has been described in (8), however, for the identification of siRNA molecules. Surprisingly, it was found now that the method is also suitable for identifying the miRNA molecules or precursors thereof as claimed in the present application.

Further, it should be noted that as 3'-adaptor for derivatization of the 3'-OH group not only 4-hydroxymethylbenzyl but other types of derivatization groups, such as alkyl, alkyl amino, ethylene glycol or 3'-deoxy groups are suitable.

Further, the invention shall be explained in more detail by the following Figures and Examples:

FIGURE LEGENDS

FIG. 1A. Expression of *D. melanogaster* miRNAs. Northern blots of total RNA isolated from staged populations of *D. melanogaster* were probed for the indicated miRNAs. The position of 76-nt val-tRNA is also indicated on the blots. 5S rRNA serves as loading control. E, embryo; L, larval stage; P, pupae; A, adult; S2, Schneider-2 cells. It should be pointed out, that S2 cells are polyclonal, derived from an unknown subset of embryonic tissues, and may have also lost some features of their tissue of origin while maintained in culture. miR-3 to miR-6 RNAs were not detectable in S2 cells (data not shown). miR-14 was not detected by Northern blotting and may be very weakly expressed, which is consistent with its cloning frequency. Similar miRNA sequences are difficult to distinguish by Northern blotting because of potential cross-hybridization of probes.

FIG. 1B. Expression of vertebrate miRNAs. Northern blots of total RNA isolated from HeLa cells, mouse kidneys, adult zebrafish, frog ovaries, and S2 cells were probed for the indicated miRNAs. The position of 76-nt val-tRNA is also indicated on the blots. 5S rRNA from the preparations of total RNA from the indicated species is also shown. The gels used for probing of miR-18, miR-19a, miR-30, and miR-31 were not run as far as the other gels (see tRNA marker position), miR-32 and miR-33 were not detected by Northern blotting, which is consistent with their low cloning frequency. Oligodeoxynucleotides used as Northern probes were:

let-7a, 5' TACTATACAACCTACTACCTCAATTTGCC; (SEQ ID NO: 1)

let-7d, 5' ACTATGCAACCTACTACCTCT; (SEQ ID NO: 2)

let-7e, 5' ACTATACAACCTCCTACCTCA; (SEQ ID NO: 3)

D. melanogaster val-tRNA, 5' TGGTGTTTCCGCCCGGGAA; (SEQ ID NO: 4)

miR-1, 5' TGGAATGTAAAGAAGTATGGAG; (SEQ ID NO: 5)

miR-2b, 5' GCTCCTCAAAGCTGGCTGTGATA; (SEQ ID NO: 6)

miR-3, 5' TGAGACACACTTTGCCCAGTGA; (SEQ ID NO: 7)

miR-4, 5' TCAATGGTTGTCTAGCTTTAT; (SEQ ID NO: 8)

miR-5, 5' CATATCACAACGATCGTTCCTTT; (SEQ ID NO: 9)

miR-6, 5' AAAAAGAACAGCCACTGTGATA; (SEQ ID NO: 10)

miR-7, 5' TGGAAGACTAGTGATTTTGTTGT; (SEQ ID NO: 11)

miR-8, 5' GACATCTTTACCTGACAGTATTA; (SEQ ID NO: 12)

miR-9, 5' TCATACAGCTAGATAACCAAAGA; (SEQ ID NO: 13)

miR-10, 5' ACAAATTCGGATCTACAGGGT; (SEQ ID NO: 14)

miR-11, 5' GCAAGAACTCAGACTGTGATG; (SEQ ID NO: 15)

miR-12, 5' ACCAGTACCTGATGTAATACTCA; (SEQ ID NO: 16)

miR-13a, 5' ACTCGTCAAAATGGCTGTGATA; (SEQ ID NO: 17)

miR-14; 5' TAGGAGAGAGAAAAAGACTGA; (SEQ ID NO: 18)

miR-15, 5' TAGCAGCACATAATGGTTTGT; (SEQ ID NO: 19)

miR-16, 5' GCCAATATTTACGTGCTGCTA; (SEQ ID NO: 20)

miR-17, 5' TACAAGTGCCTTCACTGCAGTA; (SEQ ID NO: 21)

miR-18, 5' TATCTGCACTAGATGCACCTTA; (SEQ ID NO: 22)

miR-19a, 5' TCAGTTTTGCATAGATTTGCACA; (SEQ ID NO: 23)

miR-20, 5' TACCTGCACTATAAGCACTTTA; (SEQ ID NO: 24)

miR-21, 5' TCAACATCAGTCTGATAAGCTA; (SEQ ID NO: 25)

miR-22, 5' ACAGTTCTTCAACTGGCAGCTT; (SEQ ID NO: 26)

miR-23, 5' GGAAATCCCTGGCAATGTGAT; (SEQ ID NO: 27)

miR-24, 5' CTGTTCCTGCTGAACTGAGCCA; (SEQ ID NO: 28)

miR-25, 5' TCAGACCGAGACAAGTGCAATG; (SEQ ID NO: 29)

miR-26a, 5' AGCCTATCCTGGATTACTTGAA; (SEQ ID NO: 30)

miR-27; 5' AGCGGAACTTAGCCACTGTGAA; (SEQ ID NO: 31)

miR-28, 5' CTCAATAGACTGTGAGCTCCTT; (SEQ ID NO: 32)

miR-29, 5' AACCGATTTCAGATGGTGCTAG; (SEQ ID NO: 33)

miR-30, 5' GCTGCAAACATCCGACTGAAAG; (SEQ ID NO: 34)

miR-31, 5' CAGCTATGCCAGCATCTTGCCT; (SEQ ID NO: 35)

miR-32, 5' GCAACTTAGTAATGTGCAATA; (SEQ ID NO: 36)

miR-33, 5' TGCAATGCAACTACAATGCACC. (SEQ ID NO: 37)

Figure 2:
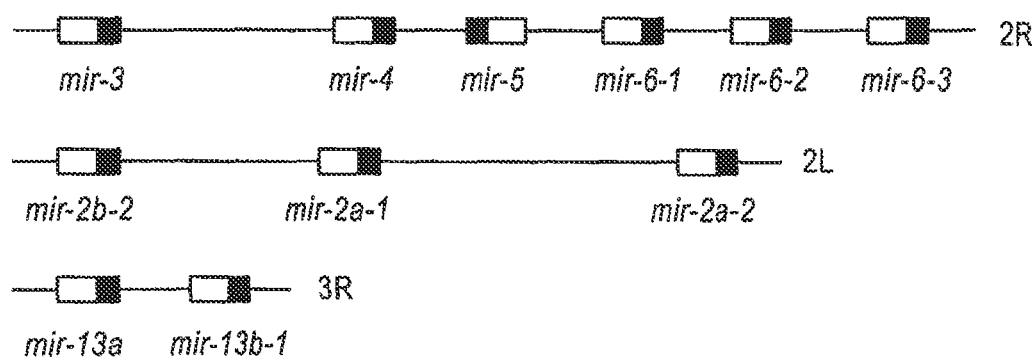
Figure 2:
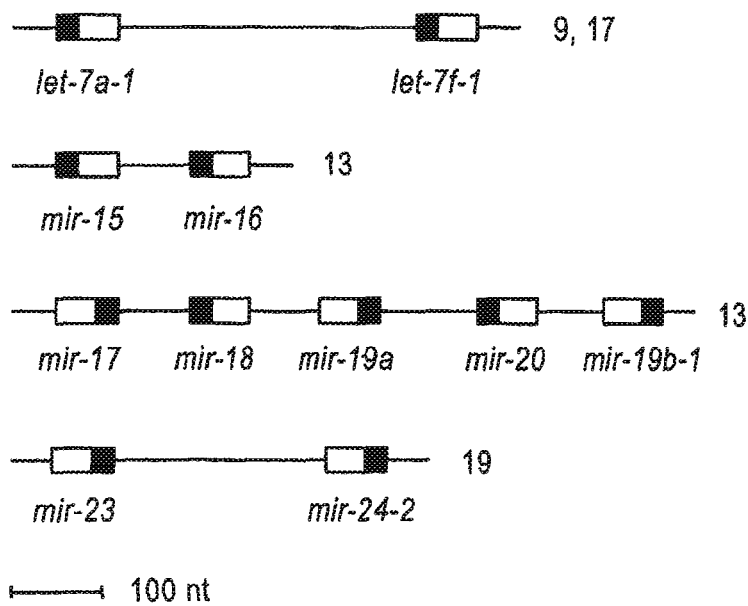

FIG. 2. Genomic organization of miRNA gene clusters. The precursor structure is indicated as box and the location of the miRNA within the precursor is shown in gray; the chromosomal location is also indicated to the right. (A) *D. melanogaster* miRNA gene clusters. (B) Human miRNA gene clusters. The cluster of let-7a-1 and let-7f-1 is separated by 26500 nt from a copy of let-7d on chromosome 9 and 17. A cluster of let-7a-3 and let-7b, separated by 938 nt on chromosome 22, is not illustrated.

Figure 3:
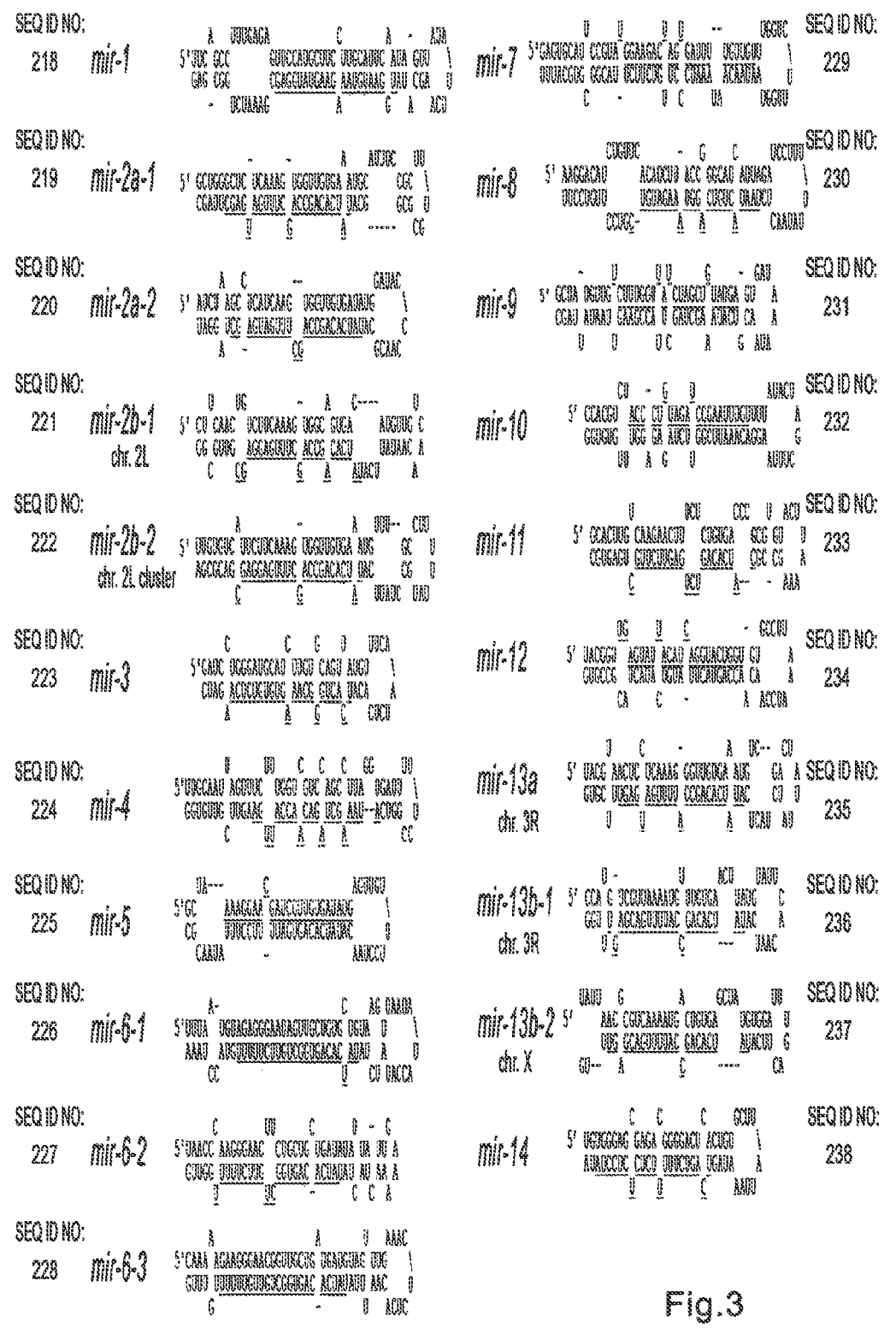

FIG. 3. Predicted precursor structures of *D. melanogaster* miRNAs. RNA secondary structure prediction was performed using mfold version 3.1 [28] and manually refined to accommodate G/U wobble base pairs in the helical segments. The miRNA sequence is underlined. The actual size of the stem-loop structure is not known experimentally and may be slightly shorter or longer than represented. Multicopy miRNAs and their corresponding precursor structures are also shown.

Figure 4:
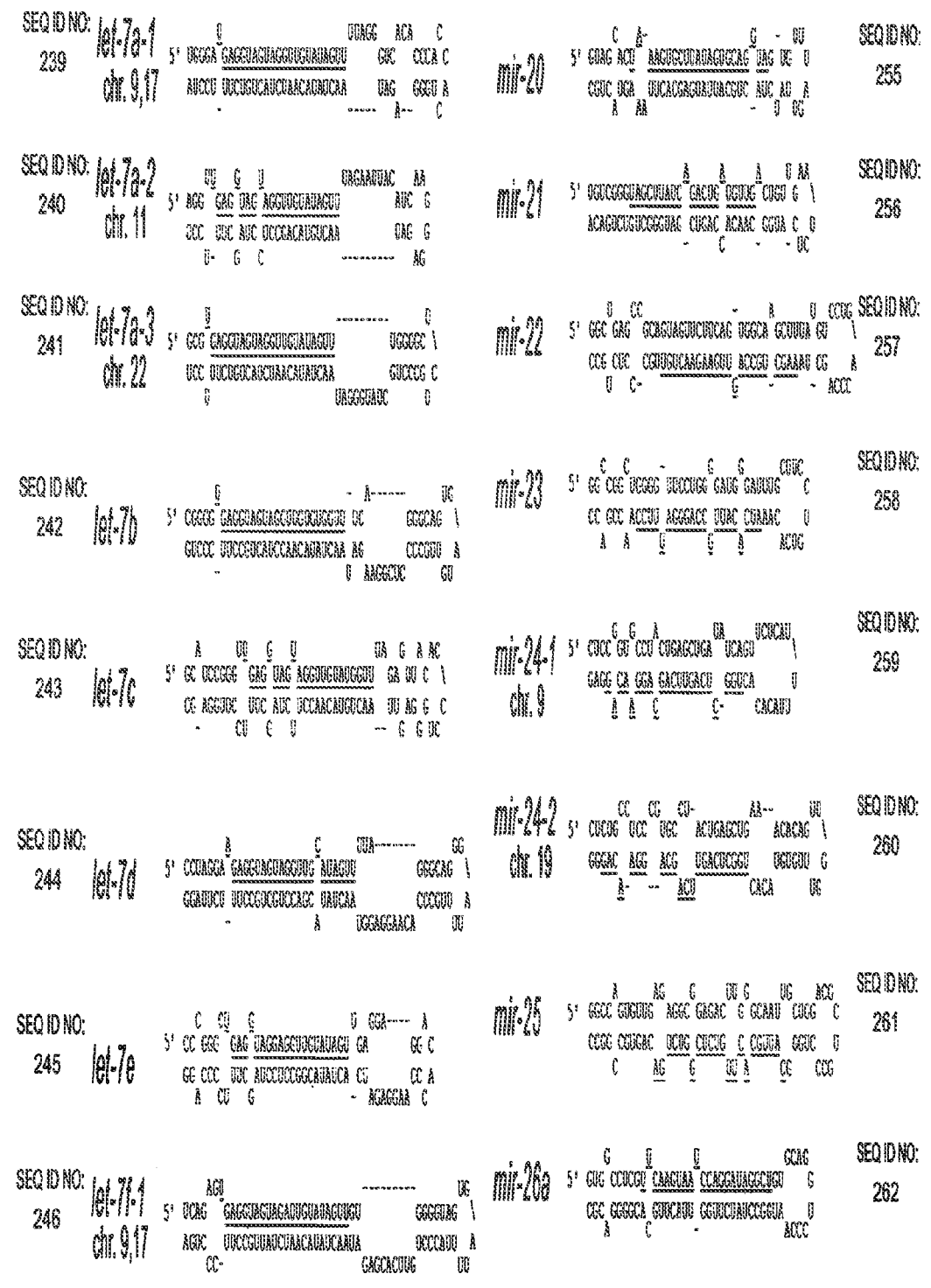
Figure 4:
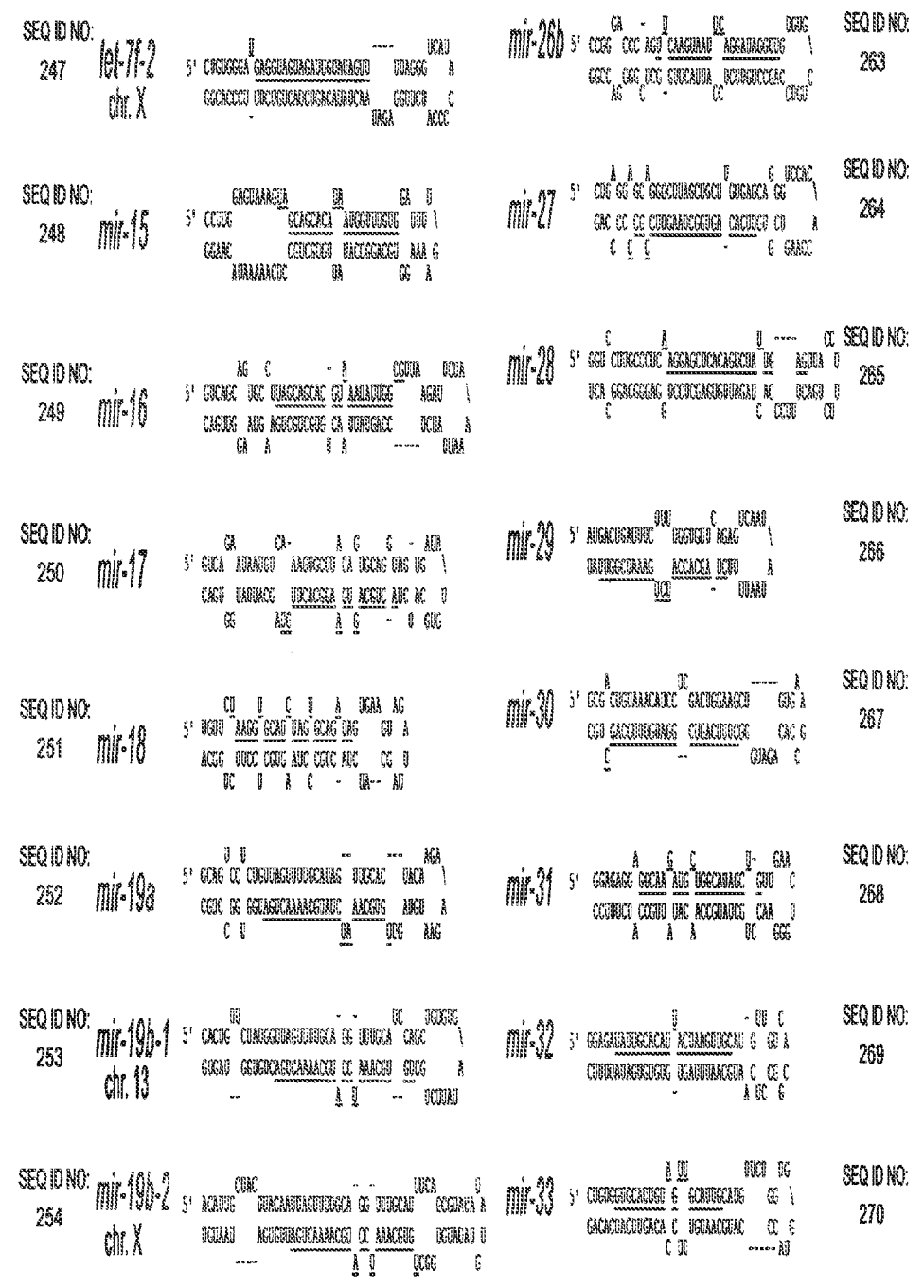

FIG. 4. Predicted precursor structures of human miRNAs. For legend, see FIG. 3.

Figure 5:
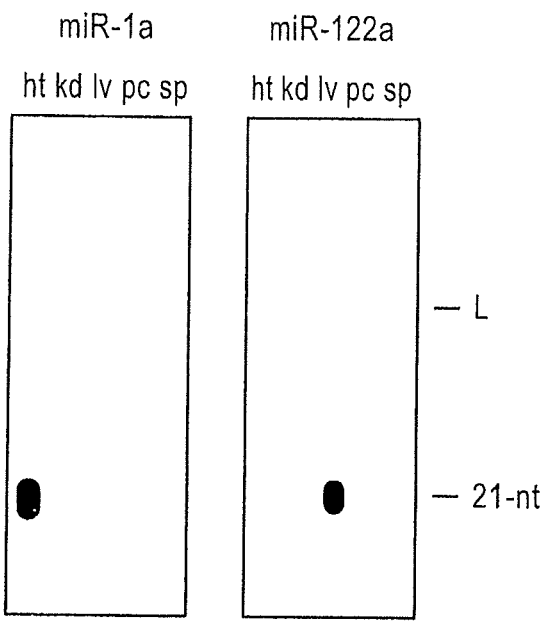
Figure 5:
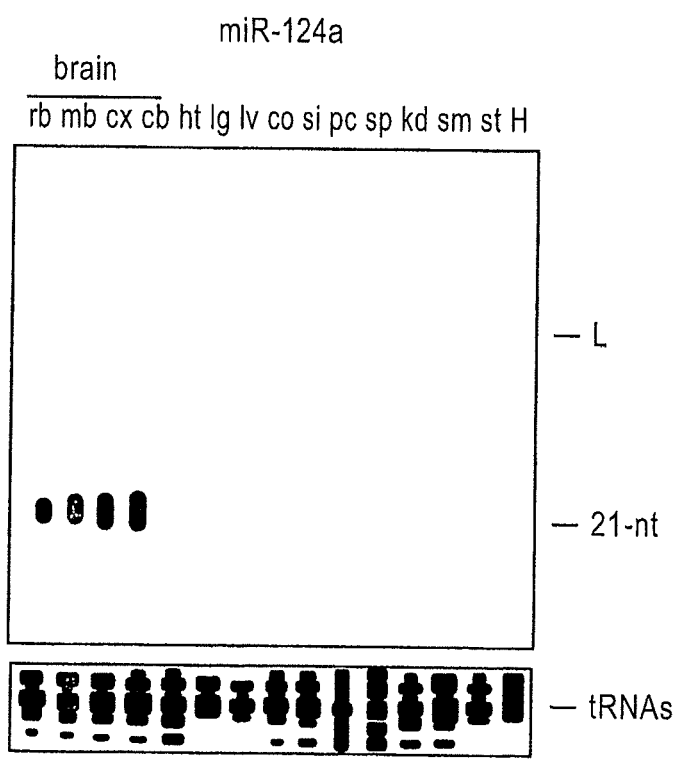
Figure 5:
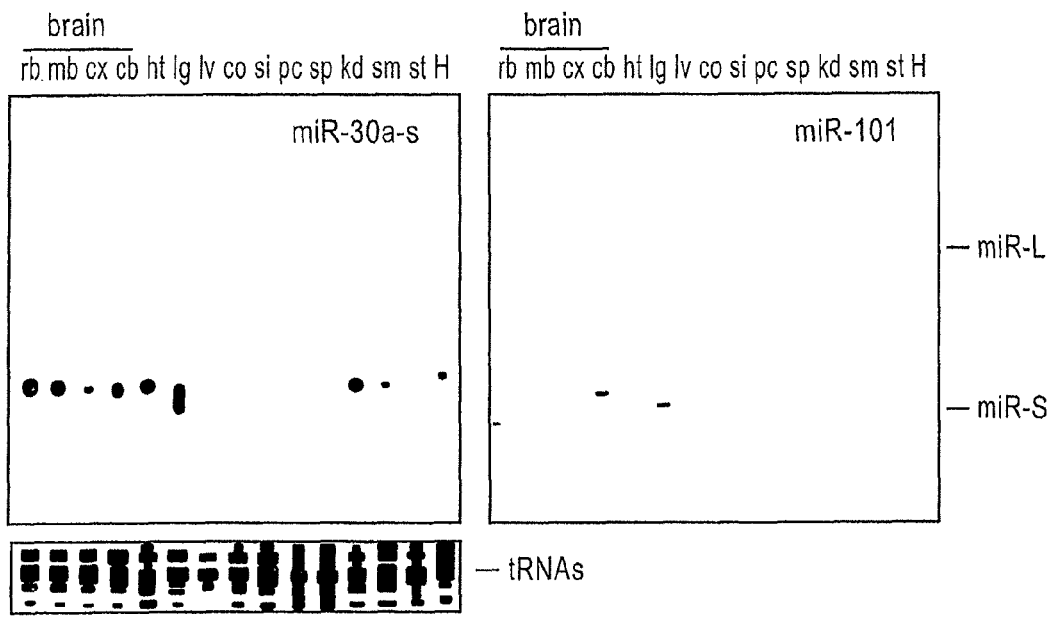
Figure 5:
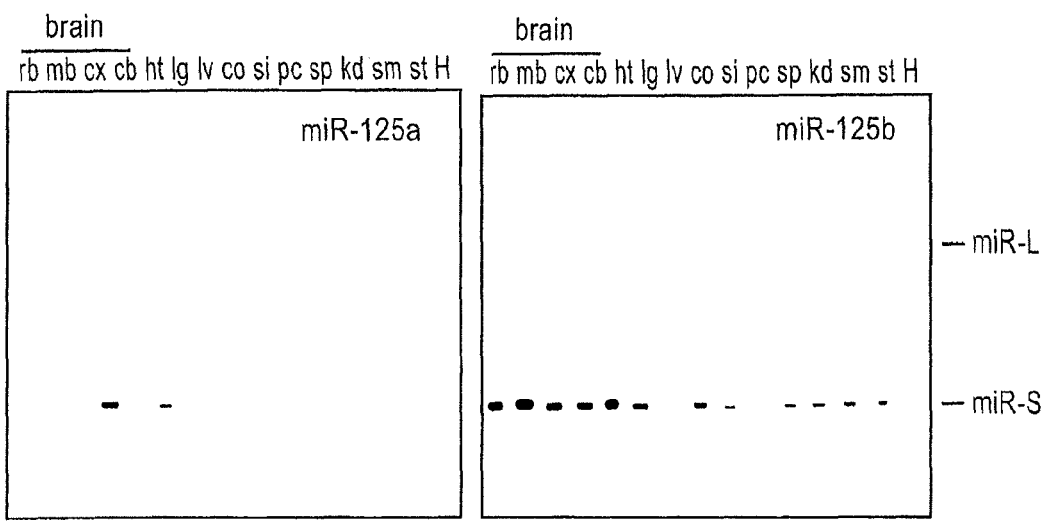
Figure 5:
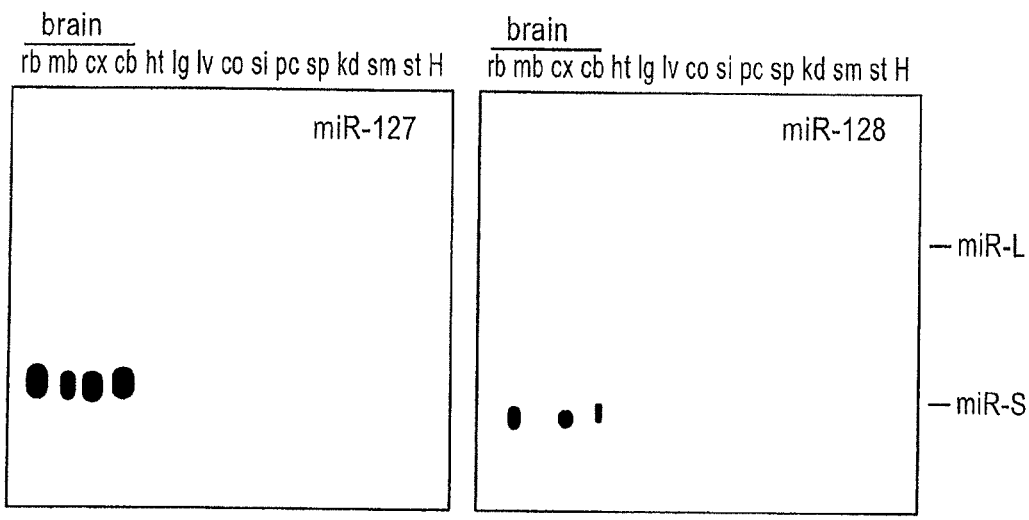
Figure 5:
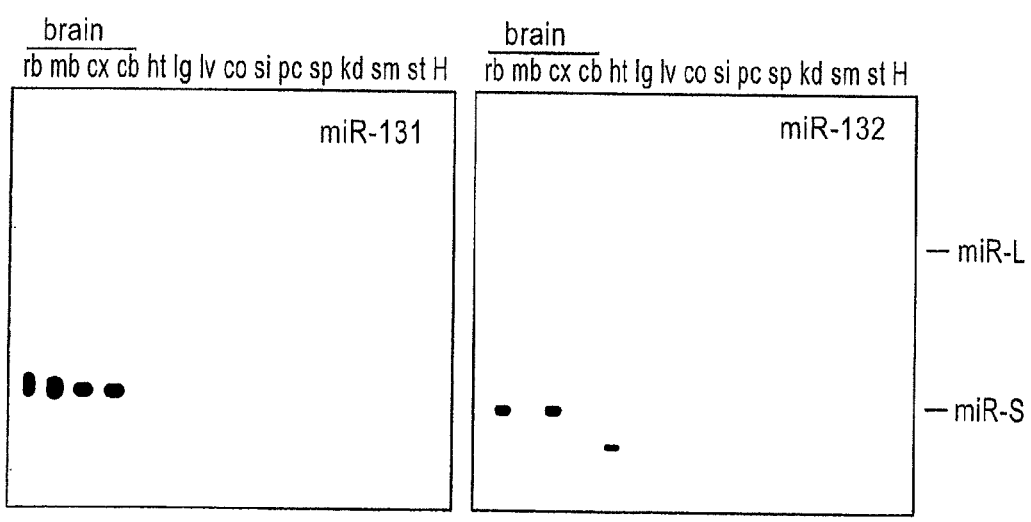
Figure 5:
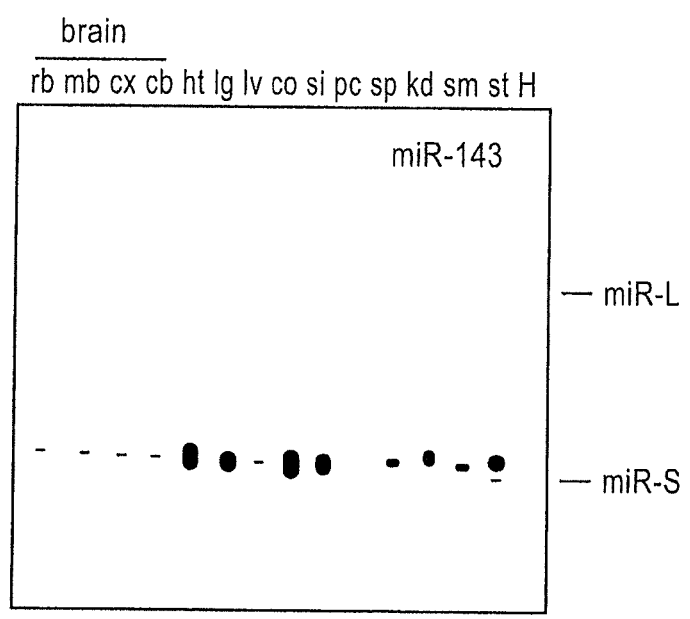

FIG. 5. Expression of novel mouse miRNAs. Northern blot analysis of novel mouse miRNAs. Total RNA from different mouse tissues was blotted and probed with a 5'-radiolabeled oligodeoxynucleotide complementary to the indicated miRNA. Equal loading of total RNA on the gel was verified by ethidium bromide staining prior to transfer; the band representing tRNAs is shown. The fold-back precursors are indicated with capital L. Mouse brains were dissected into midbrain, mb, cortex, cx, cerebellum, cb. The rest of the brain, rb, was also used. Other tissues were heart, ht, lung, lg, liver, lv, colon, co, small intestine, si, pancreas, pc, spleen, sp, kidney, kd, skeletal muscle, sm, stomach, st, H, human Hela SS3 cells. Oligodeoxynucleotides used as Northern probes were:

| | (SEQ ID NO: 38) |
|---|---|
| miR-1a, | CTCCATACTTCTTTACATTCCA; |
| miR-30b, | (SEQ ID NO: 39) GCTGAGTGTAGGATGTTTACA; |
| miR-30a-s, | (SEQ ID NO: 40) GCTTCCAGTCGAGGATGTTTACA; |
| miR-99b, | (SEQ ID NO: 41) CGCAAGGTCGGTTCTACGGGTG; |
| miR-101, | (SEQ ID NO: 42) TCAGTTATCACAGTACTGTA; |
| miR-122a, | (SEQ ID NO: 43) ACAAACACCATTGTCACACTCCA; |
| miR-124a, | (SEQ ID NO: 44) TGGCATTCACCGCGTGCCTTA; |
| MiR-125a, | (SEQ ID NO: 45) CACAGGTTAAAGGGTCTCAGGGA; |
| miR-125b, | (SEQ ID NO: 46) TCACAAGTTAGGGTCTCAGGGA; |
| miR-127, | (SEQ ID NO: 47) AGCCAAGCTCAGACGGATCCGA; |
| miR-128, | (SEQ ID NO: 48) AAAAGAGACCGGTTCACTCTGA; |
| miR-129, | (SEQ ID NO: 49) GCAAGCCCAGACCGAAAAAAG; |
| miR-130, | (SEQ ID NO: 50) GCCCTTTTAACATTGCACTC; |
| miR-131, | (SEQ ID NO: 51) ACTTTCGGTTATCTAGCTTTA; |
| miR-132, | (SEQ ID NO: 52) ACGACCATGGCTGTAGACTGTTA; |
| miR-143, | (SEQ ID NO: 53) TGAGCTACAGTGCTTCATCTCA. |

Figure 6:
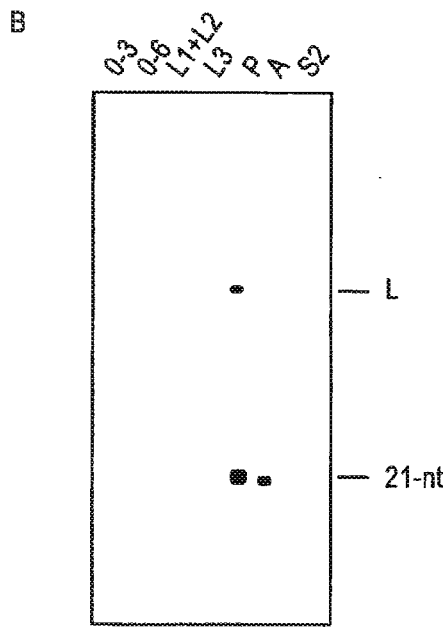

FIG. 6. Potential orthologs of lin-4 stRNA. (A) Sequence alignment of *C. elegans* lin-4 stRNA with mouse miR-125a and miR-125b and the *D. melanogaster* miR-125. Differences are highlighted by gray boxes. (B) Northern blot of total RNA isolated from staged populations of *D. melanogaster*, probed for miR-125. E, embryo; L, larval stage; P, pupae; A, adult; S2, Schneider-2 cells.

Figure 7:
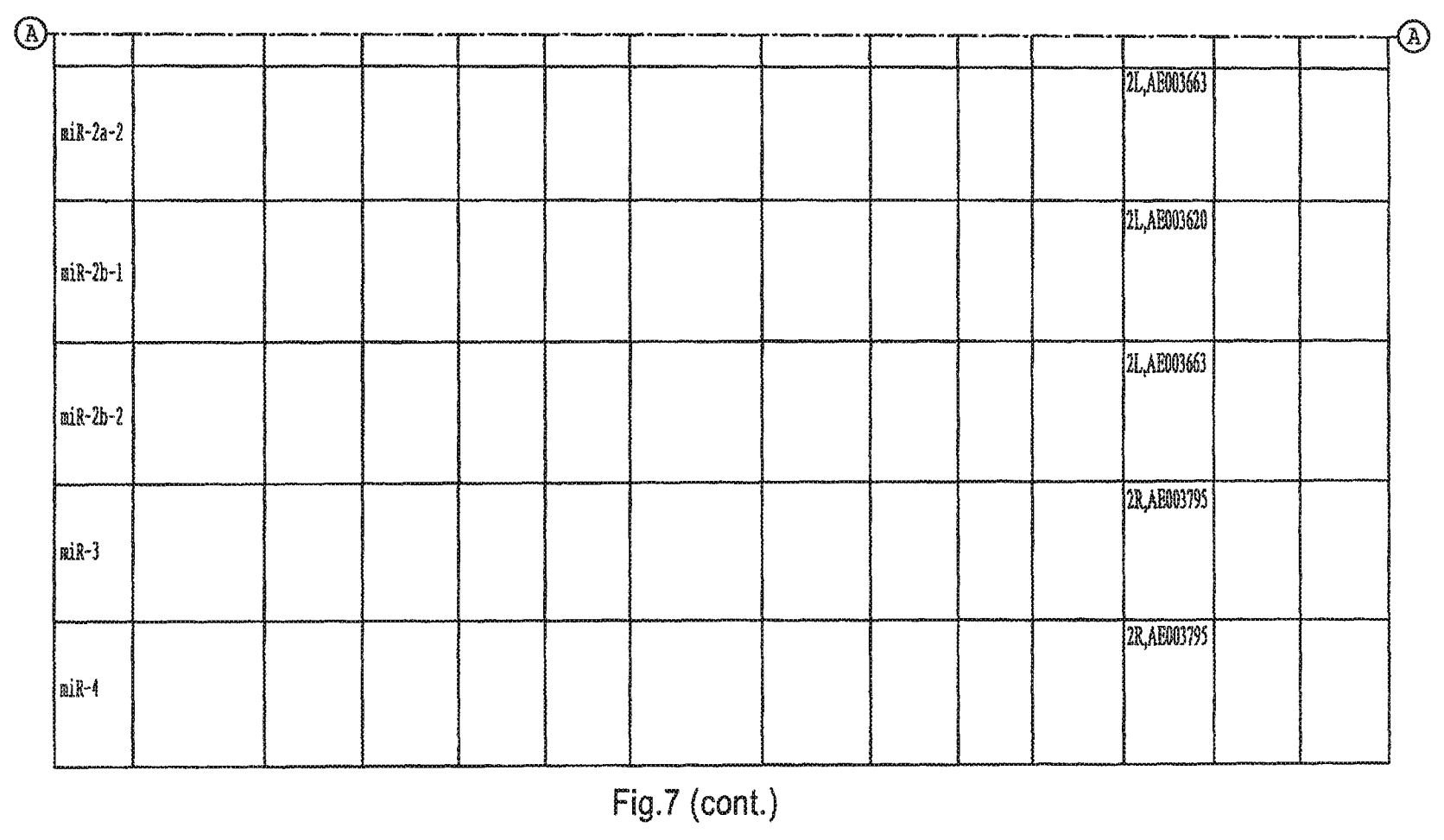

FIG. 7. Predicted precursor structures of miRNAs, sequence accession numbers and homology information. RNA secondary structure prediction was performed using mfold version 3.1 and manually refined to accommodate G/U wobble base pairs in the helical segments. Dashes were inserted into the secondary structure presentation when asymmetrically bulged nucleotides had to be accommodated. The excised miRNA sequence is underlined. The actual size of the stem-loop structure is not known experimentally and may be slightly shorter or longer than represented. Multicopy miRNAs and their corresponding precursor structures are also shown. In cases where no mouse precursors were yet deposited in the database, the human orthologs are indicated. miRNAs which correspond to *D. melanogaster* or human sequences are included. Published *C. elegans* miRNAs [36, 37] are also included in the table. A recent set of new HeLa cell miRNAs is also indicated [46]. If several ESTs were retrieved for one organism in the database, only those with different precursor sequences are listed. miRNA homologs found in other species are indicated. Chromosomal location and sequence accession numbers, and clusters of miRNA genes are indicated. Sequences from cloned miRNAs were searched against mouse and human in GenBank (including trace data), and against *Fugu rubripes* and *Danio rerio* at www.jgi.doe.gov and www.sanger.ac.uk, respectively.

EXAMPLE 1

Micro RNAs from *D. melanogaster* and Human

We previously developed a directional cloning procedure to isolate siRNAs is after processing of long dsRNAs in *Drosophila melanogaster* embryo lysate (8). Briefly, 5' and 3' adapter molecules were ligated to the ends of a size-fractionated RNA population, followed by reverse transcription, PCR amplification, concatamerization, cloning and sequencing. This method, originally intended to isolate siRNAs, led to the simultaneous identification of 14 novel 20- to 23-nt short RNAs which are encoded in the *D. melanogaster* genome and which are expressed in 0 to 2 h embryos (Table 1). The method was adapted to clone RNAs in a similar size range from HeLa cell total RNA (14), which led to the identification of 19 novel human stRNAs (Table 2), thus providing further evidence for the existence of a large class of small RNAs with potential regulatory roles. According to their small size, we refer to these novel RNAs as microRNAs or miRNAs. The miRNAs are abbreviated as miR-1 to miR-33, and the genes encoding miRNAs are named mir-1 to mir-33. Highly homologous miRNAs are classified by adding a lowercase letter, followed by a dash and a number for designating multiple genomic copies of a mir gene.

The expression and size of the cloned, endogenous short RNAs was also examined by Northern blotting (FIG. 1, Table 1 and 2). Total RNA isolation was performed by acid guanidinium thiocyanate-phenol-chloroform extraction [45]. Northern analysis was performed as described [1], except that the total RNA was resolved on a 15% denaturing polyacrylamide gel, transferred onto Hybond-N+membrane (Amersham Pharmacia Biotech), and the hybridization and wash steps were performed at 50° C. Oligodeoxynucleotides used as Northern probes were 5'-32P-phosphorylated, complementary to the miRNA sequence and 20 to 25 nt in length.

5S rRNA was detected by ethidium staining of polyacrylamide gels prior to transfer. Blots were stripped by boiling in 0.1% aqueous sodium dodecylsulfate/0.1×SSC (15 mM sodium chloride, 1.5 mM sodium citrate, pH 7.0) for 10 min, and were re-probed up to 4 times until the 21-nt signals became too weak for detection. Finally, blots were probed for val-tRNA as size marker.

For analysis of *D. melanogaster* RNAs, total RNA was prepared from different developmental stages, as well as cultured Schneider-2 (S2) cells, which originally derive from 20-24 h *D. melanogaster* embryos [15] (FIG. 1. Table 1). miR-3 to miR-7 are expressed only during embryogenesis and not at later developmental stages. The temporal expression of miR-1, miR-2 and miR-8 to miR-13 was less restricted. These miRNAs were observed at all developmental stages though significant variations in the expression levels were sometimes observed. Interestingly, miR-1, miR-3 to miR-6, and miR-8 to miR-11 were completely absent from cultured Schneider-2 (S2) cells, which were originally derived from 20-24 h *D. melanogaster* embryos [15], while miR-2, miR-7, miR-12, and miR-13 were present in S2 cells, therefore indicating cell type-specific miRNA expression. miR-1, miR-8, and miR-12 expression patterns are similar to those of lin-4 stRNA in *C. elegans*, as their expression is strongly upregulated in larvae and sustained to adulthood [16]. miR-9 and miR-11 are present at all stages but are strongly reduced in the adult which may reflect a maternal contribution from germ cells or expression in one sex only.

The mir-3 to mir-6 genes are clustered (FIG. 2A), and mir-6 is present as triple repeat with slight variations in the mir-6 precursor sequence but not in the miRNA sequence itself. The expression profiles of miR-3 to miR-6 are highly similar (Table 1), which suggests that a single embryo-specific precursor transcript may give rise to the different miRNAs, or that the same enhancer regulates miRNA-specific promoters. Several other fly miRNAs are also found in gene clusters (FIG. 2A).

The expression of HeLa cell miR-15 to miR-33 was examined by Northern blotting using HeLa cell total RNA, in addition to total RNA prepared from mouse kidneys, adult zebrafish, *Xenopus laevis* ovary, and *D. melanogaster* S2 cells. (FIG. 1B, Table 2). miR-15 and miR-16 are encoded in a gene cluster (FIG. 2B) and are detected in mouse kidney, fish, and very weakly in frog ovary, which may result from miRNA expression in somatic ovary tissue rather than oocytes. mir-17 to mir-20 are also clustered (FIG. 2B), and are expressed in HeLa cells and fish, but undetectable in mouse kidney and frog ovary (FIG. 1, Table 2), and therefore represent a likely case of tissue-specific miRNA expression.

The majority of vertebrate and invertebrate miRNAs identified in this study are not related by sequence, but a few exceptions, similar to the highly conserved let-7 RNA [6], do exist. Sequence analysis of the *D. melanogaster* miRNAs revealed four such examples of sequence conservation between invertebrates and vertebrates. miR-1 homologs are encoded in the genomes of *C. elegans, C. briggsae*, and humans, and are found in cDNAs from zebrafish, mouse, cow and human. The expression of mir-1 was detected by Northern blotting in total RNA from adult zebrafish and *C. elegans*, but not in total RNA from HeLa cells or mouse kidney (Table 2 and data not shown). Interestingly, while mir-1 and let-7 are expressed both in adult flies (FIG. 1A) [6] and are both undetected in S2 cells, miR-1 is, in contrast to let-7, undetectable in HeLa cells. This represents another case of tissue-specific expression of a miRNA, and indicates that miRNAs may not only play a regulatory role in developmental timing, but also in tissue specification. miR-7 homologs were found by database searches in mouse and human genomic and expressed sequence tag sequences (ESTs). Two mammalian miR-7 variants are predicted by sequence analysis in mouse and human, and were detected by Northern blotting in HeLa cells and fish, but not in mouse kidney (Table 2). Similarly, we identified mouse and human miR-9 and miR-10 homologs by database searches but only detected mir-10 expression in mouse kidney.

The identification of evolutionary related miRNAs, which have already acquired multiple sequence mutations, was not possible by standard bioinformatic searches. Direct comparison of the *D. melanogaster* miRNAs with the human miRNAs identified an 11-nt segment shared between *D. melanogaster* miR-6 and HeLa miR-27, but no further relationships were detected. One may speculate that most miRNAs only act on a single target and therefore allow for rapid evolution by covariation, and that highly conserved miRNAs act on more than one target sequence, and therefore have a reduced probability for evolutionary drift by covariation [6]. An alternative interpretation is that the sets of miRNAs from *D. melanogaster* and humans are fairly incomplete and that many more miRNAs remain to be discovered, which will provide the missing evolutionary links.

lin-4 and let-7 stRNAs were predicted to be excised from longer transcripts that contain approximately 30 base-pair stem-loop structures [1, 6]. Database searches for newly identified miRNAs revealed that all miRNAs are flanked by sequences that have the potential to form stable stem-loop structures (FIGS. 3 and 4). In many cases, we were able to detect the predicted, approximately 70-nt precursors by Northern blotting (FIG. 1). Some miRNA precursor sequences were also identified in mammalian cDNA (EST) databases [27], indicating that primary transcripts longer than 70-nt stem-loop precursors do also exist. We never cloned a 22-nt RNA complementary to any of the newly identified miRNAs, and it is as yet unknown how the cellular processing machinery distinguishes between the miRNA and its complementary strand. Comparative analysis of the precursor stem-loop structures indicates that the loops adjacent to the base-paired miRNA segment can be located on either side of the miRNA sequence (FIGS. 3 and 4), suggesting that the 5' or 3' location of the stem-closing loop is not the determinant of miRNA excision. It is also unlikely that the structure, length or stability of the precursor stem is the critical determinant as the base-paired structures are frequently imperfect and interspersed by less stable, non-Watson-Crick base pairs such as G/A, U/U, C/U, A/A, and G/U wobbles. Therefore, a sequence-specific recognition process is a likely determinant for miRNA excision, perhaps mediated by members of the Argonaute (rde-1/ago1/piwi) protein family. Two members of this family, alg-1 and alg-2, have recently been shown to be critical for stRNA processing in *C. elegans* [13]. Members of the Argonaute protein family are also involved in RNAi and PTGS. In *D. melanogaster*, these include argonaute2, a component of the siRNA-endonuclease complex (RISC) [17], and its relative aubergine, which is important for silencing of repeat genes [18]. In other species, these include rde-1, argonaute1, and qde-2, in *C. elegans* [19], *Arabidopsis thaliana* [20], and *Neurospora crassa* [21], respectively. The Argonaute protein family therefore represents, besides the RNase III Dicer [12, 13], another evolutionary link between RNAi and miRNA maturation.

Despite advanced genome projects, computer-assisted detection of genes encoding functional RNAs remains problematic [22]. Cloning of expressed, short functional RNAs, similar to EST approaches (RNomics), is a powerful alternative and probably the most efficient method for identification of such novel gene products [23-26]. The number of functional RNAs has been widely underestimated and is expected to grow rapidly because of the development of new functional RNA cloning methodologies.

The challenge for the future is to define the function and the potential targets of these novel miRNAs by using bioinformatics as well as genetics, and to establish a complete catalogue of time- and tissue-specific distribution of the already identified and yet to be uncovered miRNAs. lin-4 and let-7 stRNAs negatively regulate the expression of proteins encoded by mRNAs whose 3' untranslated regions contain sites of complementarity to the stRNA [3-5].

Thus, a series of 33 novel genes, coding for 19- to 23-nucleotide microRNAs (miRNAs), has been cloned from fly embryos and human cells. Some of these miRNAs are highly conserved between vertebrates and invertebrates and are developmentally or tissue-specifically expressed. Two of the characterized human miRNAs may function as tumor suppressors in B-cell chronic lymphocytic leukemia. miRNAs are related to a small class of previously described 21- and 22-nt RNAs (lin-4 and let-7 RNAs), so-called small temporal RNAs (stRNAs), and regulate developmental timing in *C. elegans* and other species. Similar to stRNAs, miRNAs are presumed to regulate translation of specific target mRNAs by binding to partially complementary sites, which are present in their 3'-untranslated regions.

Deregulation of miRNA expression may be a cause of human disease, and detection of expression of miRNAs may become useful as a diagnostic. Regulated expression of miRNAs in cells or tissue devoid of particular miRNAs may be useful for tissue engineering, and delivery or transgenic expression of miRNAs may be useful for therapeutic intervention. miRNAs may also represent valuable drug targets itself. Finally, miRNAs and their precursor sequences may be engineered to recognize therapeutic valuable targets.

EXAMPLE 2 miRNAs from Mouse

To gain more detailed insights into the distribution and function of miRNAs in mammals, we investigated the tissue-specific distribution of miRNAs in adult mouse. Cloning of miRNAs from specific tissues was preferred over whole organism-based cloning because low-abundance miRNAs that normally go undetected by Northern blot analysis are identified clonally. Also, in situ hybridization techniques for detecting 21-nt RNAs have not yet been developed. Therefore, 19- to 25-nucleotide RNAs were cloned and sequenced from total RNA, which was isolated from 18.5 weeks old BL6 mice. Cloning of miRNAs was performed as follows: 0.2 to 1 mg of total RNA was separated on a 15% denaturing polyacrylamide gel and RNA of 19- to 25-nt size was recovered. A 5'-phosphorylated 3'-adapter oligonucleotide (5'-pUUUaac-cgcgaattccagx: uppercase, RNA; lowercase, DNA; p, phosphate; x, 3'-Amino-Modifier C-7, ChemGenes, Ashland, Ma, USA, Cat. No. NSS-1004; SEQ ID NO:54) and a 5'-adapter oligonucleotide (5'-acggaattcctcactAAA: uppercase, RNA; lowercase, DNA; SEQ ID NO:55) were ligated to the short RNAs. RT/PCR was performed with 3'-primer (5'-GAC-TAGCTGGAATTCGCGGTTAAA; SEQ ID NO:56) and 5'-primer (5'-CAGCCAACGGAATTCCTCACTAAA; SEQ ID NO:57). In order to introduce Ban I restriction sites, a second PCR was performed using the primer pair 5'-CAGC-CAACAGGCACCGAATTCCTCACTAAA (SEQ ID NO:57) and 5'-GACTAGCTTGGTGCCGAATTCGCGGT-TAAA (SEQ ID NO:56), followed by concatamerization after Ban I digestion and T4 DNA ligation. Concatamers of 400 to 600 basepairs were cut out from 1.5% agarose gels and recovered by Biotrap (Schleicher & Schuell) electroelution (1×TAE buffer) and by ethanol precipitation. Subsequently, the 3' ends of the concatamers were filled in by incubating for 15 min at 72° C. with Taq polymerase in standard PCR reaction mixture. This solution was diluted 3-fold with water and directly used for ligation into pCR2.1 TOPO vectors. Clones were screened for inserts by PCR and 30 to 50 samples were subjected to sequencing. Because RNA was prepared from combining tissues of several mice, minor sequence variations that were detected multiple times in multiple clones may reflect polymorphisms rather than RT/PCR mutations. Public database searching was used to identify the genomic sequences encoding the approx. 21-nt RNAs. The occurrence of a 20 to 30 basepair fold-back structure involving the immediate upstream or downstream flanking sequences was used to assign miRNAs [36-38].

We examined 9 different mouse tissues and identified 34 novel miRNAs, some of which are highly tissue-specifically expressed (Table 3 and FIG. 5). Furthermore, we identified 33 new miRNAs from different mouse tissues and also from human Soas-2 osteosarcoma cells (Table 4). miR-1 was previously shown by Northern analysis to be strongly expressed in adult heart, but not in brain, liver, kidney, lung or colon [37]. Here we show that miR-1 accounts for 45% of all mouse miRNAs found in heart, yet miR-1 was still expressed at a low level in liver and midbrain even though it remained undetectable by Northern analysis. Three copies or polymorphic alleles of miR-1 were found in mice. The conservation of tissue-specific miR-1 expression between mouse and human provides additional evidence for a conserved regulatory role of this miRNA. In liver, variants of miR-122 account for 72% of all cloned miRNAs and miR-122 was undetected in all other tissues analyzed. In spleen, miR-143 appeared to be most abundant, at a frequency of approx. 30%. In colon, miR-142-as, was cloned several times and also appeared at a frequency of 30%. In small intestine, too few miRNA sequences were obtained to permit statistical analysis. This was due to strong RNase activity in this tissue, which caused significant breakdown of abundant non-coding RNAs, e.g. rRNA, so that the fraction of miRNA in the cloned sequences was very low. For the same reason, no miRNA sequences were obtained from pancreas.

To gain insights in neural tissue miRNA distribution, we analyzed cortex, cerebellum and midbrain. Similar to heart, liver and small intestine, variants of a particular miRNA, miR-124, dominated and accounted for 25 to 48% of all brain miRNAs. miR-101, -127, -128, -131, and -132, also cloned from brain tissues, were further analyzed by Northern blotting and shown to be predominantly brain-specific. Northern blot analysis was performed as described in Example 1. tRNAs and 5S rRNA were detected by ethidium staining of polyacrylamide gels prior to transfer to verify equal loading. Blots were stripped by boiling in deionized water for 5 min, and reprobed up to 4 times until the 21-nt signals became too weak for detection.

miR-125a and miR-125b are very similar to the sequence of *C. elegans* lin-4 stRNA and may represent its orthologs (FIG. 6A). This is of great interest because, unlike let-7 that was readily detected in other species, lin-4 has acquired a few mutations in the central region and thus escaped bioinformatic database searches. Using the mouse sequence miR-125b, we could readily identify its ortholog in the *D. melanogaster* genome. miR-125a and miR-125b differ only by a central diuridine insertion and a U to C change. miR-125b is very similar to lin-4 stRNA with the differences located only in the central region, which is presumed to be bulged out during target mRNA recognition [41]. miR-125a and miR-125b were cloned from brain tissue, but expression was also detected by Northern analysis in other tissues, consistent with the role for lin-4 in regulating neuronal remodeling by controlling lin-14 expression [43]. Unfortunately, orthologs to *C. elegans* lin-14 have not been described and miR-125 targets remain to be identified in *D. melanogaster* or mammals. Finally, miR-125b expression is also developmentally regulated and only detectable in pupae and adult but not in embryo or larvae of *D. melanogaster* (FIG. 6B).

Sequence comparison of mouse miRNAs with previously described miRNA reveals that miR-99b and miR-99a are similar to *D. melanogaster*, mouse and human miR-10 as well as *C. elegans* miR-51, miR-141 is similar to *D. melanogaster* miR-8 miR-29b is similar to *C. elegans* miR-83, and miR-131 and miR-142-s are similar to *D. melanogaster* miR-4 and *C. elegans* miR-79 [36]. miR-124a is conserved between invertebrates and vertebrates. In this respect it should be noted that for almost every miRNA cloned from mouse was also encoded in the human genome, and frequently detected in other vertebrates, such as the pufferfish, *Fugu rubripes*, and the zebrafish, *Danio rerio*. Sequence conservation may point to conservation in function of these miRNAs. Comprehensive information about orthologous sequences is listed in FIG. 7.

In two cases both strands of miRNA precursors were cloned (Table 3), which was previously observed once for a *C. elegans* miRNA [36]. It is thought that the most frequently cloned strand of a miRNA precursor represents the functional miRNA, which is miR-30c-s and miR-142-as, s and as indicating the 5' or 3' side of the fold-back structure, respectively.

The mir-142 gene is located on chromosome 17, but was also found at the breakpoint junction of a t(8; 17) translocation, which causes an aggressive B-cell leukemia due to strong up-regulation of a translocated MYC gene [44]. The translocated MYC gene, which was also truncated at the first exon, was located only 4-nt downstream of the 3'-end of the miR-142 precursor. This suggests that translocated MYC was under the control of the upstream miR-142 promoter. Alignment of mouse and human miR-142 containing EST sequences indicate an approximately 20 nt conserved sequence element downstream of the mir-142 hairpin. This element was lost in the translocation. It is conceivable that the absence of the conserved downstream sequence element in the putative miR-142/mRNA fusion prevented the recognition of the transcript as a miRNA precursor and therefore may have caused accumulation of fusion transcripts and overexpression of MYC.

miR-155, which was cloned from colon, is excised from the known noncoding BIC RNA [47]. BIC was originally identified as a gene transcriptionally activated by promoter insertion at a common retroviral integration site in B cell lymphomas induced by avian leukosis virus. Comparison of BIC cDNAs from human, mouse and chicken revealed 78% identity over 138 nucleotides [47]. The identity region covers the miR-155 fold-back precursor and a few conserved boxes downstream of the fold-back sequence. The relatively high level of expression of BIC in lymphoid organs and cells in human, mouse and chicken implies an evolutionary conserved function, but BIC RNA has also been detected at low levels in non-hematopoietic tissues [47].

Another interesting observation was that segments of perfect complementarity to miRNAs are not observed in mRNA sequences or in genomic sequences outside the miRNA inverted repeat. Although this could be fortuitous, based on the link between RNAi and miRNA processing [11, 13, 43] it may be speculated that miRNAs retain the potential to cleave perfectly complementary target RNAs. Because translational control without target degradation could provide more flexibility it may be preferred over mRNA degradation.

In summary, 63 novel miRNAs were identified from mouse and 4 novel miRNAs were identified from human Soas-2 osteosarcoma cells (Table 3 and Table 4), which are conserved in human and often also in other non-mammalian vertebrates. A few of these miRNAs appear to be extremely tissue-specific, suggesting a critical role for some miRNAs in tissue-specification and cell lineage decisions. We may have also identified the fruitfly and mammalian ortholog of *C. elegans* lin-4 stRNA. The establishment of a comprehensive list of miRNA sequences will be instrumental for bioinformatic approaches that make use of completed genomes and the power of phylogenetic comparison in order to identify miRNA-regulated target mRNAs.

REFERENCES AND NOTES

1. R. C. Lee, R. L. Feinbaum, V. Ambros, Cell 75, 843 (1993).
2. B. J. Reinhart et al., Nature 403, 901 (2000).
3. V. Ambros, Curr. Opin. Genet. Dev. 10, 428 (2000),
4. E. G. Moss, Curr. Biol. 10, R436 (2000).
5. F. Slack, G. Ruvkun, Annu. Rev. Genet. 31, 611 (1997).
6. A. E. Pasquinelli et al., Nature 408, 86 (2000).
7. S. M. Elbashir et al., Nature 411, 494 (2001).
8. S. M. Elbashir, W. Lendeckel, T. Tuschl, Genes & Dev. 15, 188 (2001).
9. A. J. Hamilton, D. C. Baulcombe, Science 286, 950 (1999).
10. S. M. Hammond, E. Bernstein, D. Beach, G. J. Hannon, Nature 404, 293 (2000).
11. P. D. Zamore, T. Tuschl, P. A. Sharp, D. P. Bartel, Cell 101, 25 (2000).
12. G. Hutvágner, J. McLachlan, É. Bálint, T. Tuschl, P. D. Zamore, Science 93, 834 (2001).
13. A. Grishok et al., Cell 106, 23 (2001).
14. Cloning of 19- to 24-nt RNAs from *D. melanogaster* 0-2 h embryo lysate was performed as described (8). For cloning of HeLa miRNAs, 1 mg of HeLa total RNA was separated on a 15% denaturing polyacrylamide gel and RNA of 19- to 25-nt size was recovered. A 5' phosphorylated 3' adapter oligonucleotide (5 pUUUaaccgcgaattccagx: uppercase, RNA; lowercase, DNA; p, phosphate; x, 4-hydroxymethylbenzyl; SEQ ID NO:54) and a 5' adapter oligonucleotide (5' acggaattcctcactAAA: uppercase, RNA; lowercase, DNA; SEQ ID NO:55) ware ligated to the short HeLa cell RNAs. RT/PCR was performed with 3' primer (5' GACTAGCTGGAATTCGCGGTTAAA; SEQ ID NO:56) and 5' primer (5' CAGCCAACGGAATTCCTCACTAAA; SEQ ID NO:57), and followed by concatamerization after Eco RI digestion and T4 DNA ligation (8). After ligation of concatamers into pCR2.1 TOPO vectors, about 100 clones were selected and subjected to sequencing.
15. I. Schneider, J Embryol Exp. Morphol 27, 353 (1972).
16. R. Feinbeum, V. Ambros, Dev. Biol. 210, 87 (1999).
17. S. M. Hammond, S. Boettcher, A. A. Caudy, R. Kobayashi, G. J. Hannon, Science 293, 1146 (2001).
18. A. A. Aravin et al., Curr. Biol. 11, 1017 (2001).
19. H. Tabara et al., Cell 99, 123 (1999).
20. M. Fagard, S. Boutet, J. B. Morel, C. Bellini, H. Vaucheret, Proc. Natl. Acad. Sci. USA 97, 11650 (2000).
21. C. Catalanotto, G. Azzalin, G. Macino, C. Cogoni, Nature 404, 245 (2000).
22. S. R. Eddy, Curr. Opin. Genet. Dev. 9, 695 (1999).
23. J. Cavaille et al., Proc. Natl. Acad. Sci. USA 97, 14311 (2000).
24. A. Hüttenhofer et al., EMBO J. 20, 2943 (2001).
25. L. Argaman et al., Curr. Biol. 11, 941 (2001).
26. K. M. Wasserman, F. Repoila, C. Rosenow, G. Storz, S. Gottesman, Genes & Dev, 15, 1637 (2001).
27. Supplementary Web material is available on Science Online at www.sciencemag.org/cgi/content/full/xxx
28. D. H. Mathews, J. Sabina, M. Zuker, D. H. Turner, J. Mol. Biol. 288, 911 (1999).
29. E. Bernstein, A. A. Caudy, S. M. Hammond, G. J. Hannon, Nature 409, 363 (2001).
30. Graham, F. L. and van der Eb, A. J., (1973), Virol. 52, 456.
31. McCutchan, J. H. and Pagano, J. S., (1968), J. Natl. Cancer Inst. 41, 351.
32. Chu, G. et al., (1987), Nucl. Acids Res. 15, 1311.
33. Fraley, R. et al., (1980), J. Biol. Chem. 255, 10431.
34. Capecchi, M. R., (1980), Cell 22, 479.
35. Felgner, P. L. et al., (1987), Proc. Natl. Acad. Sci USA 84, 7413.
36. Lau N. C., Lim L. P., Weinstein E. G., Bartel D. P., (2001), Science 294, 858-862.
37, Lee R. C., Ambros V., (2001), Science 294, 862-864.
38. Ambros V., (2001), Cell 107, 823-826.
39. Ambros V., Horvitz H. R., (1984), Science 226, 409-416.
40. Wightman B., Ha I., Ruvkun G., (1993), Cell 75, 855-862.
41. Rougvie A. E., (2001), Nat. Rev. Genet. 2, 690-701.

42. Ketting R. F., Fischer S. E., Bernstein E., Sijen T., Hannon G. J., Plasterk R. H., (2001), Genes & Dev. 15, 2654-2659.
43. Hallam S. J., Jin. Y., (1998), Nature 395, 78-82.
44. Gauwerky C. E., Huebner K., Isobe M.; Nowell P. C., Croce C. M., (1989), Proc. Natl. Acad. Sci. USA 86, 8867-8871.
45. P. Chomczynski, N. Sacchi, Anal Biochem 162, 156, (1987).
46. Mourelatos Z., Dostie J., Paushkin S., Sharma A., Charroux B., Abel L., J. R., Mann M., Dreyfuss G., (2002), Genes & Dev., in press.
47. Tam W., (2001), Gene 274, 157-167.

TABLE 1

*D. melanogaster* miRNAs. The sequences given represent the most abundant, and typically longest miRNA sequence identified by cloning; miRNAs frequently vary in length by one or two nucleotides at their 3' termini. From 222 short RNAs sequenced, 69 (31%) corresponded to miRNAs, 103 (46%) to already characterized functional RNAs (rRNA, 7SL RNA, tRNAs), 30 (14%) to transposon RNA fragments, and 20 (10%) sequences with no database entry. The frequency (freq.) for cloning a particular miRNA relative to all identified miRNAs is indicated in percent. Results of Northern blotting of total RNA isolated from staged populations of *D. melanogaster* are summarized. E, embryo; L; larval stage; P; pupae; A, adult; S2, Schneider-2 cells. The strength of the signal within each blot is represented from strongest (+++) to undetected (-). let-7 stRNA was probed as control. Genbank accession numbers and homologs of miRNAs identified by database searching in other species are provided as supplementary material.

| miRNA | sequence (5' to 3') | freq. (%) | E 0-3 h | E 0-6 h | L1 + L2 | L3 | P | A | S2 |
|---|---|---|---|---|---|---|---|---|---|
| miR-1 | UGGAAUGUAAAGAAGUAUGGAG (SEQ ID NO: 58) | 32 | + | + | ++ + | ++ + | ++ | ++ + | - |
| miR-2a* | UAUCACAGCCAGCUUUGAUGAGC (SEQ ID NO: 59) | 3 | | | | | | | |
| miR-2b* | UAUCACAGCCAGCUUUGAGGAGC (SEQ ID NO: 60) | 3 | ++ | ++ | ++ | ++ + | ++ | + | ++ + |
| miR-3 | UCACUGGGCAAAGUGUGUCUCA# | 9 | +++ | +++ | - | - | - | - | - |
| miR-4 | AUAAAGCUAGACAACCAUUGA (SEQ ID NO: 62) | 6 | +++ | +++ | - | - | - | - | - |
| miR-5 | AAAGGAACGAUCGUUGUGAUAUG (SEQ ID NO: 63) | 1 | +++ | +++ | +/- | +/- | - | - | - |
| miR-6 | UAUCACAGUGGCUGUUCUUUUU (SEQ ID NO: 64) | 13 | +++ | +++ | +/- | +/- | - | - | - |
| miR-7 | UGGAAGACUAGUGAUUUUGUUGU (SEQ ID NO: 65) | 4 | +++ | ++ | +/- | +/- | +/- | +/- | +/- |
| miR-8 | UAAUACUGUCAGGUAAAGAUGUC (SEQ ID NO: 66) | 3 | +/- | +/- | ++ + | ++ + | + | ++ + | - |
| miR-9 | UCUUUGGUUAUCUAGCUGUAUGA (SEQ ID NO: 67) | 7 | +++ | ++ | ++ + | ++ + | ++ + | +/- | - |
| miR-10 | ACCCUGUAGAUCCGAAUUUGU (SEQ ID NO: 68) | 1 | + | + | ++ | ++ + | +/- | + | - |
| miR-11 | CAUCACAGUCUGAGUUCUUGC (SEQ ID NO: 69) | 7 | +++ | +++ | ++ + | ++ + | ++ + | + | - |
| miR-12 | UGAGUAUUACAUCAGGUACUGGU (SEQ ID NO: 70) | 7 | + | + | ++ | ++ | + | ++ + | +/- |
| miR-13a* | UAUCACAGCCAUUUUGACGAGU (SEQ ID NO: 71) | 1 | +++ | +++ | ++ + | ++ + | + | ++ + | ++ + |
| miR-13b* | UAUCACAGCCAUUUUGAUGAGU (SEQ ID NO: 72) | 0 | | | | | | | |

TABLE 1-continued

*D. melanogaster* miRNAs. The sequences given represent the most abundant, and typically longest miRNA sequence identified by cloning; miRNAs frequently vary in length by one or two nucleotides at their 3' termini. From 222 short RNAs sequenced, 69 (31%) corresponded to miRNAs, 103 (46%) to already characterized functional RNAs (rRNA, 7SL RNA, tRNAs), 30 (14%) to transposon RNA fragments, and 20 (10%) sequences with no database entry. The frequency (freq.) for cloning a particular miRNA relative to all identified miRNAs is indicated in percent. Results of Northern blotting of total RNA isolated from staged populations of *D. melanogaster* are summarized. E, embryo; L; larval stage; P; pupae; A, adult; S2, Schneider-2 cells. The strength of the signal within each blot is represented from strongest (+++) to undetected (−). let-7 stRNA was probed as control. Genbank accession numbers and homologs of miRNAs identified by database searching in other species are provided as supplementary material.

| miRNA | sequence (5' to 3') | freq. (%) | E 0-3 h | E 0-6 h | L1 + L2 | L3 | P | A | S2 |
|---|---|---|---|---|---|---|---|---|---|
| miR-14 | UCAGUCUUUUUCUCUCUCCUA (SEQ ID NO: 73) | 1 | − | − | − | − | − | −− | − |
| let-7 | UGAGGUAGUAGGUUGUAUAGUU (SEQ ID NO: 74) | 0 | − | − | − | − | ++ + | ++ + | − |

# = (SEQ ID NO: 61)
*Similar miRNA sequences are difficult to distinguish by Northern blotting because of potential cross-hybridization of probes.

TABLE 2

Human miRNAs. From 220 short RNAs sequenced, 100 (45%) corresponded to miRNAs, 53 (24%) to already characterized functional RNAs (rRNA, snRNAs, tRNAs), and 67 (30%) sequences with no database entry. Results of Northern blotting Of total RNA isolated from different vertebrate species and S2 cells are indicated. For legend, see Table 1.

| miRNA | sequence (5' to 3') | freq. % | HeLa cells | mouse kidney | adult fish | frog ovary | S2 |
|---|---|---|---|---|---|---|---|
| let-7a* | UGAGGUAGUAGGUUGUAUAGUU# | 10 | +++ | +++ | +++ | − | − |
| let-7b* | UGAGGUAGUAGGUUGUGUGGUU (SEQ ID NO: 76) | 13 | | | | | |
| let-7c* | UGAGGUAGUAGGUUGUAUGGUU (SEQ ID NO: 77) | 3 | | | | | |
| let-7d* | AGAGGUAGUAGGUUGCAUAGU (SEQ ID NO: 78) | 2 | +++ | +++ | +++ | − | − |
| let-7e* | UGAGGUAGGAGGUUGUAUAGU (SEQ ID NO: 79) | 2 | +++ | +++ | +++ | − | − |
| let-7f* | UGAGGUAGUAGAUUGUAUAGUU (SEQ ID NO: 80) | 1 | | | | | |
| miR-15 | UAGCAGCACAUAAUGGUUUGUG (SEQ ID NO: 81) | 3 | +++ | ++ | + | +/− | − |
| miR-16 | UAGCAGCACGUAAAUAUUGGCG (SEQ ID NO: 82) | 10 | +++ | + | +/− | +/− | − |
| miR-17 | ACUGCAGUGAAGGCACUUGU (SEQ ID NO: 83) | 1 | +++ | − | − | − | − |
| miR-18 | UAAGGUGCAUCUAGUGCAGAUA (SEQ ID NO: 84) | 2 | +++ | − | − | − | − |
| miR-19a* | UGUGCAAAUCUAUGCAAAACUGA (SEQ ID NO: 85) | 1 | +++ | − | +/− | − | − |
| miR-19b* | UGUGCAAAUCCAUGCAAAACUGA (SEQ ID NO: 86) | 3 | | | | | |
| miR-20 | UAAAGUGCUUAUAGUGCAGGUA (SEQ ID NO: 87) | 4 | +++ | − | + | − | − |

TABLE 2-continued

Human miRNAs. From 220 short RNAs sequenced, 100 (45%) corresponded to miRNAs, 53 (24%) to already characterized functional RNAs (rRNA, snRNAs, tRNAs), and 67 (30%) sequences with no database entry. Results of Northern blotting Of total RNA isolated from different vertebrate species and S2 cells are indicated. For legend, see Table 1.

| miRNA | sequence (5' to 3') | freq. % | HeLa cells | mouse kidney | adult fish | frog ovary | S2 |
|---|---|---|---|---|---|---|---|
| miR-21 | UAGCUUAUCAGACUGAUGUUGA (SEQ ID NO: 88) | 10 | +++ | + | ++ | - | - |
| miR-22 | AAGCUGCCAGUUGAAGAACUGU (SEQ ID NO: 89) | 10 | +++ | +++ | + | +/- | - |
| miR-23 | AUCACAUUGCCAGGGAUUUCC (SEQ ID NO: 90) | 2 | +++ | +++ | +++ | + | - |
| miR-24 | UGGCUCAGUUCAGCAGGAACAG (SEQ ID NO: 91) | 4 | ++ | +++ | ++ | - | - |
| miR-25 | CAUUGCACUUGUCUCGGUCUGA (SEQ ID NO: 92) | 3 | +++ | + | ++ | - | - |
| miR-26a* | UUCAAGUAAUCCAGGAUAGGCU (SEQ ID NO: 93) | 2 | + | ++ | +++ | - | - |
| miR-26b* | UUCAAGUAAUUCAGGAUAGGUU (SEQ ID NO: 94) | 1 | | | | - | |
| miR-27 | UUCACAGUGGCUAAGUUCCGCU (SEQ ID NO: 95) | 2 | +++ | +++ | ++ | - | - |
| miR-28 | AAGGAGCUCACAGUCUAUUGAG (SEQ ID NO: 96) | 2 | +++ | +++ | - | - | - |
| miR-29 | CUAGCACCAUCUGAAAUCGGUU (SEQ ID NO: 97) | 2 | + | +++ | +/- | - | - |
| miR-30 | CUUUCAGUCGGAUGUUUGCAGC (SEQ ID NO: 98) | 2 | +++ | +++ | +++ | - | - |
| miR-31 | GGCAAGAUGCUGGCAUAGCUG (SEQ ID NO: 99) | 2 | +++ | - | - | - | - |
| miR-32 | UAUUGCACAUUACUAAGUUGC (SEQ ID NO: 100) | 1 | - | - | - | - | - |
| miR-33 | GUGCAUUGUAGUUGCAUUG (SEQ ID NO: 101) | 1 | - | - | - | - | - |
| miR-1 | UGGAAUGUAAAGAAGUAUGGAG (SEQ ID NO: 102) | 0 | - | - | + | - | - |
| miR-7 | UGGAAGACUAGUGAUUUUGUUGU (SEQ ID NO: 103) | 0 | + | - | +/- | - | +/- |
| miR-9 | UCUUUGGUUAUCUAGCUGUAUGA (SEQ ID NO: 104) | 0 | - | - | - | - | - |
| miR-10 | ACCCUGUAGAUCCGAAUUUGU (SEQ ID NO: 105) | 0 | - | + | - | - | - |

# = (SEQ ID NO: 75)
*Similar miRNA sequences are difficult to distinguish by Northern blotting because of potential cross-hybridization of probes.

TABLE 3

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

| miRNA | sequence (5' to 3') | ht | lv | sp | si | co | cx | cb | mb |
|---|---|---|---|---|---|---|---|---|---|
| let-7a | UGAGGUAGUAGGUUGUAUAGUU (SEQ ID NO: 106) | | 3 | | | 1 | 1 | | 7 |
| let-7b | UGAGGUAGUAGOVUGUGUGGUU (SEQ ID NO: 107) | | 1 | 1 | | | | 2 | 5 |
| let-7c | UGAGGUAGUAGGUUGUAUGGUU (SEQ ID NO: 108) | | 2 | | | | 2 | 5 | 19 |
| let-7d | AGAGGUAGUAGGUUGCAUAGU (SEQ ID NO: 109) | 2 | | | | 2 | 2 | | 2 |
| let-7e | UGAGGUAGGAGGUUGUAUAGU (SEQ ID NO: 110) | | | 1 | | | | | 2 |
| let-7f | UGAGGUAGUAGAUUGUAUAGUU (SEQ ID NO: 111) | | | 2 | | | | 3 | 3 |
| let-7g | UGAGGUAGUAGUUUGUACAGUA (SEQ ID NO: 112) | | | | | | 1 | 1 | 2 |
| let-7h | UGAGGUAGUAGUGUGUGCAGUU (SEQ ID NO: 113) | | | | | | 1 | 1 | |
| let-7i | UGAGGUAGUAGUUUGUGCU (SEQ ID NO: 114) | | | | | | 1 | 1 | |
| miR-1b | UGGAAUGUAAAGAAGUAUGUAA (SEQ ID NO: 115) | 4 | 2 | | | | | | 1 |
| miR-1c | UGGAAUGUAAAGAAGUAUGUAC (SEQ ID NO: 116) | 7 | | | | | | | |
| miR-1d | UGGAAUGUAAAGAAGUAUGUAUU (SEQ ID NO: 117) | 16 | | | | | | | 1 |
| miR-9 | UCUUUGGUUAUCUAGCUGUAUGA (SEQ ID NO: 118) | | | | | | 3 | 4 | 4 |
| miR-15a | UAGCAGCACAUAAUGGUUUGUG (SEQ ID NO: 119) | 1 | | | | | | | 2 |
| miR-15b | UAGCAGCACADCAUGGUUUACA (SEQ ID NO: 120) | 1 | | | | | | | |
| miR-16 | UAGCAGCACGUAAAUAUUGGCG (SEQ ID NO: 121) | 1 | | | 1 | 2 | 1 | 2 | 3 |
| miR-18 | UAAGGUGCAUCUAGUGCAGAUA (SEQ ID NO: 122) | | | | 1 | | | | |
| miR-19b | UGUGCAAAUCCAUGCAAAACUGA (SEQ ID NO: 123) | | | | 1 | | | | |
| miR-20 | UAAAGUGCUUAUAGUGCAGGUAG (SEQ ID NO: 124) | | | | | 1 | | | |
| miR21 | UAGCUUAUCAGACUGAUGUUGA (SEQ ID NO: 125) | 1 | | 1 | 2 | 1 | | | |

TABLE 3-continued

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

| miRNA | sequence (5' to 3') | Number of clones | | | | | | | |
|---|---|---|---|---|---|---|---|---|---|
| | | ht | lv | sp | si | co | cx | cb | mb |
| miR-22 | AAGCUGCCAGUUGAAGAACUGU (SEQ ID NO: 126) | 2 | 1 | | 1 | | | 1 | 2 |
| miR-23a | AUCACAUUGCCAGGGAUUUCC (SEQ ID NO: 127) | 1 | | | | | | | |
| miR-23b | AUCACAUUGCCAGGGAUUACCAC (SEQ ID NO: 128) | | | | | | 1 | | |
| miR-24 | UGGCUCAGUUCAGCAGGAACAG (SEQ ID NO: 129) | 1 | | | | 1 | 1 | | 1 |
| miR-26a | UUCAAGUAAUCCAGGAUAGGCU (SEQ ID NO: 130) | | | | | | | 3 | 2 |
| miR-26b | UUCAAGUAAUUCAGGAUAGGUU (SEQ ID NO: 131) | | 2 | | | | 4 | 1 | |
| miR-27a | UUCACAGUGGCUAAGUUCCGCU (SEQ ID NO: 132) | 1 | | 2 | | 1 | 1 | 2 | 1 |
| miR-27b | UUCACAGUGGCUAAGUUCUG (SEQ ID NO: 133) | | | | | | | | 1 |
| miR-29a | CUAGCACCAUCUGAAAUCGGUU (SEQ ID NO: 134) | 1 | | | | 1 | | 1 | |
| miR-29b/miR-102 | UAGCACCAUUUGAAAUCAGUGUU (SEQ ID NO: 135) | 1 | | | | 1 | 5 | | 3 |
| miR29c/ | UAGCACCAUUUGAAAUCGGUUA (SEQ ID NO: 136) | 1 | | | | | 3 | | 1 |
| miR-30a-s/miR-97 | UGUAAACACCUCGACUGGAAGC (SEQ ID NO: 137) | | | 1 | | | 1 | | 1 |
| miR-30a-as[a] | CUUUCAGUCGGAUGUUUGCAGC (SEQ ID NO: 138) | | | | | | | 1 | |
| miR-30b | UGUAAACAUCCUACACUCAGC (SEQ ID NO: 139 | | | 1 | | | | 2 | |
| miR-30c | UGUAAACAUCCUACACUCUCAGC (SEQ ID NO: 140) | 2 | | | | | 1 | 1 | |
| miR-30d | UGUAAACAUCCCCGACUGGAAG (SEQ ID NO: 141) | | | 1 | | | | | |
| miR-99a/miR-99 | ACCCGUAGAUCCGAUCUUGU (SEQ ID NO: 142) | | | | | | 1 | | |
| miR-99b | CACCCGUAGAACCGACCUUGCG (SEQ ID NO: 143) | | | | | | | 1 | |
| miR-101 | UACAGUACUGUGAUAACUGA (SEQ ID NO: 144) | | | | | | 2 | 1 | 1 |

TABLE 3-continued

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

| miRNA | sequence (5' to 3') | ht | lv | sp | si | co | cx | cb | mb |
|---|---|---|---|---|---|---|---|---|---|
| miR-122a | UGGAGUGUGACAAUGGUGUUUGU (SEQ ID NO: 145) | | 3 | | | | | | |
| miR-122b | UGGAGUGUGACAAUGGUGUUUGA (SEQ ID NO: 146) | | 11 | | | | | | |
| miR-122a, b | UGGAGUGUGACAAUGGUGUUUG (SEQ ID NO: 147) | | 23 | | | | | | |
| miR-123 | CAUUAUUACUUUUGGUACGCG (SEQ ID NO: 148) | 1 | 2 | | | | | | |
| miR-124a[b] | UUAAGGCACGCGG-UGAAUGCCA (SEQ ID NO: 149) | | | | 1 | | 37 | 41 | 24 |
| miR-124b | UUAAGGCACGCGGGUGAAUGC (SEQ ID NO: 150) | | | | | | | 1 | 3 |
| miR-125a | UCCCUGAGACCCUUUAACCUGUG (SEQ ID NO: 151) | | | | | | | 1 | 1 |
| miR-125b | UCCCUGAGACCCU--AACUUGUGA (SEQ ID NO: 152) | | | | | | | 1 | |
| miR-126 | UCGUACCGUGAGUAAUAAUGC (SEQ ID NO: 153) | 4 | | | | | | 1 | |
| miR-127 | UCGGAUCCGUCUGAGCUUGGCU (SEQ ID NO: 154) | | | | | | | 1 | |
| miR-128 | UCACAGUGAACCGGUCUCUUUU (SEQ ID NO: 155) | | | | | | | 2 | 2 | 2 |
| miR-129 | CUUUUUUCGGUCUGGGCUUGC (SEQ ID NO: 156) | | | | | | | 1 | |
| miR-130 | CAGUGCAAUGUUAAAAGGGC (SEQ ID NO: 157) | | | | | | | 1 | |
| miR-131 | UAAAGCUAGAUAACCGAAAGU (SEQ ID NO: 158) | | | | | | | 1 | 1 | 1 |
| miR-132 | UAACAGUCUACAGCCAUGGUCGU (SEQ ID NO: 159) | | | | | | | 1 | |
| miR-133 | UUGGUCCCCUUCAACCAGCUGU (SEQ ID NO: 160) | 4 | | | | | | 1 | |
| miR-134 | UGUGACUGGUUGACCAGAGGGA (SEQ ID NO: 161) | | | | | | | 1 | |
| miR-135 | UAUGGCUUUUUAUUCCUAUGUGAA (SEQ ID NO: 162) | | | | | | | 1 | |
| miR-136 | ACUCCAUUUGUUUUGAUGAUGGA (SEQ ID NO: 163) | | | | | | | 1 | |
| miR-137 | UAUUGCUUAAGAAUACGCGUAG (SEQ ID NO: 164) | | | | | | | 1 | 1 |

TABLE 3-continued

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

| miRNA | sequence (5' to 3') | ht | lv | sp | si | co | cx | cb | mb |
|---|---|---|---|---|---|---|---|---|---|
| miR-138 | AGCUGGUGUUGUGAAUC (SEQ ID NO: 165) | | | | | | 1 | | |
| miR-139 | UCUACAGUGCACGUGUCU (SEQ ID NO: 166) | | | | | 1 | 1 | | |
| miR-140 | AGUGGUUUUACCCUAUGGUAG (SEQ ID NO: 167) | | | | 1 | | | | |
| miR-141 | AACACUGUCUGGUAAAGAUGG (SEQ ID NO: 168) | | | 1 | 1 | | 1 | | |
| miR-142-s | CAUAAAGUAGAAAGCACUAC (SEQ ID NO: 169) | | | | 1 | 1 | | | |
| miR-142as[b] | UGUAGUGUUUCCUACUUUAUGG (SEQ ID NO: 170) | | | 1 | 1 | 6 | | | |
| miR-143 | UGAGAUGAAGCACUGUAGCUCA (SEQ ID NO: 171) | 3 | | 7 | | | 2 | | 1 |
| miR-144 | UACAGUAUAGAUGAUGUACUAG (SEQ ID NO: 172) | 2 | | | | 1 | | | |
| miR-145 | GUCCAGUUUUCCCAGGAAUCCCUU (SEQ ID NO: 173) | 1 | | | | | | | |
| miR-146 | UGAGAACUGAAUUCCAUGGGUUU (SEQ ID NO: 174) | 1 | | | | | | | |
| miR-147 | GUGUGUGGAAAUGCUUCUGCC (SEQ ID NO: 175) | | | | 1 | | | | |
| miR-148 | UCAGUGCACUACAGAACUUUGU (SEQ ID NO: 176) | | | | 1 | | | | |
| miR-149 | UCUGGCUCCGUGUCUUCACUCC (SEQ ID NO: 177) | 1 | | | | | | | |
| miR-150 | UCUCCCAACCCUUGUACCAGUGU (SEQ ID NO: 178) | | | | | | 1 | | |
| miR-151 | CUAGACUGAGGCUCCUUGAGGU (SEQ ID NO: 179) | | | | | | 1 | | |
| MiR-152 | UCAGUGCAUGACAGAACUUGG (SEQ ID NO: 180) | | | | | | 1 | | |
| miR-153 | UUGCAUAGUCACAAAAGUGA (SEQ ID NO: 181) | | | | | | | | 1 |

TABLE 3-continued

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

| miRNA | sequence (5' to 3') | ht | lv | sp | si | co | cx | cb | mb |
|---|---|---|---|---|---|---|---|---|---|
| miR-154 | UAGGUUAUCCGUGUUGCCUUCG (SEQ ID NO: 182) | | | | | | | | 1 |
| miR-155 | UUAAUGCUAAUUGUGAUAGGGG (SEQ ID NO: 183) | | | | | 1 | | | |

[a] The originally described miR-30 was renamed to mir-30a-as in order to distinguish it from the miRNA derived from the opposite strand of the precursor encoded by the mir-30a gene. miR-30a-s is equivalent to miR-97 [46].
[b] A 1-nt length heterogeneity as found on both 5' and 3' end. The 22-nt miR sequence is shown, but only 21-nt miRNAs were cloned.

TABLE 4

Mouse and human miRNAs. The sequences indicated represent the longest miRNA sequences identified by cloning. The 3' terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes; which are accommodated as G-U wobble base pairs during target recognition. Mouse brains were dissected into midbrain, mb, cortex, cx, cerebellum, cb. The tissues analyzed were lung, ln; liver, lv; spleen, sp; kidney, kd; skin, sk; testis, ts; ovary, ov; thymus, thy; eye, ey; cortex, ct; cerebellum, cb; midbrain, mb. The human osteosarcoma cells SAOS-2 cells contained an inducible p53 gene (p53-, uninduced p53; p53+, induced p53); the differences in miRNAs identified from induced and uninduced SAOS cells were not statistically significant.

| miRNA | Sequence (5' to 3') | ln | lv | sp | kd | sk | ts | ov | thy | ey | p53- | p53+ | |
|---|---|---|---|---|---|---|---|---|---|---|---|---|---|
| miR-C1 | AACAUUCAACGCUGUCGGUGAGU | 1 | | 1 | | | 2 | | | | | | (SEQ ID NO. 184) |
| miR-C2 | UUUGGCAAUGGUAGAACUCACA | | | | | | | 1 | | | | | (SEQ ID NO. 185) |
| miR-C3 | UAUGGCACUGGUAGAAUUCACUG | | | | | | | 1 | | | | | (SEQ ID NO. 186) |
| miR-C4 | CUUUUUGCCGUCUGGGCUUGUU | | | | | 1 | | 1 | 1 | | | | (SEQ ID NO. 187) |
| miR-C5 | UGGACGGAGAACUGAUAAGGGU | | | | | | | 2 | | | | | (SEQ ID NO. 188) |
| miR-C6 | UGGAGAGAAAGGCAGUUC | | | | | | | 1 | | | | | (SEQ ID NO. 189) |
| miR-C7 | CAAAGAAUUCUCCUUUUGGGCUU | | | | | | | 1 | 1 | | | | (SEQ ID NO. 190) |
| miR-C8 | UCGUGUCUUGUGUUGCAGCCGG | | | | | 1 | | | | | | | (SEQ ID NO. 191) |
| miR-C9 | UAACACUGUCUGGUAACGAUG | | | | | 1 | | | | | | | (SEQ ID NO. 192) |
| miR-C10 | CAUCCCUUGCAUGGUGGAGGGU | | | | | 1 | | | | | | | (SEQ ID NO. 193) |

TABLE 4-continued

Mouse and human miRNAs. The sequences indicated represent the longest miRNA sequences identified by cloning. The 3' terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes; which are accommodated as G-U wobble base pairs during target recognition. Mouse brains were dissected into midbrain, mb, cortex, cx, cerebellum, cb. The tissues analyzed were lung, ln; liver, lv; spleen, sp; kidney, kd; skin, sk; testis, ts; ovary, ov; thymus, thy; eye, ey; cortex, ct; cerebellum, cb; midbrain, mb. The human osteosarcoma cells SAOS-2 cells contained an inducible p53 gene (p53-, uninduced p53; p53+, induced p53); the differences in miRNAs identified from induced and uninduced SAOS cells were not statistically significant.

| | | number of clones | | | | | | | | | | |
|---|---|---|---|---|---|---|---|---|---|---|---|---|
| | | mouse tissues | | | | | | | | human SAOS-2 cells | | |
| miRNA | Sequence (5' to 3') | ln | lv | sp | kd | sk | ts | ov | thy | ey | p53- | p53+ | |
| miR-C11 | GUGCCUACUGAGCUGACAUCAGU | | | 1 | | | | | | | | | (SEQ ID NO. 194) |
| miR-C12 | UGAUAUGUUUGAUAUAUUAGGU | | | 2 | | | | | | | | | (SEQ ID NO. 195) |
| miR-C13 | CAACGGAAUCCCAAAAGCAGCU | | | 2 | 1 | | | | | | | | (SEQ ID NO. 196) |
| miR-C14 | CUGACCUAUGAAUUGACA | | 2 | | 1 | | | | | | | | (SEQ ID NO. 197) |
| miR-C15 | UACCACAGGGUAGAACCACGGA | | | 1 | | | | | | | | | (SEQ ID NO. 198) |
| miR-C16 | AACUGGCCUACAAAGUCCCAG | | | 1 | | | | | | | | | (SEQ ID NO. 199) |
| miR-C17 | UGUAACAGCAACUCCAUGUGGA | | | 1 | | | | | | | | | (SEQ ID NO. 200) |
| miR-C18 | UAGCAGCACAGAAAUAUUGGC | 2 | | 1 | 1 | | | | | | | | (SEQ ID NO. 201) |
| miR-C19 | UAGGUAGUUUCAUGUUGUUGG | | | | | | | | 1 | | | | (SEQ ID NO. 202) |
| miR-C20 | UUCACCACCUUCUCCACCCAGC | | | | | | | | 1 | | 1 | | (SEQ ID NO. 203) |
| miR-C21 | GGUCCAGAGGGGAGAUAGG | | | | | | | | 1 | | | | (SEQ ID NO. 204) |
| miR-C22 | CCCAGUGUUCAGACUACCUGUU | | | | | | | | 1 | | | | (SEQ ID NO. 205) |
| miR-C23 | UAAUACUGCCUGGUAAUGAUGAC | 2 | | | | 1 | | | | | | | (SEQ ID NO. 206) |
| miR-C24 | UACUCAGUAAGGCAUUGUUCU | | | | | 1 | | | | | | | (SEQ ID NO. 207) |
| miR-C25 | AGAGGUAUAGCGCAUGGGAAGA | | | | | 1 | | | | | | | (SEQ ID NO. 208) |
| miR-C26 | UGAAAUGUUUAGGACCACUAG | | | | | 1 | | | | | | | (SEQ ID NO. 209) |
| miR-C27 | UUCCCUUUGUCAUCCUAUGCCUG | | | | | | | 1 | | | | | (SEQ ID NO. 210) |
| miR-C28 | UCCUUCAUUCCACCGGAGUCUG | | | 1 | | | | | | | | | (SEQ ID NO. 211) |
| miR-C29 | GUGAAAUGUUUAGGACCACUAGA | | | 2 | | | | | | | | | (SEQ ID NO. 212) |
| miR-C30 | UGGAAUGUAAGGAAGUGUGUGG | | | 2 | | | | | | | | | (SEQ ID NO. 213) |
| miR-C31 | UACAGUAGUCUGCACAUUGGUU | | | 1 | | | | | | | | | (SEQ ID NO. 214) |
| miR-C32 | CCCUGUAGAACCGAAUUUGUGU | | | 1 | 1 | | | | | | | | (SEQ ID NO. 215) |
| miR-C33 | AACCCGUAGAUCCGAACUUGUGAA | | | 1 | | | | | | | | | (SEQ ID NO. 216) |
| miR-C34 | GCUUCUCCUGGCUCUCCUCCCUC | | | | | | | 1 | | | | | (SEQ ID NO. 217) |

TABLE 5

*D. melanogaster* miRNA sequences and genomic location. The sequences given represent the most abundant, and typically longest miRNA sequences identified by cloning. It was frequently observed that miRNAs vary in length by one or two nucleotides at their 3'-terminus. From 222 short RNAs sequenced; 69 (31%) corresponded to miRNAs, 103 (46%) to already characterized functional RNAs (rRNA, 7SL RNA, tRNAs), 30 (14%) to transposon RNA fragments, and 20 (10%) sequences with no database entry. RNA sequences with a 5'-guanosine are likely to be underrepresented due to the cloning procedure (8). miRNA homologs found in other species are indicated. Chromosomal location (chr.) and GenBank accession numbers (acc. nb.) are indicated. No ESTs matching miR-1 to miR-14 were detectable by database searching.

| miRNA | sequence (5' to 3') | chr., acc. nb. | remarks |
|---|---|---|---|
| miR-1 | UGGAAUGUAAAGAAGUAUGGAG (SEQ ID NO: 58) | 2L, AE003667 | homologs: *C. briggsae*, G20U, AC87074; *C. elegans* G20U, U97405; mouse, G20U, G22U, AC020867; human, chr. 20, G20U, G22U, AL449263; ESTs: zebrafish, G20U, G22U, BF157-601; cow, G20U, G22U, BE722-224; human, G20U, G22U, AL220268 |
| miR-2a | UAUCACAGCCAGCUUUGAUGAGC (SEQ ID NO: 59) | 2L, AE003663 | 2 precursor variants clustered with a copy of mir-2b |
| miR-2b | UAUCACAGCCAGCUUUGAGGAGC (SEQ ID NO: 60) | 2L, AE003620 2L, AE003663 | 2 precursor variants |
| miR-3 | UCACUGGGCAAAGUGUGUCUCA (SEQ ID NO: 61) | 2R, AE003795 | in cluster mir-3 to mir-6 |
| MiR-4 | AUAAAGCUAGACAACCAUUGA (SEQ ID NO: 62) | 2R, AE003795 | in cluster mir-3 to mir-6 |
| miR-5 | AAAGGAACGAUCGUUGUGAUAUG (SEQ ID NO: 63) | 2R, AE003795 | in cluster mir-3 to mir-6 |
| miR-6 | UAUCACAGUGGCUGUUCUUUUU (SEQ ID NO: 64) | 2R, AE003705 | in cluster mir-3 to mir-6 with 3 variants |
| miR-7 | UGGAAGACUAGUGAUUUUGUUGU (SEQ ID NO: 65) | 2R, AE003791 | homologs: human; chr. 19 AC006537, EST BF373391; mouse chr. 17 AC026385, EST AA881786 |
| miR-8 | UAAUACUGUCAGGUAAAGAUGUC (SEQ ID NO: 66) | 2R, AE003805 | |
| miR-9 | UCUUUGGUUAUCUAGCUGUAUGA (SEQ ID NO: 67) | 3L, AE003516 | homologs: mouse, chr. 19, AF155142; human, chr. 5, AC026701, chr. 15, AC005316 |
| miR-10 | ACCCUGUAGAUCCGAAUUUGU (SEQ ID NO: 68) | AE001574 | homologs: mouse, chr 11, AC011194; human, chr. 17, AF287967 |
| miR-11 | CAUCACAGUCUGAGUUCUUGC (SEQ ID NO: 69) | 3R, AE003735 | intronic location |
| miR-12 | UGAGUAUUACAUCAGGUACUGGU (SEQ ID NO: 70) | X, AE003499 | intronic location |
| miR-13a | UAUCACAGCCAUUUUGACGAGU (SEQ ID NO: 71) | 3R, AE003708 X; AE003446 | mir-13a clustered with mir-13b on chr. 3R |
| miR-13b | UAUCACAGCCAUUUUGAUGAGU (SEQ ID NO: 72) | 3R, AE003708 | mir-13a clustered with mir-13b on chr. 3R |
| miR-14 | UCAGUCUUUUUCUCUCUCCUA (SEQ ID NO: 73) | 2R, AE003833 | no signal by Northern analysis |

TABLE 6

Human miRNA sequences and genomic location. From 220 short RNAs sequenced, 100 (45%) corresponded to miRNAs, 53 (24%) to already characterized functional RNAs (rRNA, snRNAs, tRNAs), and 67 (30%) sequences with no database entry. For legend, see Table 1.

| miRNA | sequence (5' to 3') | chr. or EST, acc. nb. | remarks* |
|---|---|---|---|
| let-7a | UGAGGUAGUAGGUUGUAUAGUU (SEQ ID NO: 75) | 9, AC007924, 11, AP001359, 17, AC087784, 22, AL049853 | sequences of chR 9 and 17 identical and clustered with let-7f, homologs: *C. elegans*, AF274345; *C. briggsae*, AF210771, *D. melanogaster*, AE003659 |
| let-7b | UGAGGUAGUAGGUUGUGUGGUU (SEQ ID NO: 76) | 22, AL049853†, ESTs, AI382133, AW028822 | homologs: mouse, EST AI481799; rat, EST, BE120662 |
| let-7c | UGAGGUAGUAGGUUGUAUGGUU (SEQ ID NO: 77) | 21, AP001667 | Homologs: mouse, EST, AA575575 |
| let-7d | AGAGGUAGUAGGUUGCAUAGU (SEQ ID NO: 78) | 17, AC087784, 9, AC007924 | identical precursor sequences |
| let-7e | UGAGGUAGGAGGUUGUAUAGU (SEQ ID NO: 79) | 19, AC018755 | |
| let-7f | UGAGGUAGUAGAUUGUAUAGUU (SEQ ID NO: 80) | 9, AC007924, 17, AC087784, X, AL592046 | sequences of chr 9 and 17 identical and clustered with let-7a |
| miR-15 | UAGCAGCACAUAAUGGUUUGUG (SEQ ID NO: 81) | 13, AC069475 | in cluster with mir-16 homolog |
| miR-16 | UAGCAGCACGUAAAUAUUGGCG (SEQ ID NO: 82) | 13, AC069475 | in cluster with mir-15 homolog |
| miR-17 | ACUGCAGUGAAGGCACUUGU (SEQ ID NO: 83) | 13, AL138714 | in cluster with mir-17 to mir-20 |
| miR-18 | UAAGGUGCAUCUAGUGCAGAUA (SEQ ID NO: 84) | 13, AL138714 | in cluster with mir-17 to mir-20 |
| miR-19a | UGUGCAAAUCUAUGCAAAACUGA (SEQ ID NO: 85) | 13, AL138714 | in cluster with mir-17 to mir-20 |
| miR-19b | UGUGCAAAUCCAUGCAAAACUGA (SEQ ID NO: 86) | 13, AL138714, X, AC002407 | in cluster with mir-17 to mir-20 |
| miR-20 | UAAAGUGCUUAUAGUGCAGGUA (SEQ ID NO: 87) | 13, AL138714 | in cluster with mir-17 to mir-20 |
| miR-21 | UAGCUUAUCAGACUGAUGUUGA (SEQ ID NO: 88) | 17, AC004686, EST, BF326048 | homologs: mouse, EST, AA209594 |
| miR-22 | AAGCUGCCAGUUGAAGAACUGU (SEQ ID NO: 89) | ESTs, AW961681†, AA456477, AI752503, BF030303, HS1242049 | human ESTs highly similar; homologs: mouse, ESTs, e.g. AA823029; rat, ESTs, e.g. BF543690 |
| miR-23 | AUCACAUUGCCAGGGAUUUCC (SEQ ID NO: 90) | 19, AC020916 | homologs: mouse, EST, AW124037; rat, EST, BF402515 |
| miR-24 | UGGCUCAGUUCAGCAGGAACAG (SEQ ID NO: 91) | 9, AF043896, 19, AC020916 | homologs: mouse, ESTs, AA111466, AI286629; pig, EST, BE030976 |
| miR-25 | CAUUGCACUUGUCUCGGUCUGA (SEQ ID NO: 92) | 7, AC073842, EST, BE077684 | human chr 7 and EST identical; highly similar precursors in mouse ESTs (e.g. AI595464); fish precursor different STS: G46757 |

TABLE 6-continued

Human miRNA sequences and genomic location. From 220 short RNAs sequenced, 100 (45%) corresponded to miRNAs, 53 (24%) to already characterized functional RNAs (rRNA, snRNAs, tRNAs), and 67 (30%) sequences with no database entry. For legend, see Table 1.

| miRNA | sequence (5' to 3') | chr. or EST, acc. nb. | remarks* |
|---|---|---|---|
| miR-26a | UUCAAGUAAUCCAGGAUAGGCU (SEQ ID NO: 93) | 3, AP000497 | |
| miR-26b | UUCAAGUAAUUCAGGAUAGGUU (SEQ ID NO: 94) | 2, AC021016 | |
| miR-27 | UUCACAGUGGCUAAGUUCCGCU (SEQ ID NO: 95) | 19, AC20916 | U22C mutation in human genomic sequence |
| miR-28 | AAGGAGCUCACAGUCUAUUGAG (SEQ ID NO: 96) | 3, AC063932 | |
| miR-29 | CUAGCACCAUCUGAAAUCGGUU (SEQ ID NO: 97) | 7, AF017104 | |
| miR-30 | CUUUCAGUCGGADGUUUGCAGC (SEQ ID NO: 98) | 6, AL035467 | |
| miR-31 | GGCAAGAUGCUGGCAUAGCUG (SEQ ID NO: 99) | 9, AL353732 | |
| miR-32 | UAUUGCACAUUACUAAGUUGC (SEQ ID NO: 100) | 9, AL354797 | not detected by Northern blotting |
| miR-33 | GUGCAUUGUAGUUGCAUUG (SEQ ID NO: 101) | 22, Z99716 | not detected by Northern blotting |

*If several ESTs were retrieved for one organism in the database, only those with different precursor sequences are listed.
†precursor structure shown in FIG. 4.

---

The invention claimed is:

1. Isolated nucleic acid molecule selected from the group consisting of
   (a) a nucleotide sequence consisting of SEQ ID NO: 162,
   (b) a nucleotide sequence which is the complement of (a),
   (c) a nucleotide sequence which has an identity of at least 80% to a sequence of (a) or (b) and
   (d) a nucleotide sequence consisting of 60-80 nucleotides which has an identity of at least 80% to SEQ ID NO: 355 or the complement thereof,
   wherein said nucleic acid molecule contains at least one modified nucleotide analog.

2. The nucleic acid molecule of claim 1, wherein the identity of sequence (c) is at least 90%.

3. The nucleic acid molecule of claim 1, wherein the identity of sequence (c) is at least 95%.

4. The nucleic acid molecule of claim 1 which is a miRNA molecule or an analog thereof having a length of from 18-25 nucleotides.

5. The nucleic acid molecule of claim 1, which is a miRNA precursor molecule having a length of 60-80 nucleotides or a DNA molecule coding therefor.

6. The nucleic acid molecule of claim 1, which is single-stranded.

7. The nucleic acid molecule of claim 1, which is at least partially double-stranded.

8. The nucleic acid molecule of claim 1, wherein said molecule is selected from the group consisting of RNA, DNA or nucleic acid analog molecules.

9. A recombinant expression vector comprising the nucleic acid molecule according to claim 1.

10. A pharmaceutical composition containing as an active agent at least one nucleic acid molecule of claim 1 in combination with a pharmaceutically acceptable carrier.

11. The composition of claim 10, wherein said pharmaceutically acceptable carrier is suitable for diagnostic applications.

12. The composition of claim 10, wherein said pharmaceutically acceptable carrier is suitable for therapeutic applications.

13. The composition of claim 10 as a marker or a modulator for developmental or pathogenic processes.

14. The composition of claims 10 as a marker or modulator of developmental disorders, particularly cancer, such a B-cell chronic leukemia.

15. The composition of claim 10 as a marker or modulator of gene expression.

16. The composition of claim 15 as a marker or modulator of the expression of a gene, which is at least partially complementary to said nucleic acid molecule.

17. The nucleic acid molecule according to claim 1, wherein said modified nucleotide analog is a 2' modified nucleotide.

18. The nucleic acid molecule according to claim 1, wherein said modified nucleotide analog is selected from the group consisting of a sugar- or backbone-modified ribonucleotide, a nucleobase-modified ribonucleotide, a deaza nucleotide, and an O- and N-alkylated nucleotide.

19. The nucleic acid molecule according to claim 18, wherein said nucleobase-modified ribonucleotide contains a non-naturally occurring nucleobase selected from the group consisting of uridine modified at the 5-position, cytidine modified at the 5-position, adenosine modified at the 8-position, and guanosine modified at the 8-position.

20. The nucleic acid molecule according to claim 19, wherein said uridine modified at the 5-position is selected from the group consisting of 5-(2-amino)propyl uridine, and 5-bromo uridine; and/or said guanosine modified at the 8-position is 8-bromo guanosine.

21. The nucleic acid molecule according to claim 18, wherein said deaza nucleotide is 7-deaza-adenosine; and/or said O- and N-alkylated nucleotide is N6-methyl adenosine.

22. The nucleic acid molecule according to claim 18, wherein in said sugar-modified ribonucleotide, the 2'-OHgroup is replaced by a group selected from the group consisting of H, OR, R, halo, SH, SR, $NH_2$, NHR, $NR_2$ and CN, wherein R is selected from the group consisting of $C_1$-$C_8$ alkyl, alkenyl and alkynyl and halo is selected from the group consisting of F, Cl, Br and I.

23. The nucleic acid molecule according to claim 18, wherein in said backbone-modified ribonucleotide, the phosphoester group connecting to adjacent ribonucleotides is replaced by a modified group.

24. The nucleic acid molecule according to claim 23, wherein the phosphoester group connecting to adjacent ribonucleotides is replaced by a phosphothioate group.

* * * * *